(12) United States Patent  (10) Patent No.: US 8,835,462 B2
Meyer et al.  (45) Date of Patent: Sep. 16, 2014

(54) MACROCYCLIC PICOLINAMIDES AS FUNGICIDES

(71) Applicant: Dow AgroSciences LLC, Indianapolis, IN (US)

(72) Inventors: Kevin G. Meyer, Zionsville, IN (US); W. John Owen, Carmel, IN (US); James M. Renga, Indianapolis, IN (US); Chenglin Yao, Westfield, IN (US); Benjamin M. Nugent, Brownsburg, IN (US); Jeremy Wilmot, Zionsville, IN (US); Fangzheng Li, Carmel, IN (US); Karla Bravo-Altamirano, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/887,933

(22) Filed: May 6, 2013

(65) Prior Publication Data

US 2013/0296373 A1    Nov. 7, 2013

Related U.S. Application Data

(60) Provisional application No. 61/643,653, filed on May 7, 2012.

(51) Int. Cl.
| | | |
|---|---|---|
| C07D 405/12 | (2006.01) | |
| A01N 43/40 | (2006.01) | |
| A01N 47/18 | (2006.01) | |
| C07D 321/00 | (2006.01) | |

(52) U.S. Cl.
CPC .............. *A01N 43/40* (2013.01); *A01N 47/18* (2013.01); *C07D 321/00* (2013.01); *C07D 405/12* (2013.01)
USPC ......... 514/336; 514/450; 546/281.7; 549/347

(58) Field of Classification Search
None
See application file for complete search history.

(56) References Cited

U.S. PATENT DOCUMENTS

| | | |
|---|---|---|
| 6,706,740 B2 | 3/2004 | Ricks et al. |
| 6,861,390 B2 | 3/2005 | Meyer et al. |
| 2011/0082160 A1 | 4/2011 | Owen et al. |

OTHER PUBLICATIONS

International Search Report issued by the ISA/US, dated Oct. 24, 2013, for International Application No. PCT/US2013/039729, 4 pages.
Written Opinion of the ISA/US, dated Oct. 4, 2013, for International Application No. PCT/US2013/039729, 4 pages.

*Primary Examiner* — Zinna Northington Davis
(74) *Attorney, Agent, or Firm* — C. W. Arnett; Faegre Baker Daniels LLP

(57) ABSTRACT

The disclosure relates to macrocyclic picolinamides of Formula I and their use as fungicides.

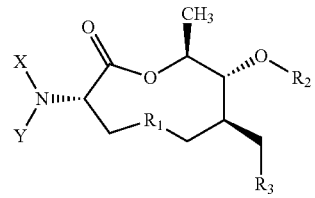

20 Claims, No Drawings

MACROCYCLIC PICOLINAMIDES AS FUNGICIDES

CROSS REFERENCE TO RELATED APPLICATIONS

This application claims the benefit of U.S. Provisional Patent Application Ser. No. 61/643,653 filed May 7, 2012, which is expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

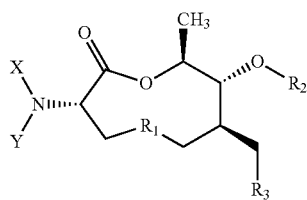

I

X is H or C(O)R$_6$;
Y is H, C(O)R$_6$, or Q;
Q is

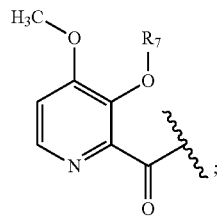

R$_1$ is O;
R$_2$ is H, alkyl, alkenyl, aryl, heterocyclyl, silyl, each substituted with 0, 1 or multiple R$_5$, —C(O)R$_5$;
R$_3$ is phenyl or cyclohexyl;
R$_4$ is alkyl or alkoxy, substituted with 0, 1, or multiple R$_5$;
R$_5$ is hydroxy, alkyl, alkenyl, halo, haloalkyl, alkoxy, haloalkoxy, C(O)R$_8$, arylalkoxy, or aryl, where each R$_5$ is substituted with 0, 1, or multiple R$_9$;
R$_6$ is alkoxy, benzyloxy, substituted with 0, 1, or multiple R$_9$;
R$_7$ is H, —C(O)R$_4$, or —CH$_2$OC(O)R$_4$;
R$_8$ is hydroxy, alkyl, alkoxy, N(R$_9$)$_2$, or arylalkoxy; and
R$_9$ is H or alkyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by the those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or cyclic saturated carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched, or cyclic carbon chain containing one or more double bonds including, but not limited to, ethenyl, propenyl, butenyl, isopropenyl, isobutenyl, cyclopentenyl, cyclohexenyl, and the like.

The term "alkynyl" refers to a branched or unbranched carbon chain containing one or more triple bonds including, but not limited to, propynyl, butyryl and the like.

The term "aryl" refers to any aromatic, mono- or bi-cyclic, containing 0 heteroatoms.

The term "heterocyclyl" refers to any aromatic or non-aromatic ring, mono- or bi-cyclic, containing one or more heteroatoms The term "alkoxy" refers to an —OR substituent.

The term "alkoxycarbonyl" refers to a —C(O)—OR substituent.

The term "alkylcarbonyl" refers to a —C(O)—R substituent.

The term "alkylsulfonyl" refers to an —SO$_2$—R substituent.

The term "haloalkylsulfonyl" refers to an —SO$_2$—R substituent where R is fully or partially substituted with Cl, F, I, or Br or any combination thereof.

The term "alkylthio" refers to an —S—R substituent.

The term "haloalkylthio" refers to an alkylthio, which is substituted with Cl, F, I, or Br or any combination thereof.

The term "alkylaminocarbonyl" refers to a —C(O)—N(H)—R substituent.

The term "dialkylaminocarbonyl" refers to a —C(O)—N(R)$_2$ substituent.

The term "alkylcycloalkylamino" refers to a cycloalkylamino substituent that is substituted with an alkyl group.

The term "trialkylsilyl" refers to —Si(R)$_3$.

The term "cyano" refers to a —C≡N substituent.

The term "hydroxyl" refers to an —OH substituent.

The term "amino" refers to a —NH$_2$ substituent.

The term "alkylamino" refers to a —N(H)—R substituent.

The term "dialkylamino" refers to a —N(R)$_2$ substituent.

The term "alkoxyalkoxy" refers to —O(CH$_2$)$_n$O(CH$_2$)$_n$ where n is an integer selected from the list 1, 2, 3, 4, 5, or 6.

The term "arylalkoxy" refers to —O(CH$_2$)$_n$Ar where n is an integer selected from the list 1, 2, 3, 4, 5, or 6.

The term "arylalkyl" refers to —(CH$_2$)$_n$Ar where n is an integer selected from the list 1, 2, 3, 4, 5, or 6.

The term "alkoxyalkyl" refers to an alkoxy substitution on an alkyl.

The term "haloalkoxyalkyl" refers to an alkoxy substitution on an alkyl which may be partially substituted with halogen atoms.

The term "hydroxyalkyl" refers to an alkyl which is substituted with a hydroxyl group.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "haloalkenyl" refers to an alkenyl, which is substituted with Cl, F, I, or Br or any combination thereof.

The term "haloalkynyl" refers to an alkynyl which is substituted with Cl, F, I, or Br or any combination thereof.

The term "halogen" or "halo" refers to one or more halogen atoms, defined as F, Cl, Br, and I.

The term "hydroxycarbonyl" refers to a —C(O)—OH substituent.

The term "nitro" refers to a —$NO_2$ substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DESCRIPTION

The compounds of the present disclosure may be applied by any of a variety of known techniques, either as the compounds or as formulations comprising the compounds. For example, the compounds may be applied to the roots, or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

In some embodiments, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis*, *Bacillus subtilis* strain QST713, benalaxyl, benomyl, benthiavalicarb-isopropyl, benzylaminobenzenesulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxinecopper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, amino cyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; impect stage: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). It may be understood by those skilled in the art that $R_2$ and $R_3$ may be differentially substituted. The following descriptions and examples are provided for illustrative purposes and should not be construed as limiting in terms of substituents or substitution patterns.

Compounds of Formula Ia, where X is tert-butoxycarbonyl (BOC) or benzyloxycarbonyl (CBz) and $R_2$ is a silyl group such as tert-butyldimethylsilyl (TBS) or triisopropylsilyl (TIPS) can be prepared by the method shown in Scheme I. Lactone II can be formed from UK-2A by treatment with an aqueous solution of hydrochloric acid (HCl) at elevated temperatures. Compounds of Formula III, where $R_2$ is a silyl group such as tert-butyldimethylsilyl (TBS) or triisopropylsilyl (TIPS) can be prepared from lactone II by the treatment with a silyl halide or silyl triflate, such as triisopropyl trifluoromethanesulfonate, and a base, such as 2,6-lutidine in an aprotic solvent such as dichloromethane (DCM) at 0° C. Compounds of Formula IV, where $R_2$ is as defined above can be prepared from compounds of Formula III by treatment with a reducing agent, such as diisobutylaluminum hydride (DIBAL-H), in an aprotic solvent such as DCM. Compounds of Formula V, where $R_2$ is as defined above and X is BOC or CBz can be prepared from compounds of Formula IV by treatment with a protected aziridine, such as (S)-1-tert-butyl 2-methyl aziridine-1,2-dicarboxylate in the presence of a Lewis acid such as boron trifluoride etherate, in an aprotic solvent such as DCM. Compounds of Formula Ia where X and $R_2$ are as defined above can be prepared from compounds of Formula V by treatment with a base such as lithium hydroxide (LiOH) in a solvent mixture such as tetrahydrofuran (THF)/water, followed by treatment with an activating reagent, such as 2-methyl-6-nitrobenzoic anhydride (MNBA) in the presence of a base such as 4-dimethylaminopyridine (DMAP) in a solvent such as toluene under high dilution.

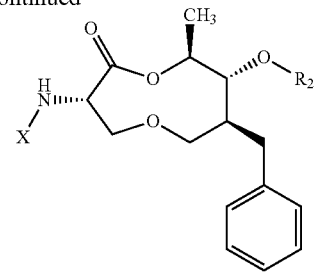

Ia

Compounds of Formula Ie, where $R_2$ is alkyl or alkenyl and X and Y are protecting groups such as BOC can be prepared by the method shown in Scheme II. Compounds of Formula Ic, where X and Y are protecting groups such as BOC and $R_2$ is a silyl group, such as TBS or TIPS, can be prepared from compounds such as Ib, where X is a protecting group such as BOC and $R_2$ is a silyl group, such as TBS or TIPS by treatment with a dicarbonate such as di-tert-butyl dicarbonate in the presence of a base such as DMAP in an aprotic solvent such as acetonitrile ($CH_3CN$). Alcohols of Formula Id, where X and Y are as defined above can be prepared from compounds of Formula Ic by treatment with a fluorinating agent, such as tetrabutylammonium fluoride (TBAF) in an aprotic solvent such as THF. Compounds of Formula Ie, where X and Y are as defined above and $R_2$ is alkenyl can be prepared from compounds of Formula Id by treatment with an allyl carbonate such as bis(2-methylallyl)carbonate, in the presence of a catalyst such as tris(dibenzylideneacetone)dipalladium(0) ($Pd_2(dba)_3$) and a ligand such as 1,1'-bis(diphenylphosphino)ferrocene (dppf) in an aprotic solvent such as THF at an elevated temperature, such as 60° C. Compounds of Formula Ie where $R_2$ is alkyl can be formed from compounds of Formula Id where $R_2$ is alkenyl by treating with hydrogen gas in the presence of a catalyst such as palladium on carbon (Pd/C) in a solvent such as ethyl acetate (EtOAc).

Scheme I

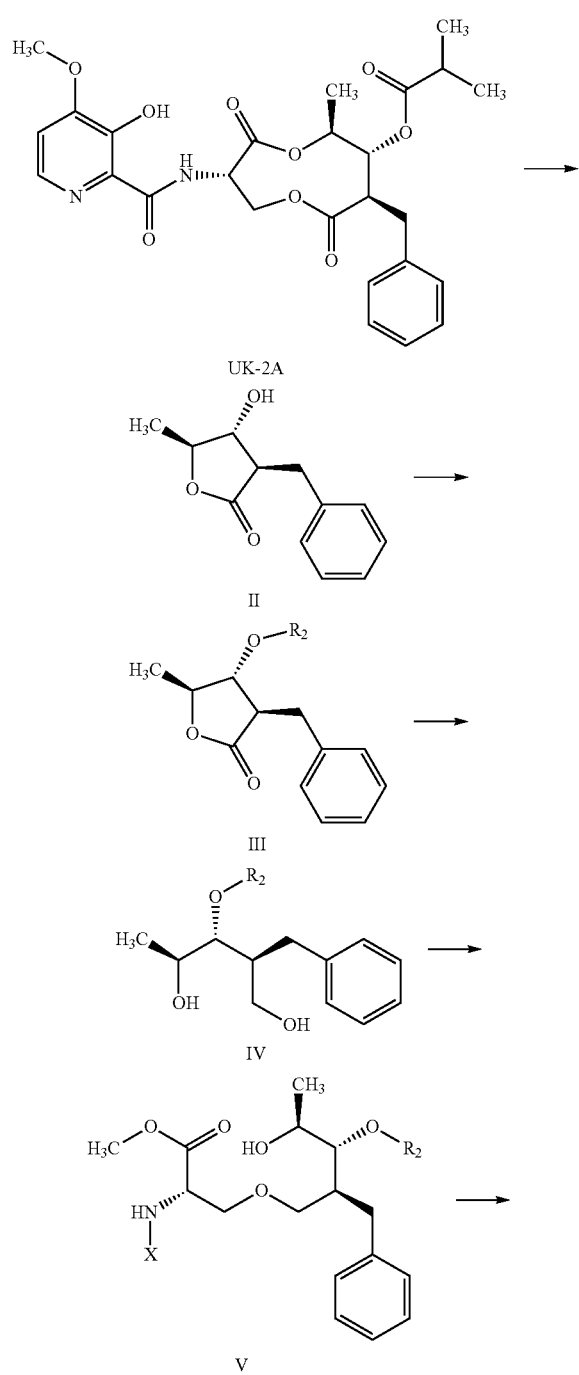

Scheme II

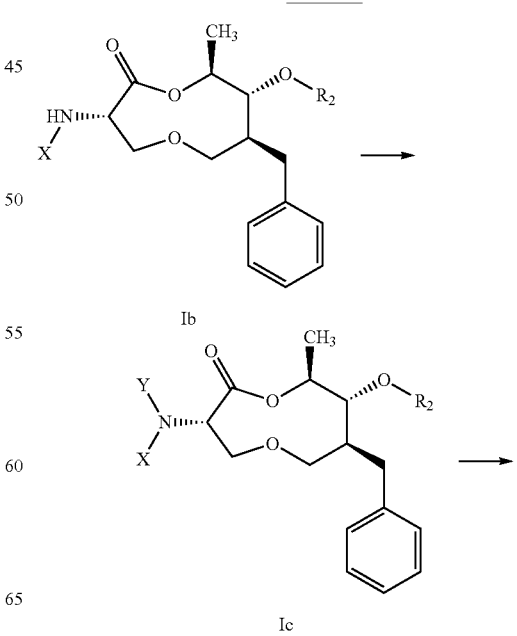

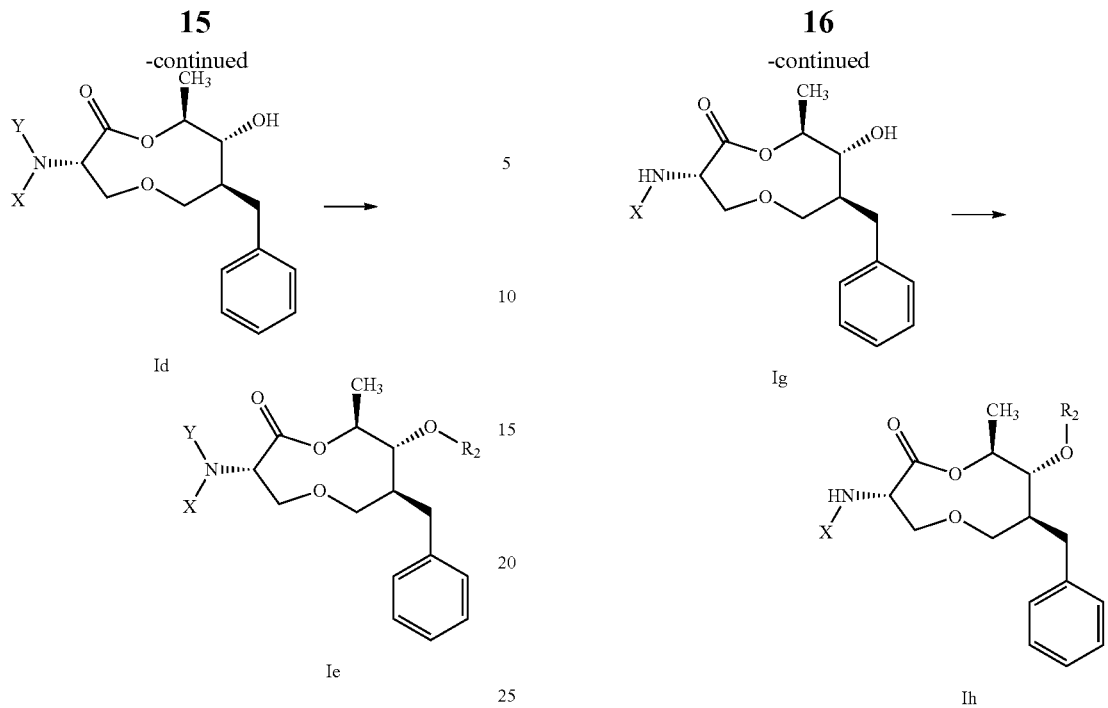

Compounds of Formula Ih, where $R_2$ is alkyl, acyl or phenyl and X is a protecting group such as BOC can be prepared by the method shown in Scheme III. Compounds of Formula Ig, where X is protecting groups such as BOC can be prepared from compounds such as If, where X is a protecting group such as BOC and $R_2$ is a silyl group, such as TBS or TIPS, by treatment with a fluorinating agent, such as TBAF in an aprotic solvent such as THF. Compounds of Formula Ih, where X is defined above and $R_2$ is methyl can be prepared from compounds of Formula Ig by treatment with an alkylating agent, such as trimethyloxonium tetrafluoroborate in the presence of an amine base, such as N1,N1,N8,N8-tetramethylnaphthalene-1,8-diamine (proton sponge), in an aprotic solvent such as DCM at 0° C. Compounds of Formula Ih, where X is defined as above and $R_2$ is acyl can be prepared from compounds of Formula Ig by treatment with and acyl halide, such as cyclopropanecarbonyl chloride, benzyl chloride or isobutyryl chloride, in the presence of a base, such as pyridine. Compounds of Formula Ih, where X is defined as above and $R_2$ is phenyl can be prepared from compounds of Formula Ig by treatment with a phenylating reagent, such as 2-(trimethylsilyl)phenyl trifluoromethanesulfonate in conjunction with a fluorinating reagent, such as cesium fluoride (CsF), in a solvent such as $CH_3CN$.

Compounds of Formula Ik, where $R_8$ is alkyl and X is a protecting group such as BOC can be prepared by the method shown in Scheme IV. Compounds of Formula Ij, where $R_8$ is alkyl and X is a protecting group such as BOC can be prepared from alcohols such as Ii by reaction with a propiolate, such as methyl propiolate, in the presence of an amine, such as 1,4-diazabicyclo[2.2.2]octane (DABCO) in an aprotic solvent such as DCM. Compounds of Formula Ik can be prepared from compounds of Formula Ij by treatment with hydrogen gas in the presence of a catalyst such as Pd/C in a solvent such as EtOAc.

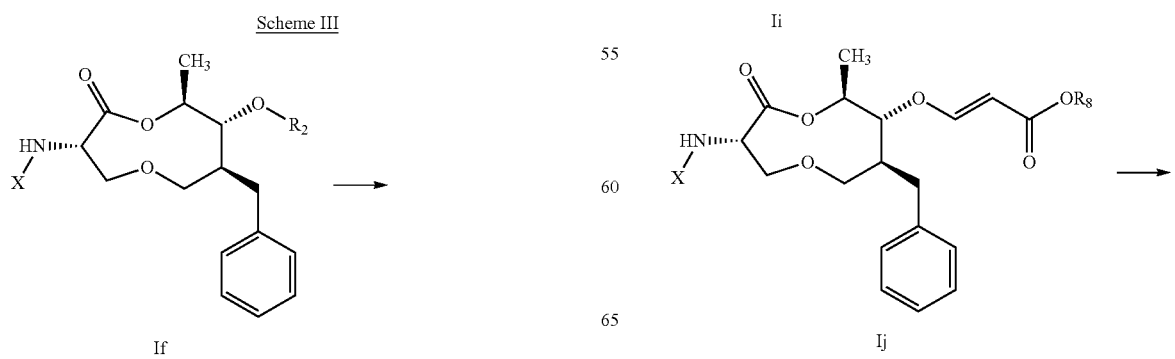

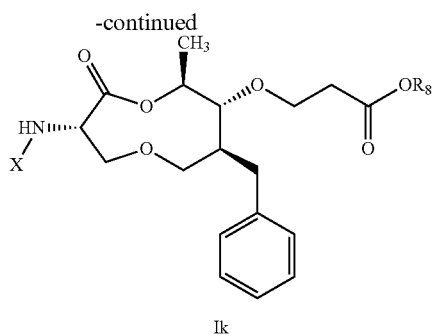

Ik

Compounds of Formula Io and Iq, where X is a protecting group such as BOC can be prepared by the method shown in Scheme V. Compounds of Formula Im, where X is a protecting group such as BOC can be prepared from alcohols such as Il by reaction with benzyl propiolate, in the presence of an amine, such as DABCO in an aprotic solvent such as DCM. Compounds of Formula In, where X is a protecting group such as BOC, can be prepared from compounds of Formula Im by treatment with hydrogen gas in the presence of a catalyst such as Pd/C in a solvent such as EtOAc. Compounds of Formula Ip, where X is a protecting group such as BOC, can be prepared from compounds of Formula In by reaction with dimethylamine hydrochloride in the presence of a carbodiimide, such as 1-ethyl-3-(3-dimethylaminopropyl) carbodiimide (EDC), and hydroxybenzotriazole (HOBT), and a base, such as N,N-diisopropylethylamine in a solvent such as N,N-dimethylformamide (DMF). Compounds of Formula Io, where X is a protecting group such as BOC, can be prepared from compounds of Formula In by treatment with a reducing agent, such as borane ($BH_3$) in an aprotic solvent such as THF. Compounds of Formula Iq, where X is a protecting group such as BOC, can be prepared from compounds of Formula Io by treatment with an alkylating agent, such as trimethyloxonium tetrafluoroborate in the presence of an amine base, such as proton sponge, in an aprotic solvent such as DCM.

Scheme V

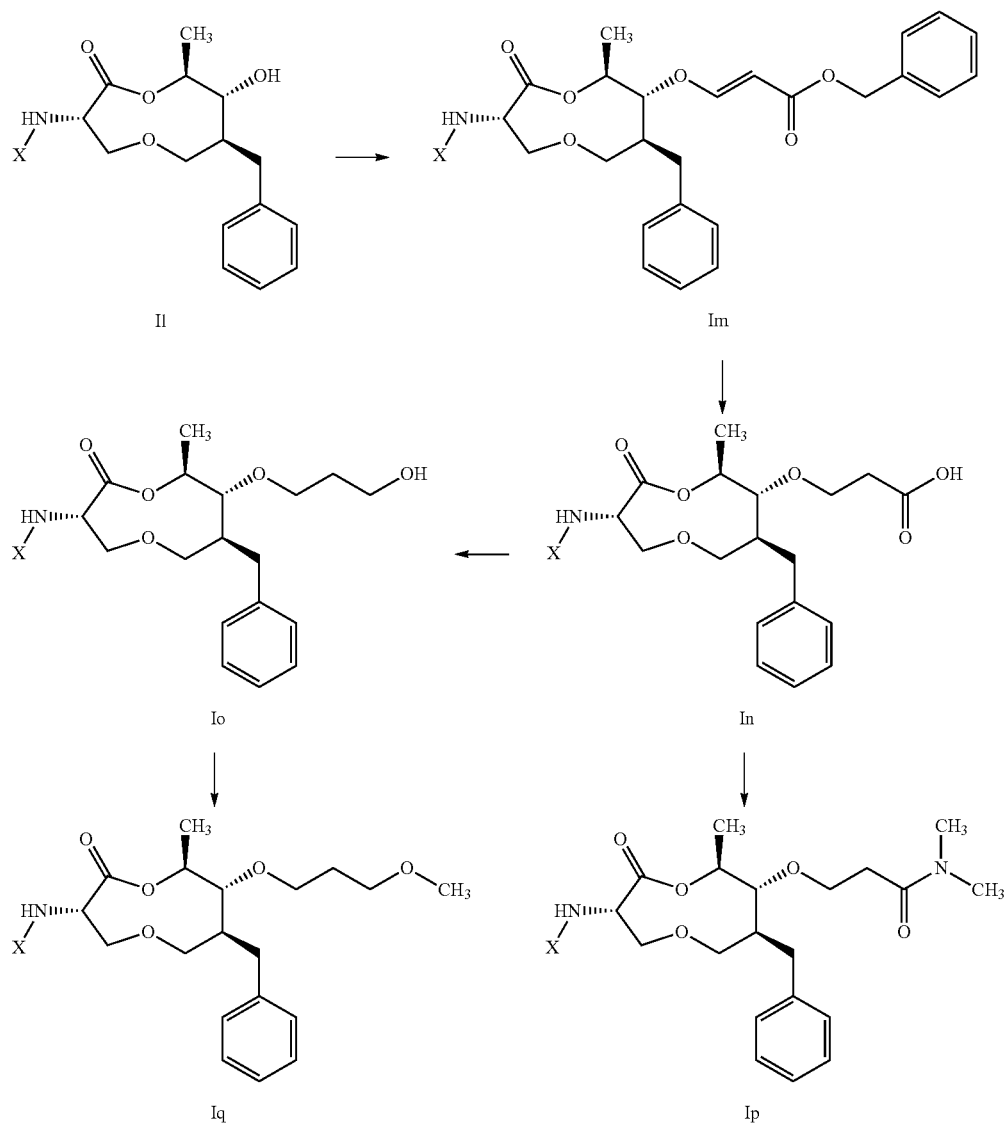

Compounds of Formula Iu and Iy, where X is a protecting group such as BOC can be prepared by the method shown in Scheme VI. Compounds of Formula Is, where X is a protecting group such as BOC can be prepared from alcohols such as Ir by reaction with but-3-yn-2-one, in the presence of an amine, such as DABCO in an aprotic solvent such as DCM. Compounds of Formula It and Iw, where X is a protecting group such as BOC, can be prepared from compounds of Formula Is by treatment with hydrogen gas in the presence of a catalyst such as Pd/C in a solvent such as EtOAc. Compounds of Formula Iu, where X is a protecting group such as BOC, can be prepared from compounds of Formula It by reaction with an alkylating agent, such as trimethyloxonium tetrafluoroborate in the presence of an amine base, such as proton sponge, in an aprotic solvent such as DCM. Compounds of Formula Ix, where X is a protecting group such as BOC, can be prepared from compounds of Formula Iw by treatment with methyltriphenylphosphonium bromide and a base, such as n-butyllithium, in an aprotic solvent such as THF. Compounds of Formula Iy, where X is a protecting group such as BOC, can be prepared from compounds of Formula Ix by treatment with hydrogen gas in the presence of a catalyst such as Pd/C in a solvent such as EtOAc.

Scheme VI

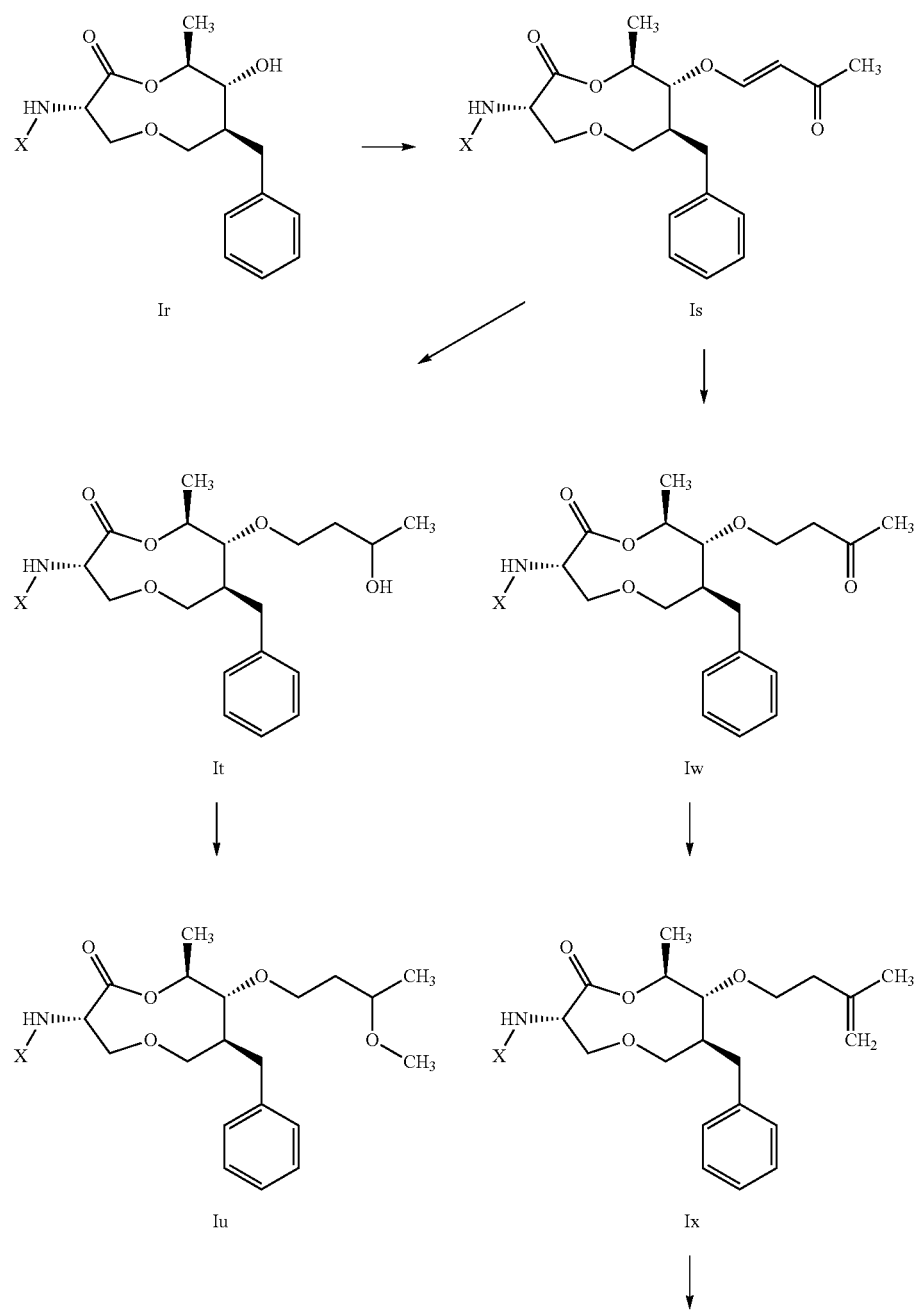

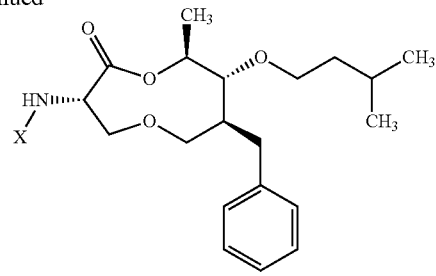

Iy

Compounds of Formula Idd, where $R_2$ is as originally defined, can be prepared by the method shown in Scheme VII. Compounds of Formula Icc, where $R_2$ is as originally defined, can be prepared from compounds of Formula Iz or compounds of Formula Iaa, where $R_2$ and $R_3$ are as originally defined and X and Y are protecting group such as BOC, by treatment with an acid such as a 4.0 molar (M) hydrogen chloride (HCl) solution in dioxane in a solvent such as DCM. Alternatively, compounds of Formula Icc can be prepared from compounds of Formula Iz or compounds of Formula Iaa, where $R_2$ and $R_3$ are as originally defined, by treatment with a triflate such as trimethylsilyl trifluoromethanesulfonate in the presence of a base such 2,6-lutidine in an aprotic solvent such as DCM, followed by treatment with a protic solvent such as methanol (MeOH). Alternatively, compounds of Formula Icc can be prepared from compounds of Formula Ibb, where $R_2$ and $R_3$ are as originally defined, by treatment with hydrogen in the presence of a catalyst such as Pd/C in a solvent such as MeOH. Compounds of Formula Idd, where $R_2$ and $R_3$ are as originally defined, can be prepared from compounds of Formula Icc, where $R_2$ and $R_3$ are as originally defined, by treatment with 3-hydroxy-4-methoxypicolinic acid in the presence of a base such as 4-methylmorpholine and a peptide coupling reagent such as O-(7-azabenzotriazol-1-yl)-N,N,N',N'-tetramethyluronium hexafluorophosphate (HATU) in an aprotic solvent such as DCM.

Scheme VII

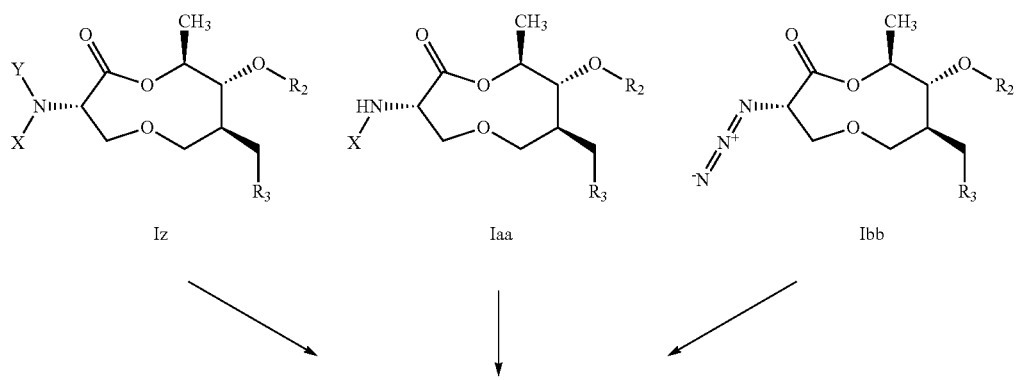

Iz    Iaa    Ibb

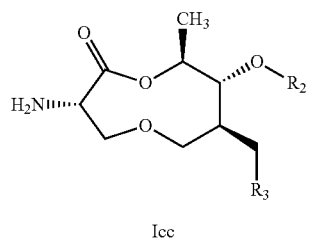

Icc

-continued

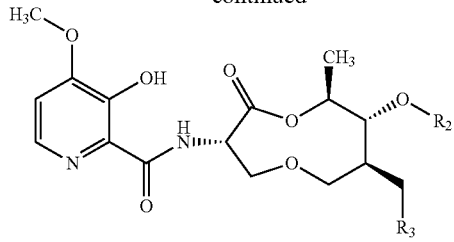

Idd

Compounds of Formula Iff, where $R_2$ and $R_7$ are as originally defined, can be prepared by the method shown in Scheme VIII. Compounds of Formula Iff can be prepared from compounds of Formula Iee, where $R_2$ is as originally defined, by treatment with the appropriate alkyl halide in the presence of a reagent such as sodium iodide (NaI) and a base such as sodium carbonate ($Na_2CO_3$) in a solvent such as acetone or an acyl halide in the presence of an amine base, such as pyridine or triethylamine, in an aprotic solvent such as DCM.

Compounds of Formula Ihh, where $R_2$ is as originally defined, can be prepared by the method shown in Scheme IX. Compounds of Formula Ihh can be prepared from compounds of Formula Igg, where $R_2$ is as originally defined, by treatment with hydrogen gas in the presence of a catalyst, such as rhodium on carbon (Rh/C), in a solvent such as THF, at an elevated temperature such as 70° C.

Scheme VIII

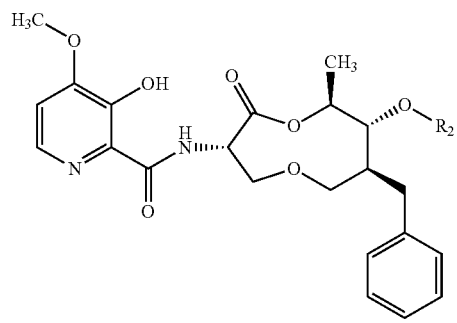

Iee

Scheme IX

Igg

Iff

Ihh

The following examples are presented to illustrate the various aspects of the compounds of the present disclosure and should not be construed as limitations to the claims.

EXAMPLES

Example 1

Step 1: Preparation of (3R,4R,5S)-3-benzyl-4-hydroxy-5-methyldihydrofuran-2(3H)-one

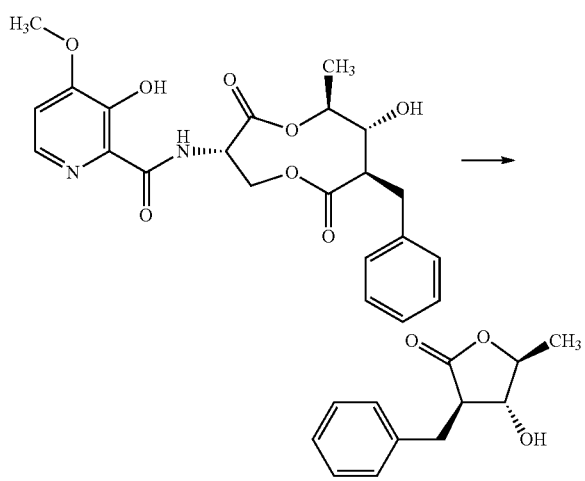

A suspension of N-((3S,7R,8R,9S)-7-benzyl-8-hydroxy-9-methyl-2,6-dioxo-1,5-dioxonan-3-yl)-3-hydroxy-4-methoxypicolinamide, prepared as described by Ricks, Michael J. et al. in U.S. Pat. No. 6,706,740 2004, (20.0 grams (g), 38.7 millimole (mmol), 1.00 equivalent (equiv)) in 6M HCl (200 milliliters (mL)) was heated to 100° C. with rapid stirring. After 1 hour (h), the resulting brown solution was cooled to 23° C. and extracted with diethyl ether (Et$_2$O; 2×200 mL). The organic extracts were combined, washed with saturated (sat'd) aqueous sodium bicarbonate (NaHCO$_3$) solution (100 mL), dried over magnesium sulfate (MgSO$_4$), filtered, and concentrated to provide (3R,4R,5S)-3-benzyl-4-hydroxy-5-methyldihydrofuran-2(3H)-one (5.62 g, 70%) as a tan solid.

Example 1

Step 2: Preparation of (3R,4R,5S)-3-benzyl-5-methyl-4-(triisopropylsilyloxy)dihydrofuran-2(3H)-one

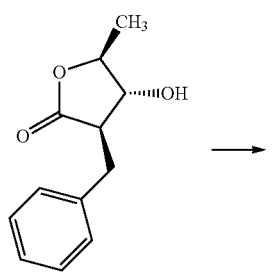

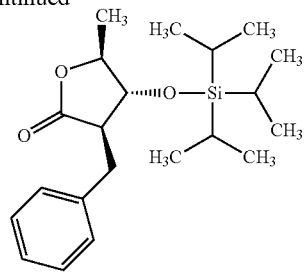

To a solution of (3R,4R,5S)-3-benzyl-4-hydroxy-5-methyldihydrofuran-2(3H)-one (6.61 g, 32.1 mmol, 1.00 equiv) in dichloromethane (CH$_2$Cl$_2$; 100 mL, 0.321 M) at 0° C. (ice water bath) were added 2,6-lutidine (4.81 g, 44.9 mmol, 1.40 equiv) and triisopropyl trifluoromethanesulfonate (10.3 mL, 38.5 mmol, 1.20 equiv). The resulting solution was removed from the cooling bath and stirred at 23° C. for 16 h. The reaction mixture was then poured into sat'd aqueous NaHCO$_3$ solution (100 mL) and shaken until gas evolution ceased. The phases were separated and the aqueous phase was extracted with CH$_2$Cl$_2$ (2×100 mL). The combined organic phases were dried over sodium sulfate (Na$_2$SO$_4$), filtered, and concentrated to provide a yellow oil. Purification by automated silica gel column chromatography (0-10% EtOAc in hexanes) provided (3R,4R,5S)-3-benzyl-5-methyl-4-(triisopropylsilyloxy)dihydrofuran-2(3H)-one (11.28 g, 87%) as a yellow oil: IR (neat film) 2942, 2865, 1777, 1462, 1382, 1172, 1112, 1068, 1014, 949, 881, 676 cm$^{-1}$; $^1$H NMR (400 MHz, CDCl$_3$) δ 7.35-7.27 (m, 2H), 7.24-7.18 (m, 3H), 4.43-4.32 (m, 1H), 4.01 (t, J=3.3 Hz, 1H), 3.17-3.05 (m, 1H), 3.05-2.93 (m, 1H), 2.88 (ddd, J=7.5, 6.2, 3.7 Hz, 1H), 1.23-1.14 (m, 3H), 1.01-0.84 (m, 21H); $^{13}$C NMR (101 MHz, CDCl$_3$) δ 177.31, 137.77, 129.31, 128.76, 127.03, 83.82, 52.66, 35.12, 19.17, 17.92, 17.71, 12.29, 12.21.

Example 1

Step 3: Preparation of (2S,3R,4S)-2-benzyl-3-(triisopropylsilyloxy)pentane-1,4-diol

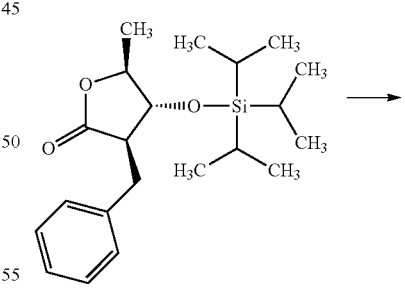

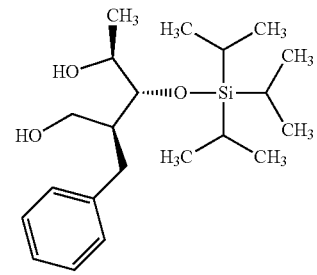

To a solution of (3R,4R,5S)-3-benzyl-5-methyl-4-(triisopropylsilyloxy)-dihydrofuran-2(3H)-one (9.42 g, 26.0 mmol, 1.00 equiv) in CH$_2$Cl$_2$ (130 mL, 0.2 M) at −78° C. (dry ice/acetone bath) was added a 1 M solution of diisobutylaluminum hydride in hexane (DIBAL-H, 65.0 mL, 65.0 mmol, 2.50 equiv). The resulting colorless solution was removed from the cold bath and stirred at 23° C. for 18 h, cooled to 0° C. (ice water bath), and quenched with sat'd aqueous Rochelle's salt solution (200 mL) and Et$_2$O (200 mL). The resulting slurry was stirred vigorously until the mixture became clear and biphasic (1.5 h) and the resulting phases were separated. The aqueous phase was extracted with Et$_2$O (2×200 mL). The combined organic phases were dried over MgSO$_4$, filtered, and concentrated to provide an oil. Purification by automated silica gel column chromatography (0-20% acetone in hexanes) provided (2S,3R,4S)-2-benzyl-3-(triisopropylsilyloxy)pentane-1,4-diol (6.78 g, 71.2%) as a white solid: $^1$H NMR (400 MHz, CDCl$_3$) δ 7.35-7.08 (m, 5H), 4.11-3.96 (m, 1H), 3.95-3.77 (m, 2H), 3.57-3.40 (m, 1H), 3.09 (d, J=2.5 Hz, 2H), 2.93-2.76 (m, 2H), 2.04 (dd, J=5.7, 2.9 Hz, 1H), 1.35 (d, J=6.6 Hz, 3H), 1.12 (d, J =3.6 Hz, 1H), 1.05 (s, 20H); $^{13}$C NMR (101 MHz, CDCl$_3$) δ 141.12, 129.10, 128.42, 125.98, 71.23, 59.84, 48.58, 34.81, 19.10, 18.18, 12.72; ESIMS m/z 365.3 ([M−H]$^−$).

Example 1

Step 4: Preparation of (R)-benzyl 3-((2S,3R,4S)-2-benzyl-4-hydroxy-3-(triisopropylsilyloxy)pentyloxy)-2-(tert-butoxycarbonylamino)propanoate

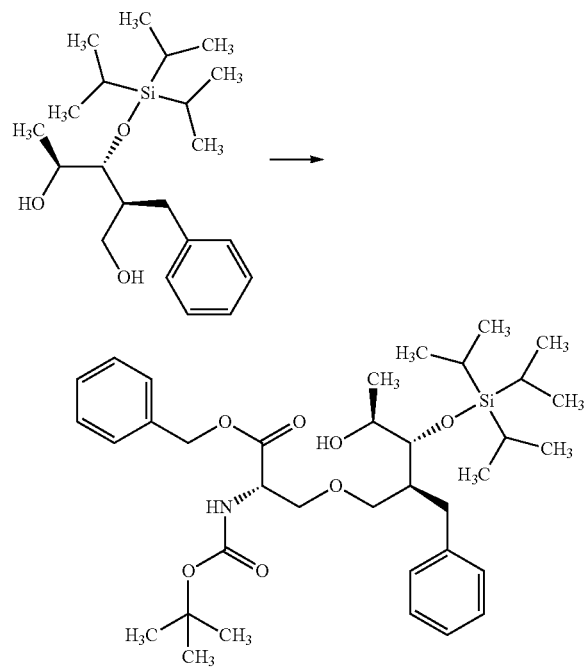

To a solution of (2S,3R,4S)-2-benzyl-3-(triisopropylsilyloxy)pentane-1,4-diol (1.16 g, 3.17 mmol, 2.00 equiv) and (S)-2-benzyl-1-tert-butyl-aziridine-1,2-dicarboxylate (440 milligrams (mg), 1.59 mmol, 1.00 equiv) in CH$_2$Cl$_2$ (9.6 mL, 0.17 M) at −78° C. (dry ice/acetone bath) was added boron trifluoride diethyl etherate (40 microliters (uL), 0.32 mmol, 0.2 equiv). The resulting mixture was warmed to 0° C. (ice water bath) for 4 h, then warmed to 23° C. for 16 h. The reaction was quenched with sat'd aqueous NaHCO$_3$ solution (20 mL) and the phases were separated. The aqueous phase was extracted with CH$_2$Cl$_2$ (2×20 mL), and the combined organic phases were dried over Na$_2$SO$_4$, filtered, and concentrated to provide a colorless oil. Purification by automated silica gel column chromatography (0-10% EtOAc in CH$_2$Cl$_2$) provided (R)-benzyl 3-((2S,3R,4S)-2-benzyl-4-hydroxy-3-(triisopropylsilyloxy)pentyloxy)-2-(tert-butoxycarbonylamino)propanoate (447 mg, 44%) as a colorless oil: IR (neat film) 3445, 2942, 2866, 1745, 1714, 1496, 1455, 1366, 1343, 1248, 1161, 1092, 1059, 882, 733, 698 cm$^{-1}$; $^1$H NMR (400 MHz, CDCl$_3$) δ 7.42-7.28 (m, 5H), 7.25-7.08 (m, 5H), 5.43 (d, J=8.4 Hz, 1H), 5.26-5.09 (m, 2H), 4.56-4.38 (m, 1H), 3.85 (d, J=3.8 Hz, 1H), 3.80-3.68 (m, 2H), 3.62 (dd, J=9.3, 3.0 Hz, 1H), 3.50 (dd, J=9.3, 2.7 Hz, 1H), 3.33 (dd, J=9.3, 5.6 Hz, 1H), 2.91 (dd, J=13.7, 5.4 Hz, 1H), 2.75 (d, J=3.4 Hz, 1H), 2.63 (dd, J=13.6, 10.3 Hz, 1H), 2.04 (s, 1H), 1.44 (s, 9H), 1.32-1.21 (m, 3H), 1.04 (s, 21H); $^{13}$C NMR (101 MHz, CDCl$_3$) δ 170.34, 155.39, 141.00, 135.24, 129.08, 128.60, 128.43, 128.36, 128.23, 125.94, 80.02, 71.08, 70.83, 69.30, 67.32, 54.15, 46.16, 34.99, 28.32, 19.61, 18.22, 12.91; HRMS-ESI (m/z) [M+Na]$^+$ calc'd for C$_{36}$H$_{57}$NO$_7$SiNa, 666.3797. found, 666.3808.

Example 1

Step 5: Preparation of (R)-3-((2S,3R,4S)-2-benzyl-4-hydroxy-3-(triisopropylsilyloxy)pentyloxy)-2-(tert-butoxycarbonylamino)propanoic acid

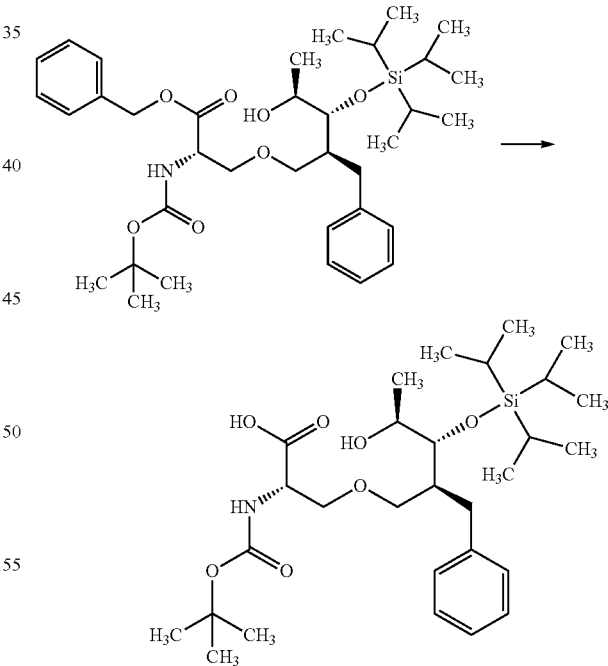

To a solution of (R)-benzyl 3-((2S,3R,4S)-2-benzyl-4-hydroxy-3-(triisopropylsilyloxy)pentyloxy)-2-(tert-butoxycarbonylamino)propanoate (410 mg, 0.637 mmol, 1.00 equiv) in EtOAc (13.4 mL, 0.05 M) was added 5% Pd/C (71 mg, 0.033 mmol, 0.05 equiv). The vessel was capped with a septum and the atmosphere replaced with 1 atmosphere (atm) H$_2$ via a needle-equipped balloon. This suspension was stirred for 7 h, filtered through a plug of Celite®, and the plug was washed with EtOAc. Solvent removal provided (R)-3-((2S,3R,4S)-2-benzyl-4-hydroxy-3-(triisopropylsilyloxy)pentyloxy)-2-(tert-butoxycarbonylamino)propanoic acid (352 mg, 100%) as a hard, white foam: IR (neat film) 2944, 2867, 1706, 1163, 1092, 1063, 907, 731 cm$^{-1}$; $^1$H NMR (400 MHz, CDCl$_3$) δ 7.26 (s, 2H), 7.21-7.10 (m, 3H), 5.44 (d, J=7.7 Hz, 1H), 4.45 (s, 1H), 3.88 (t, J=6.2 Hz, 1H), 3.78 (dd, J=5.8, 2.5 Hz, 2H), 3.70-3.51 (m, 2H), 3.33 (dd, J=9.3, 5.7 Hz, 1H), 2.90 (dd, J=13.6, 5.2 Hz, 1H), 2.67 (dd, J=13.7, 10.5 Hz, 1H), 2.05 (s, 1H), 1.45 (s, 9H), 1.28 (d, J=6.3 Hz, 3H), 1.04 (s, 21H); $^{13}$C NMR (101 MHz, CDCl$_3$) δ 173.08, 155.56, 140.78, 129.08, 128.37, 125.96, 80.25, 71.20, 71.03, 69.08, 53.81, 46.81, 35.18, 28.30, 19.57, 18.20, 12.88; HRMS-ESI (m/z) [M+Na]$^+$ calc'd for C$_{29}$H$_{51}$NO$_7$SiNa, 576.3327. found, 576.3341.

Example 1

Step 6: Preparation of tert-butyl (3S,7S,8R,9S)-7-benzyl-9-methyl-2-oxo-8-(triisopropylsilyloxy)-1,5-dioxonan-3-ylcarbamate (Compound 47)

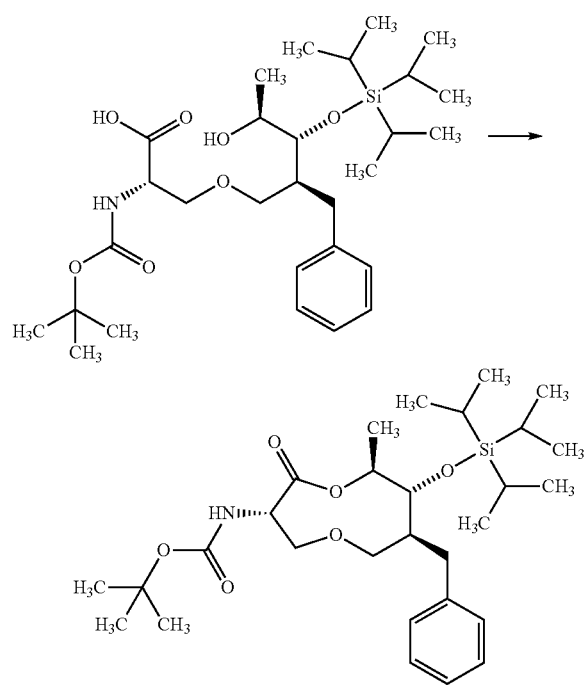

To a solution of DMAP (442 mg, 3.62 mmol, 6.00 equiv) and 2-methyl-6-nitrobenzoic anhydride (415 mg, 1.21 mmol, 2.00 equiv) in CH$_2$Cl$_2$ (92 mL, 6.5 mM) was added a solution of (R)-3-((2S,3R,4S)-2-benzyl-4-hydroxy-3-(triisopropylsilyloxy)pentyloxy)-2-(tert-butoxycarbonylamino)propanoic acid (334 mg, 0.603 mmol, 1.00 equiv) in CH$_2$Cl$_2$ (15 mL) via a syringe pump over 8 h. The resulting solution was stirred at room temperature for an additional 8 h, concentrated, and purified by automated silica gel column chromatography (0-20% hexanes in acetone) to provide tert-butyl (3S,7S,8R, 9S)-7-benzyl-9-methyl-2-oxo-8-(triisopropylsilyloxy)-1,5-dioxonan-3-ylcarbamate (318 mg, 98%) as a colorless oil: $^1$H NMR (400 MHz, CDCl$_3$) δ 7.34-7.07 (m, 5H), 5.30-5.14 (m, 1H), 5.11 (d, J=8.1 Hz, 1H), 4.53 (q, J=8.3 Hz, 1H), 4.08 (dd, J=11.6, 6.9 Hz, 1H), 3.88 (dd, J=6.3, 5.0 Hz, 1H), 3.60 (dd, J=11.7, 5.9 Hz, 1H), 3.44 (d, J=11.6 Hz, 1H), 3.07 (t, J=10.3 Hz, 1H), 2.92 (dd, J=13.3, 4.0 Hz, 1H), 2.76 (t, J=12.4 Hz, 1H), 1.99 (td, J=10.6, 5.0 Hz, 1H), 1.50-1.38 (m, 12H), 1.14-0.99 (m, 21H); $^{13}$C NMR (101 MHz, CDCl$_3$) δ 171.75, 154.92, 140.37, 129.13, 128.35, 126.01, 79.99, 78.88, 73.17, 70.69, 52.89, 49.64, 34.63, 28.28, 19.51, 18.24, 18.19, 13.14; HRMS-ESI (m/z) [M+H]$^+$ calc'd for C$_{29}$H$_{49}$NO$_6$SiNa, 558.3221. found, 558.3224.

Example 2

Step 1: Preparation of tert-butyl N-[(3S,7S,8R,9S)-7-benzyl-9-methyl-2-oxo-8-triisopropylsilyloxy-1,5-dioxonan-3-yl]-N-tert-butoxycarbonylcarbamate (Compound 55)

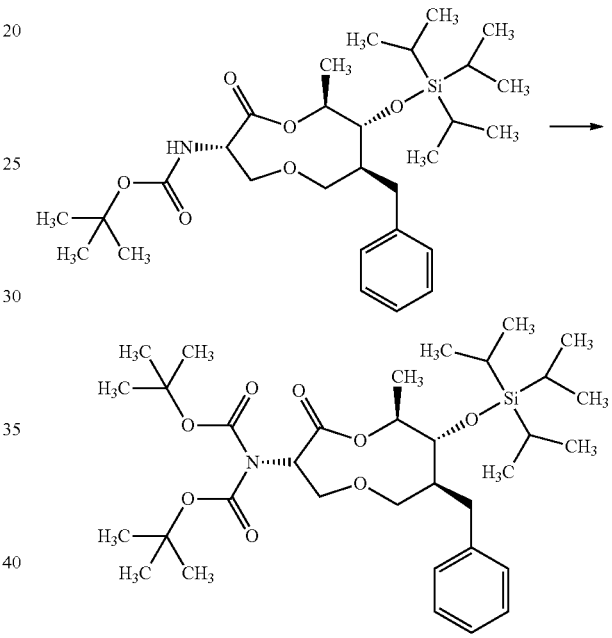

To a solution of tert-butyl ((3S,7S,8R,9S)-7-benzyl-9-methyl-2-oxo-8-((triisopropylsilyl)oxy)-1,5-dioxonan-3-yl)carbamate (5.00 g, 9.33 mmol, 1.00 equiv) in anhydrous CH$_3$CN (93 ml) were added DMAP (0.570 g, 4.67 mmol, 0.500 equiv) and di-tert-butyl dicarbonate (4.07 g, 18.7 mmol, 2.00 equiv) and the resulting solution was stirred overnight at room temperature. The orange solution was concentrated and purified directly by automated silica gel column chromatography (1-10% acetone in hexanes) to provide tert-butyl N-[(3S,7S,8R,9S)-7-benzyl-9-methyl-2-oxo-8-triisopropylsilyloxy-1,5-dioxonan-3-yl]-N-tert-butoxycarbonylcarbamate (5.78 g, 97%) as a sticky, colorless oil: IR (ATR) 2942, 2867, 1743, 1707, 1603, 1495, 1456, 1357, 1313, 1252, 1206, 1172, 1146, 1121, 1088, 1064, 1014, 945, 913, 882, 857, 835, 733, 700, 680 cm$^{-1}$; $^1$H NMR (400 MHz, CDCl$_3$) δ 7.28 (d, J=7.0 Hz, 2H), 7.25-7.17 (m, 2H), 5.14 (dd, J=7.0, 3.3 Hz, 1H), 5.00 (dd, J=9.2, 6.9 Hz, 1H), 4.07 (qd, J=11.6, 8.1 Hz, 2H), 3.92 (dd, J=6.0, 3.3 Hz, 1H), 3.73-3.64 (m, 1H), 3.64-3.54 (m, 1H), 2.90 (d, J=10.9 Hz, 1H), 2.87-2.76 (m, 1H), 2.04 (dd, J=11.0, 5.3 Hz, 1H), 1.54-1.46 (m, 21H), 1.43 (d, J=7.0 Hz, 4H), 1.06 (d, J=2.2 Hz, 18H); $^{13}$C NMR (101 MHz, CDCl$_3$) δ 169.50, 152.72, 140.67, 129.13, 128.31, 125.93, 82.88, 78.83, 72.71, 57.79, 49.97, 34.16, 28.28, 27.91, 19.67, 18.24, 18.18, 18.13, 13.14, 12.78; HRMS-ESI (m/z) [M+Na]+ calc'd for C34H57NNaO8Si; 658.3746. found, 658.3722.

Example 2

Step 2: Preparation of tert-butyl N-[(3S,7S,8R,9S)-7-benzyl-8-hydroxy-9-methyl-2-oxo-1,5-dioxonan-3-yl]-N-tert-butoxycarbonylcarbamate (Compound 57)

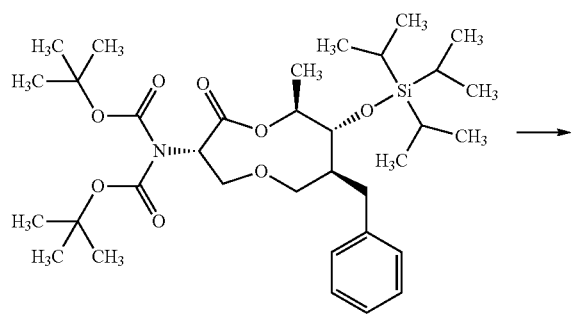

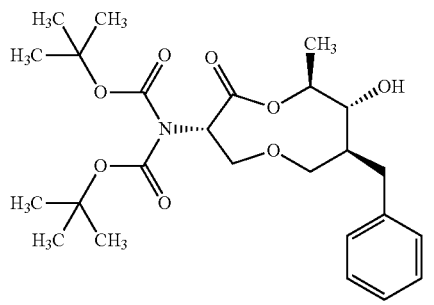

To a solution of tert-butyl N-[(3S,7S,8R,9S)-7-benzyl-9-methyl-2-oxo-8-triisopropylsilyloxy-1,5-dioxonan-3-yl]-N-tert-butoxycarbonylcarbamate (5.77 g, 9.07 mmol, 1.00 equiv) in THF (91 ml) was added tetrabutylammonium fluoride (TBAF; 1M in THF, 18 ml, 18 mmol, 2.0 equiv). The resulting solution was stirred at room temperature for 1.5 h, poured into 100 mL sat'd sodium chloride (NaCl), extracted with EtOAc (3×100 mL). The combined organic extracts were dried over MgSO4, filtered, and concentrated to provide an oil. Purification by automated silica gel column chromatography provided tert-butyl N-[(3S,7S,8R,9S)-7-benzyl-8-hydroxy-9-methyl-2-oxo-1,5-dioxonan-3-yl]-N-tert-butoxycarbonylcarbamate (3.15 g, 72.4%) as a solid white foam: IR (ATR) 3489, 2980, 2934, 1740, 1703, 1496, 1476, 1454, 1393, 1367, 1307, 1254, 1210, 1168, 1145, 1121, 1041, 909, 850, 729, 701 cm−1; 1H NMR (400 MHz, CDCl3) δ 7.31-7.27 (m, 2H), 7.23-7.16 (m, 3H), 5.21 (dd, J=8.8, 4.8 Hz, 1H), 5.06-4.91 (m, 1H), 4.16 (dd, J=12.1, 4.8 Hz, 1H), 3.89 (dd, J=12.1, 8.8 Hz, 1H), 3.77 (d, J=9.9 Hz, 1H), 3.55-3.42 (m, 2H), 3.00 (dd, J=13.8, 5.0 Hz, 1H), 2.57 (dd, J=13.8, 9.4 Hz, 1H), 2.26 (d, J=7.8 Hz, 1H), 2.10 (s, 1H), 1.50 (s, 18H), 1.47 (d, J=6.5 Hz, 3H); 13C NMR (101 MHz, CDCl3) δ 169.75, 152.71, 139.53, 129.10, 128.49, 126.28, 83.15, 77.20, 76.51, 71.67, 57.69, 47.63, 36.34, 27.95, 18.58; HRMS-ESI (m/z) [M+Na]+ calc'd for C25H37NNaO8; 502.2411 found 502.2418.

Example 2

Step 3: Preparation of tert-butyl N-[(3S,7S,8R,9S)-7-benzyl-9-methyl-8-(2-methylallyloxy)-2-oxo-1,5-dioxonan-3-yl]-N-tert-butoxycarbonylcarbamate (Compound 82)

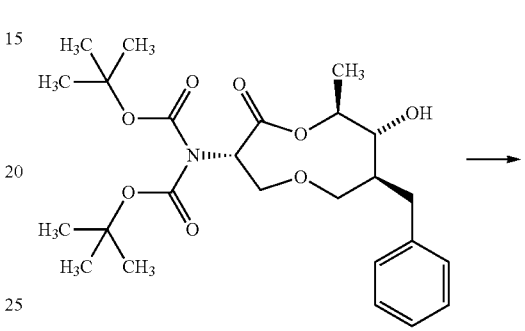

To a solution of tert-butyl N-[(3S,7S,8R,9S)-7-benzyl-8-hydroxy-9-methyl-2-oxo-1,5-dioxonan-3-yl]-N-tert-butoxycarbonylcarbamate (3.59 g, 7.49 mmol, 1.00 equiv) in THF (75 ml) was added tert-butyl (2-methylallyl) carbonate (2.58 g, 15.0 mmol, 2.00 equiv). This solution was degassed by placing under vacuum and backfilling with N2 (3×). To this solution were added dppf (0.830 g, 1.50 mmol, 0.200 equiv) and Pd2dba3 (0.686 g, 0.749 mmol, 0.100 equiv). The resulting dark solution was heated to 55° C. (external temp) for 1 h, and then cooled to room temperature. The solution was concentrated and purified by automated silica gel column chromatography (4-16% acetone in hexanes) to provide tert-butyl N-[(3S,7S,8R,9S)-7-benzyl-9-methyl-8-(2-methylallyloxy)-2-oxo-1,5-dioxonan-3-yl]-N-tert-butoxycarbonylcarbamate (3.68 g, 92%) as a white solid: 1H NMR (400 MHz, CDCl3) δ 7.32-7.22 (m, 2H), 7.22-7.12 (m, 3H), 5.12 (dd, J=8.5, 6.6 Hz, 1H), 5.07-4.98 (m, 1H), 4.98-4.83 (m, 2H), 4.15-4.02 (m, 2H), 3.95 (d, J=11.8 Hz, 1H), 3.86 (dd, J=11.8, 8.5 Hz, 1H), 3.52 (d, J=10.7 Hz, 1H), 3.40 (dd, J=10.9, 6.0 Hz, 1H), 3.23 (t, J=8.8 Hz, 1H), 3.11 (dd, J=13.6, 3.3 Hz, 1H), 2.40 (t, J=12.5 Hz, 1H), 2.01 (d, J=5.6 Hz, 1H), 1.77 (s, 3H), 1.54-1.39 (m, 21H); 13C NMR (101 MHz, CDCl3) δ 169.97, 152.62, 141.78, 140.01, 129.25, 128.33, 126.02, 112.13, 84.93, 83.01, 75.89, 75.20, 70.96, 57.44, 47.00, 35.02, 27.92, 19.79, 18.97; ESIMS (m/z) 556.8 ([M+Na]+).

Example 2

Step 4: Preparation of tert-butyl N-[(3S,7S,8R,9S)-7-benzyl-8-isobutoxy-9-methyl-2-oxo-1,5-dioxonan-3-yl]-N-tert-butoxycarbonylcarbamate (Compound 83)

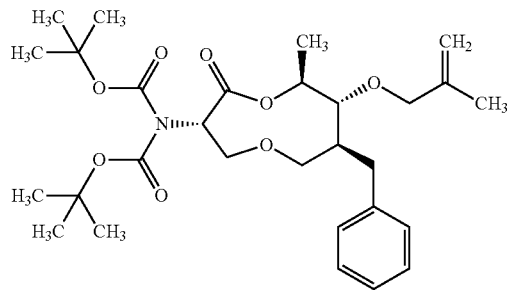

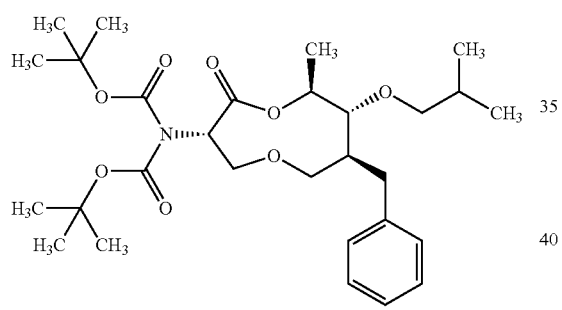

To a solution of tert-butyl N-[(3S,7S,8R,9S)-7-benzyl-9-methyl-8-(2-methylallyloxy)-2-oxo-1,5-dioxonan-3-yl]-N-tert-butoxycarbonylcarbamate (3.65 g, 6.84 mmol, 1.00 equiv) in EtOAc (68 ml) was added Pd/C (10%; 0.364 g, 0.342 mmol, 0.0500 equiv). The atmosphere was replaced with hydrogen (1 atm, balloon) and the mixture was stirred vigorously overnight. The reaction was filtered through a plug of Celite® and the plug was then flushed with EtOAc (100 mL). The filtrate was concentrated to give tert-butyl N-[(3S,7S,8R,9S)-7-benzyl-8-isobutoxy-9-methyl-2-oxo-1,5-dioxonan-3-yl]-N-tert-butoxycarbonylcarbamate (3.62 g, 99%) as a white, crystalline solid: IR (ATR) 2987, 2933, 2914, 2876, 1749, 1723, 1413, 1391, 1367, 1317, 1271, 1257, 1238, 1229, 1196, 1147, 1097, 1084, 1065, 1058, 854, 744 cm−1; 1H NMR (400 MHz, CDCl3) δ 3.33-3.27 (m, 1H), 3.40-3.33 (m, 1H), 1.92-1.79 (m, 1H), 7.35-7.22 (m, 2H), 7.22-7.11 (m, 3H), 5.11 (dd, J=8.5, 6.4 Hz, 1H), 4.88 (dq, J=9.0, 6.3 Hz, 1H), 3.46-3.40 (m, 1H), 4.07 (dd, J=11.8, 6.4 Hz, 1H), 3.84 (dd, J=11.8, 8.6 Hz, 1H), 3.52 (d, J=10.6 Hz, 1H), 3.18-3.08 (m, 2H), 2.35 (s, 1H), 1.98 (s, 1H), 1.48 (s, 21H), 0.94 (d, J=6.7 Hz, 6H); 13C NMR (101 MHz, CDCl3) δ 169.98, 152.62, 140.12, 129.25, 128.32, 125.99, 84.52, 82.99, 78.82, 75.39, 70.96, 57.47, 47.05, 34.98, 29.16, 27.92, 19.49, 18.95; HRMS-ESI (m/z) [M−H]− calc'd for C29H44NO8; 534.3072. found, 534.3069.

Example 2

Steps 5 and 6: Preparation of N-((3S,7S,8R,9S)-7-benzyl-8-isobutoxy-9-methyl-2-oxo-1,5-dioxonan-3-yl)-3-hydroxy-4-methoxypicolinamide (Compound 2)

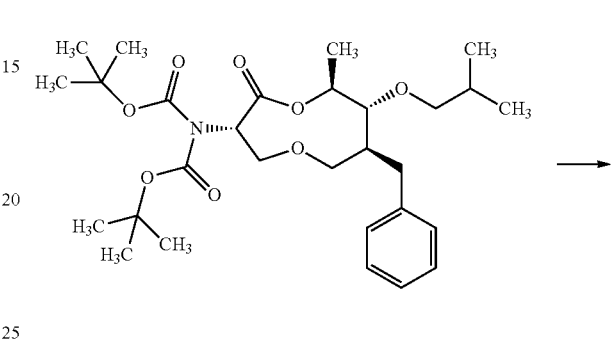

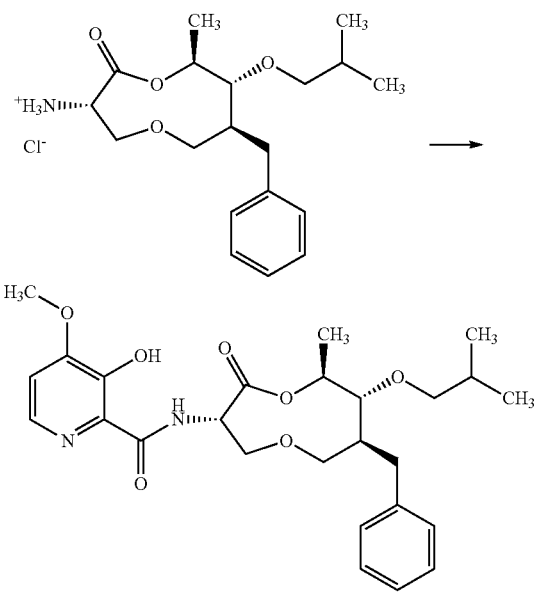

To a solution of tert-butyl N-[(3S,7S,8R,9S)-7-benzyl-8-isobutoxy-9-methyl-2-oxo-1,5-dioxonan-3-yl]-N-tert-butoxycarbonylcarbamate (3.586 g, 6.69 mmol) in CH2Cl2 (33 mL) was added HCl (4M in dioxane; 33.5 ml, 134 mmol, 20 equiv). This solution was stirred for 1 h and concentrated to furnish (3S,7S,8R,9S)-7-benzyl-8-isobutoxy-9-methyl-2-oxo-1,5-dioxonan-3-aminium chloride as a white solid. The solid was suspended in CH2Cl2 (66 mL), and N-methylmorpholine (4.42 ml, 40.2 mmol, 6.00 equiv) was added, causing dissolution of the solid. To this solution were added 3-hydroxy-4-methoxypicolinic acid (1.70 g, 10.0 mmol, 1.50 equiv) and HATU (4.07 g, 10.71 mmol, 1.60 equiv). The resulting suspension was stirred at room temperature for 20 h, concentrated, and purified by automated silica gel column chromatography (2-12% acetone in CH2Cl2) to yield N-((3S, 7S,8R,9S)-7-benzyl-8-isobutoxy-9-methyl-2-oxo-1,5-dioxonan-3-yl)-3-hydroxy-4-methoxypicolinamide (2.08 g, 63.9%) as a yellow oil.

Example 2

Step 7: Preparation of (2-((3S,7S,8R,9S)-7-benzyl-8-isobutoxy-9-methyl-2-oxo-1,5-dioxonan-3-ylcarbamoyl)-4-methoxypyridin-3-yloxy)methyl acetate (Compound 8)

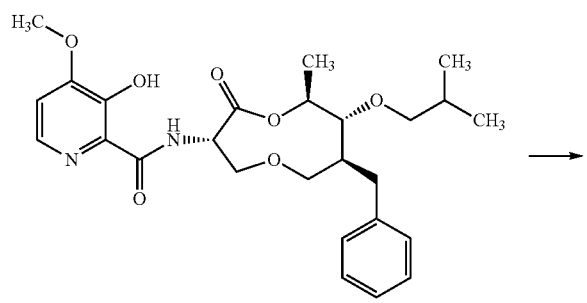

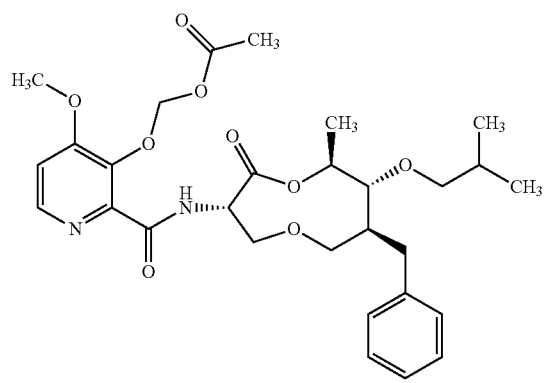

Bromomethyl acetate (48 uL, 0.49 mmol) was added to a suspension of N-((3S,7S,8R,9S)-7-benzyl-8-isobutoxy-9-methyl-2-oxo-1,5-dioxonan-3-yl)-3-hydroxy-4-methoxypicolinamide (160 mg, 0.33 mmol), sodium iodide (NaI, 2.5 mg, 0.02 mmol) and sodium carbonate (Na$_2$CO$_3$; 56 mg, 0.53 mmol) in acetone (3 mL). The mixture was heated to 50° C. and stirred overnight. The suspension was diluted with acetone and filtered. The yellow solution was concentrated and purified by flash chromatography (50% EtOAc in hexanes) to furnish the product as a white foam (97 mg, 53%): IR (film) 3370, 3025, 2957, 2874, 1752, 1677 cm$^{-1}$; $^1$H NMR (400 MHz, CDCl$_3$) δ 8.39 (d, J=8.2 Hz, 1H), 8.27 (d, J=5.4 Hz, 1H), 7.34-7.23 (m, 2H), 7.20 (dd, J=7.2, 4.8 Hz, 3H), 6.95 (d, J=5.4 Hz, 1H), 5.80-5.64 (m, 2H), 5.13-4.92 (m, 2H), 4.02 (dd, J=11.7, 7.4 Hz, 1H), 3.90 (s, 3H), 3.54-3.28 (m, 5H), 3.14 (dd, J=11.7, 6.4 Hz, 2H), 2.40-2.23 (m, 1H), 2.06 (s, 3H), 2.01-1.82 (m, 2H), 1.50 (d, J=6.4 Hz, 3H), 0.93 (d, J=6.7 Hz, 6H); $^{13}$C NMR (101 MHz, CDCl$_3$) δ 171.81, 170.31, 163.18, 160.20, 145.79, 143.93, 142.15, 140.02, 129.21 (2), 128.44 (2), 126.10, 109.69, 89.41, 84.58, 79.26, 75.74, 72.34, 72.16, 56.19, 51.81, 47.45, 35.09, 29.19, 20.88, 19.50 (2), 18.83; ESIMS m/z 560.36 ([M+H]$^+$).

Example 3

Step 1: Preparation of tert-butyl N-[(3S,7S,8R,9S)-7-benzyl-8-methoxy-9-methyl-2-oxo-1,5-dioxonan-3-yl]-N-tert-butoxycarbonylcarbamate (Compound 74)

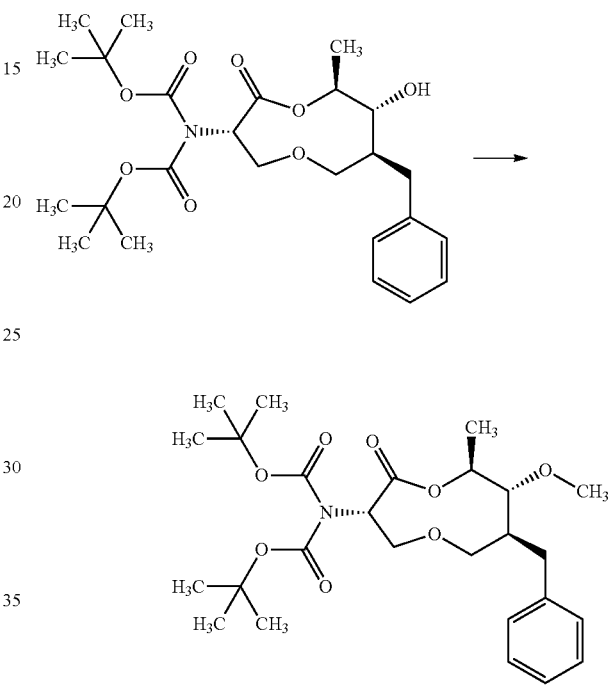

To a solution of tert-butyl N-[(3S,7S,8R,9S)-7-benzyl-8-hydroxy-9-methyl-2-oxo-1,5-dioxonan-3-yl]-N-tert-butoxycarbonylcarbamate (250 mg, 0.521 mmol, 1.00 equiv) in CH$_2$Cl$_2$ (5.2 mL, 0.1 M) at 0° C. (ice water bath) were added proton sponge (335 mg, 1.56 mmol, 3.00 equiv) and trimethyloxonium tetrafluoroborate (116 mg, 0.782 mmol, 1.50 equiv). The resulting white suspension was stirred at 0° C. for 30 minutes (min), removed from the cold bath and stirred at room temperature for 5 h, and then poured into ½ sat'd NaHCO$_3$ solution (20 mL). The mixture was extracted with CH$_2$Cl$_2$ (3×20 mL), and the combined organic phases were washed with 1N HCl (20 mL), dried over Na$_2$SO$_4$, filtered, and concentrated to provide an oil. Purification by automated silica gel column chromatography provided tert-butyl N-[(3S,7S,8R,9S)-7-benzyl-8-methoxy-9-methyl-2-oxo-1,5-dioxonan-3-yl]-N-tert-butoxycarbonylcarbamate (220 mg, 85%) as a colorless, sticky solid: IR (ATR) 2979, 2935, 2831, 1742, 1706, 1455, 1293, 1254, 1170, 1144, 1121, 1098, 1057, 913, 853, 732 cm$^{-1}$; $^1$H NMR (400 MHz, CDCl$_3$) δ 7.32-7.24 (m, 2H), 7.22-7.15 (dd, J=5.1, 2.6 Hz, 3H), 5.18-5.06 (dd, J=8.6, 6.3 Hz, 1H), 4.94-4.79 (dq, J=9.1, 6.3 Hz, 1H), 4.16-4.01 (dd, J=11.8, 6.3 Hz, 1H), 3.94-3.76 (dd, J=11.8, 8.7 Hz, 1H), 3.59-3.50 (d, J=10.5 Hz, 1H), 3.50-3.45 (s, 3H), 1.50-1.45 (m, 21H), 3.42-3.32 (dd, J=10.8, 6.2 Hz, 1H), 3.14-3.01 (m, 2H), 2.47-2.31 (t, J=12.4 Hz, 1H), 2.08-1.89 (s, 1H), 1.53-1.43 (s, 18H); $^{13}$C NMR (101 MHz, CDCl$_3$) δ 169.94, 152.62, 139.87, 129.25, 128.33, 126.03, 86.42, 83.03, 75.09, 70.91, 59.58, 57.42, 46.62, 35.15, 27.92, 18.92; HRMS-ESI (m/z) [M+Na]+ calc'd for $C_{26}H_{39}NO_8Na$, 516.2568. found, 516.2572.

Example 4

Step 1: Preparation of tert-Butyl-(3S,7S,8R,9S)-7-benzyl-8-hydroxy-9-methyl-2-oxo-1,5-dioxonan-3-ylcarbamate (Compound 48)

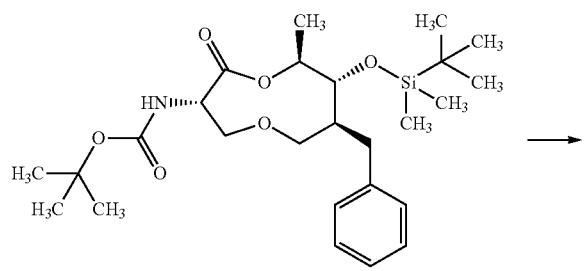

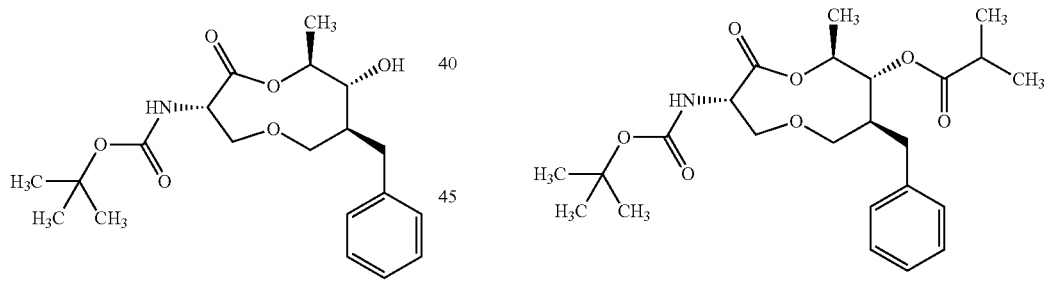

A solution of tert-butyl ((3S,7S,8R,9S)-7-benzyl-8-((tert-butyldimethylsilyl)oxy)-9-methyl-2-oxo-1,5-dioxonan-3-yl)carbamate (120 mg, 0.24 mmol) in a solution of HF/pyridine/THF (5:3:8 ratio, 1.2 mL) was stirred at room temperature. After 16 h, an additional 0.1 mL HF-pyridine solution was added and the reaction was allowed to stir for 2 h. The crude reaction was diluted with EtOAc (5 mL) and added to sat'd aq $Na_2CO_3$ (5 mL) dropwise. Additional sat'd aq $Na_2CO_3$ was added until bubbling was no longer observed. The EtOAc layer was separated and the aqueous phase was extracted with EtOAc (2×). The combined organic layers were dried over $Na_2SO_4$, filtered, and concentrated to furnish tert-butyl-(3S,7S,8R,9S)-7-benzyl-8-hydroxy-9-methyl-2-oxo-1,5-dioxonan-3-ylcarbamate as a colorless oil (82 mg, 89%): $^1$H NMR (400 MHz, $CDCl_3$) δ 7.32-7.26 (m, 3H), 7.20 (dd, J=8.2, 6.4 Hz, 2H), 5.15 (d, J=8.5 Hz, 1H), 4.88 (m, 1H), 4.65 (d, J=7.6 Hz, 1H), 3.90 (dd, J=11.7, 7.5 Hz, 1H), 3.57 (d, J=10.3 Hz, 1H), 3.44 (m, 2H), 3.33 (m, 1H), 3.11 (dd, J=13.8, 4.3 Hz, 1H), 2.49 (m, 1H), 1.87 (s, 1H), 1.48 (d, J=6.4 Hz, 3H), 1.43 (d, J=4.3 Hz, 9H); ESIMS m/z 378.4 ([M−H]).

Example 4

Step 2: Preparation of (3S,6S,7R,8S)-8-benzyl-3-(tert-butoxycarbonylamino)-6-methyl-4-oxo-1,5-dioxonan-7-yl isobutyrate (Compound 104)

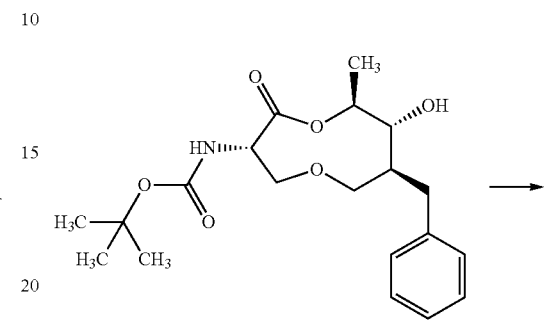

To a solution of tert-butyl-(3S,7S,8R,9S)-7-benzyl-8-hydroxy-9-methyl-2-oxo-1,5-dioxonan-3-ylcarbamate (72 mg, 0.19 mmol) in pyridine (1 mL) at 0° C. was added isobutyryl chloride (80 μL, 0.76 mmol) and the solution was stirred at 0° C. for 2 h. The crude reaction mixture was warmed to room temperature, water (1 mL) was added, and the solution was stirred for 30 min. The reaction mixture was extracted with $Et_2O$ (3×) and the combined organic extracts were dried over $Na_2SO_4$, filtered, and concentrated. The crude product was purified by flash chromatography (silica gel, 20% EtOAc/hexanes, TLC $R_f$=0.5) to furnish (3S,6S,7R,8S)-8-benzyl-3-(tert-butoxycarbonylamino)-6-methyl-4-oxo-1,5-dioxonan-7-yl isobutyrate as a white foam (45 mg, 53%): $^1$H NMR (400 MHz, $CDCl_3$) δ 7.31-7.11 (m, 5H), 5.14 (d, J=8.0 Hz, 1H), 5.03 (m, 1H), 4.94 (t, J=9.2 Hz, 1H), 4.66 (d, J=7.7 Hz, 1H), 3.89 (dd, J=11.7, 7.2 Hz, 1H), 3.56 (d, J=10.7 Hz, 1H), 3.46 (m, 1H), 3.35 (dd, J=11.4, 6.8 Hz, 1H), 2.71 (dd, J=13.9, 3.6 Hz, 1H), 2.58 (dt, J=13.9, 7.0 Hz, 1H), 2.25 (t, J=12.6 Hz, 1H), 2.04 (s, 1H), 1.43 (s, 9H), 1.32 (d, J=6.2 Hz, 3H), 1.21 (dd, J=7.0, 0.9 Hz, 6H); ESIMS m/z 471.9 ([M+Na]¹).

Example 5

Step 1: Preparation of (E)-methyl 3-(((3S,6S,7R,8S)-8-benzyl-3-((tert-butoxycarbonyl)amino)-6-methyl-4-oxo-1,5-dioxonan-7-yl)oxy)acrylate (Compound 49)

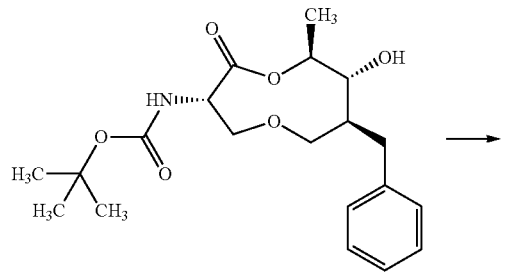

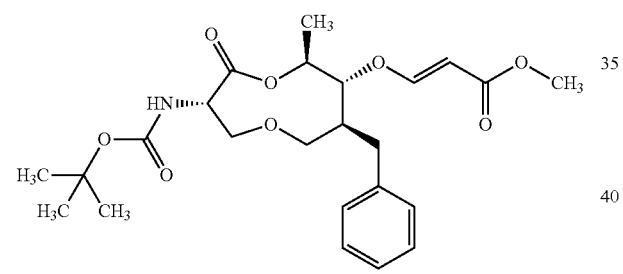

To a solution of tert-butyl ((3S,7S,8R,9S)-7-benzyl-8-hydroxy-9-methyl-2-oxo⁻¹,5-dioxonan-3-yl)carbamate (280 mg, 0.738 mmol, 1.00 equiv) in CH$_2$Cl$_2$ (7.4 mL) were added methyl propiolate (0.098 mL, 1.11 mmol, 1.50 equiv) and DABCO (4 mg, 0.04 mmol, 0.05 equiv). This solution was stirred at room temperature for 1 h, concentrated, and purified by automated silica gel column chromatography (5-25% acetone in hexanes) to provide (E)-methyl 3-(((3S,6S,7R,8S)-8-benzyl-3-((tert-butoxycarbonyl)amino)-6-methyl-4-oxo-1,5-dioxonan-7-yl)oxy)acrylate (312 mg, 91%) as a white solid: mp slow melt from 50-80° C., recrystallized at 98° C., remelt at 128-129° C.; IR (neat film) 3342, 2980, 2949, 1753, 1703, 1639, 1497, 1329, 1132, 910, 731 cm⁻¹; ¹H NMR (400 MHz, CDCl$_3$) δ 7.48 (d, J=12.2 Hz, 1H), 7.32-7.27 (m, 2H), 7.23-7.18 (m, 1H), 7.15-7.11 (m, 2H), 5.40 (d, J=12.2 Hz, 1H), 5.10 (d, J=8.3 Hz, 1H), 5.02 (dd, J=9.3, 6.4 Hz, 1H), 4.64 (dd, J=15.3, 7.5 Hz, 1H), 3.92 (dd, J=11.6, 7.6 Hz, 1H), 3.74 (d, J=9.1 Hz, 1H), 3.71 (s, 3H), 3.51 (d, J=11.1 Hz, 1H), 3.43 (dd, J=10.5, 6.4 Hz, 1H), 3.29 (dd, J=11.3, 7.5 Hz, 1H), 2.92 (dd, J=13.8, 3.5 Hz, 1H), 2.34 (t, J=12.5 Hz, 1H), 2.06 (s, 1H), 1.42 (s, 9H), 1.41 (d, J=6.5 Hz, 3H); ¹³C NMR (100 MHz, CDCl$_3$) δ 172.16, 167.97, 162.94, 154.91, 138.54, 129.09, 128.57, 126.48, 98.50, 89.01, 80.31, 73.94, 72.57, 71.33, 52.70, 51.26, 46.47, 35.18, 28.25, 18.73; HRMS-ESI (m/z) [M+Na]⁺ calc'd for C$_{24}$H$_{33}$NO$_8$Na, 486.2098. found, 486.2104.

Example 5

Step 2: Preparation of methyl 3-(((3S,6S,7R,8S)-8-benzyl-3-((tert-butoxycarbonyl)amino)-6-methyl-4-oxo-1,5-dioxonan-7-yl)oxy)propanoate (Compound 50)

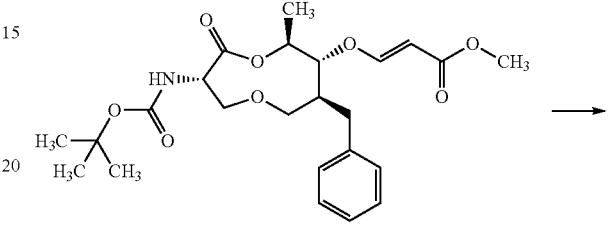

To a solution of (E)-methyl 3-((3S,6S,7R,8S)-8-benzyl-3-(tert-butoxycarbonylamino)-6-methyl-4-oxo-1,5-dioxonan-7-yloxy)acrylate (168 mg, 0.362 mmol, 1.00 equiv) in EtOAc (3.6 mL, 0.1 M) was added 10% Pd/C (19 mg, 0.018 mmol, 0.050 equiv). The flask was equipped with a rubber septum and the atmosphere was replaced with H$_2$ via needle-equipped balloon. After 17 h at room temperature, the catalyst was removed by filtration through Celite® and the pad was flushed with EtOAc. The filtrate was concentrated to provide methyl 3-((3S,6S,7R,8S)-8-benzyl-3-(tert-butoxycarbonylamino)-6-methyl-4-oxo-1,5-dioxonan-7-yloxy)propanoate (163 mg, 97%) as a clear, colorless film: IR (neat film) 3357, 3026, 2978, 2880, 1741, 1711, 1497, 1367, 1294, 1198, 1163, 1070, 1023, 911, 731 cm⁻¹; ¹H NMR (400 MHz, CDCl$_3$) δ 7.34-7.27 (m, 2H), 7.24-7.10 (m, 3H), 5.18-5.03 (d, J=8.3 Hz, 1H), 5.01-4.81 (dq, J=9.2, 6.4 Hz, 1H), 4.69-4.47 (q, J=7.3 Hz, 1H), 4.07-3.76 (m, 3H), 3.75-3.61 (s, 3H), 3.53-3.31 (m, 2H), 3.31-3.03 (m, 3H), 2.71-2.52 (t, J=6.2 Hz, 2H), 2.41-2.22 (t, J=12.6 Hz, 1H), 1.98-1.75 (s, 1H), 1.53-1.46 (d, J=6.4 Hz, 3H), 1.46-1.36 (s, 9H); ¹³C NMR (100 MHz, CDCl$_3$) δ 172.23, 171.73, 139.78, 129.15, 128.44, 126.14, 85.23, 80.11, 75.32, 72.86, 72.28, 67.67, 52.91, 51.82, 47.16, 35.24, 35.05, 28.26, 18.68; HRMS-ESI (m/z) [M+Na]$^+$ calc'd for C$_{24}$H$_{35}$NO$_8$Na, 488.2255. found, 488.2260.

Example 6

Step 1: Preparation of (E)-benzyl 3-(((3S,6S,7R,8S)-8-benzyl-3-((tert-butoxycarbonyl)amino)-6-methyl-4-oxo-1,5-dioxonan-7-yl)oxy)acrylate (Compound 51)

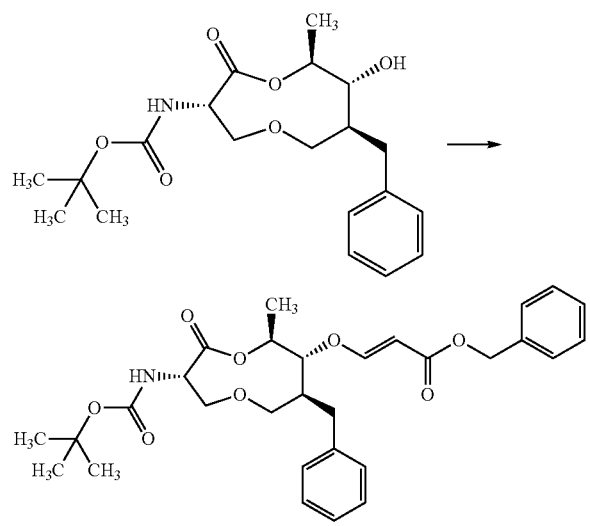

extracts were dried over Na$_2$SO$_4$, filtered, and concentrated to provide a white crystalline solid. The solid was purified by automated silica gel column chromatography (5-25% acetone in hexanes) to provide (E)-benzyl 3-(((3S,6S,7R,8S)-8-benzyl-3-((tert-butoxycarbonyl)amino)-6-methyl-4-oxo-1,5-dioxonan-7-yl)oxy)acrylate (490 mg, 96%) as a white solid: IR (ATR) 3344, 2982, 2941, 1752, 1717, 1690, 1638, 1527, 1454, 1381, 1205, 1079, 833, 751, 697 cm$^{-1}$; $^1$H NMR (400 MHz, CDCl$_3$) δ 7.50 (d, J=12.2 Hz, 1H), 7.40-7.09 (m, 10H), 5.44 (d, J=12.2 Hz, 1H), 5.16 (s, 2H), 5.09 (d, J=8.2 Hz, 1H), 5.01 (dd, J=9.3, 6.4 Hz, 1H), 4.64 (dd, J=15.3, 7.5 Hz, 1H), 3.91 (dd, J=11.6, 7.5 Hz, 1H), 3.73 (t, J=9.2 Hz, 1H), 3.45 (dt, J=10.6, 8.5 Hz, 2H), 3.28 (dd, J=11.3, 7.5 Hz, 1H), 2.92 (dd, J=13.8, 3.5 Hz, 1H), 2.34 (t, J=12.4 Hz, 1H), 2.05 (s, 1H), 1.51-1.35 (m, 12H); $^{13}$C NMR (100 MHz, CDCl$_3$) δ 172.15, 167.40, 163.21, 138.54, 136.22, 129.10, 128.57, 128.25, 128.19, 126.48, 98.54, 89.01, 80.31, 73.94, 72.60, 71.36, 65.87, 52.72, 46.48, 35.21, 28.26, 18.74; HRMS-ESI (m/z) [M+Na]$^+$ calc'd for C$_{30}$H$_{37}$NO$_8$Na, 562.2411. found, 562.2427.

Example 6

Step 2: Preparation of 3-(((3S,6S,7R,8S)-8-benzyl-3-((tert-butoxycarbonyl)amino)-6-methyl-4-oxo-1,5-dioxonan-7-yl)oxy)propanoic acid (Compound 52)

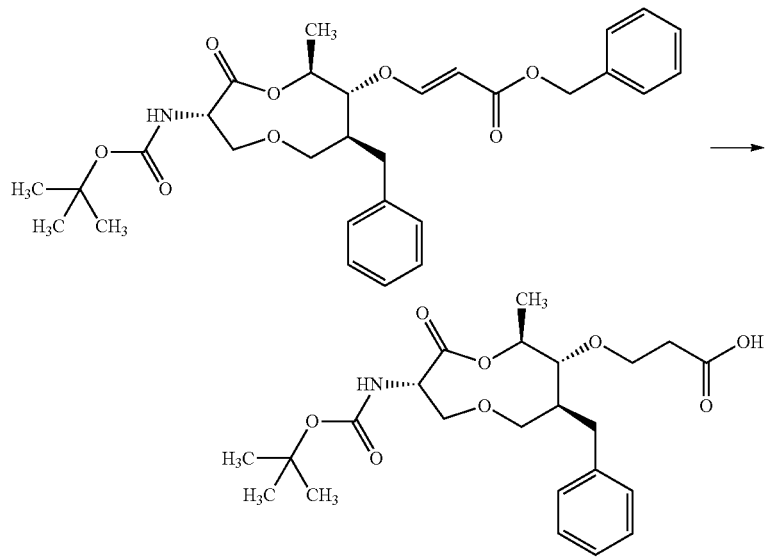

To a solution of tert-butyl ((3S,7S,8R,9S)-7-benzyl-8-hydroxy-9-methyl-2-oxo-1,5-dioxonan-3-yl)carbamate (360 mg, 0.949 mmol, 1.00 equiv) in CH$_2$Cl$_2$ (9.5 mL, 0.1 M) at 0° C. (ice water bath) were added benzyl propiolate (228 mg, 1.42 mmol, 1.5 equiv) and DABCO (5 mg, 0.05 mmol, 0.05 equiv). The resulting solution was stirred at 0° C. for 20 min and then poured into 0.1 N HCl (20 mL). The mixture was extracted with CH$_2$Cl$_2$ (3×20 mL), and the combined organic A suspension of (E)-benzyl 3-(((3S,6S,7R,8S)-8-benzyl-3-((tert-butoxycarbonyl)amino)-6-methyl-4-oxo-1,5-dioxonan-7-yl)oxy)acrylate (490 mg, 0.908 mmol, 1.00 equiv) and 10% Pd/C (48 mg, 0.045 mmol, 0.05 equiv) in EtOAc (9.1 mL, 0.1 M) was stirred for 16 h under an atmosphere of H$_2$ (1 atm, balloon pressure) at room temperature. The reaction mixture was filtered through a plug of Celite® and the plug was washed with EtOAc (50 mL). The filtrate was concentrated to provide a white solid that was shown to be a mixture of partially reduced products by $^1$H NMR. This material was resubjected to the reaction conditions and isolated as before to provide 3-(((3S,6S,7R,8S)-8-benzyl-3-((tert-butoxycarbonyl)amino)-6-methyl-4-oxo-1,5-dioxonan-7-yl)oxy)propanoic acid (425 mg, 104%) as a white solid, contaminated with a small amount of EtOAc: IR (ATR) 3319, 2977, 2930, 2879, 1710, 1497, 1391, 1368, 1246, 1201, 1161, 1065, 851, 750 cm$^{-1}$; $^1$H NMR (400 MHz, CDCl$_3$) δ 7.31-7.22 (m, 2H), 7.22-7.12 (m, 3H), 5.14 (d, J=8.2 Hz, 1H), 4.93 (dq, J=9.0, 6.4 Hz, 1H), 4.59 (dd, J=15.2, 7.4 Hz, 1H), 3.99-3.84 (m, 2H), 3.79 (dt, J=8.9, 6.1 Hz, 1H), 3.48-3.31 (m, 2H), 3.24 (dd, J=11.2, 7.5 Hz, 1H), 3.16 (t, J=9.0 Hz, 1H), 3.12-3.06 (m, 1H), 2.60 (t, J=6.1 Hz, 2H), 2.32 (t, J=12.6 Hz, 1H), 1.90 (s, 1H), 1.48 (d, J=6.4 Hz, 3H), 1.42 (s, 9H); $^{13}$C NMR (100 MHz, CDCl$_3$) δ 176.37, 172.28, 154.99, 139.74, 129.16, 128.42, 126.13, 85.30, 80.17, 75.27, 72.78, 72.16, 67.35, 52.88, 47.20, 35.09, 28.27, 18.71; HRMS-ESI (m/z) [M+Na]$^+$ calc'd for C$_{23}$H$_{33}$NO$_8$Na, 474.2098. found, 474.2118.

Example 6

Step 3: Preparation of tert-butyl ((3S,7S,8R,9S)-7-benzyl-8-(3-hydroxypropoxy)-9-methyl-2-oxo-1,5-dioxonan-3-yl)carbamate (Compound 63)

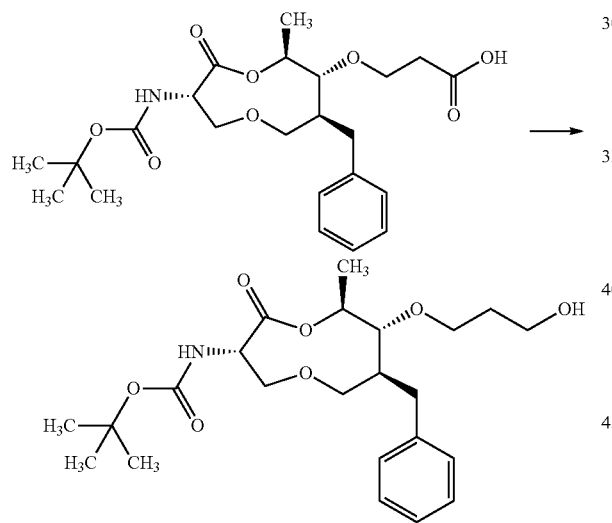

To a solution of 3-(((3S,6S,7R,8S)-8-benzyl-3-((tert-butoxycarbonyl)amino)-6-methyl-4-oxo-1,5-dioxonan-7-yl)oxy)propanoic acid (162 mg, 0.359 mmol, 1.00 equiv) in THF (3.6 mL, 0.1 M) at 0° C. (ice water bath) was added a 1 M solution of borane tetrahydrofuran complex in THF (0.897 mL, 0.897 mmol, 2.5 equiv). The resulting colorless solution was stirred at 0° C. for 4 h, quenched with 1 N HCl (3 mL), poured into H$_2$O (20 mL), and extracted with EtOAc (3×20 mL). The combined organic extracts were dried over MgSO$_4$, filtered, and concentrated to provide a film. The crude film was purified by automated silica gel column chromatography (5-75% acetone in hexanes) to yield tert-butyl ((3S,7S,8R, 9S)-7-benzyl-8-(3-hydroxypropoxy)-9-methyl-2-oxo-1,5-dioxonan-3-yl)carbamate (121 mg, 77%) as an oily white solid: IR (ATR) 3365, 2927, 2874, 1747, 1695, 1496, 1454, 1367, 1295, 1202, 1071, 853, 746 cm$^{-1}$; $^1$H NMR (400 MHz, CDCl$_3$) δ 7.35-7.12 (m, 5H), 5.17 (d, J=8.3 Hz, 1H), 4.98 (dq, J=8.6, 6.4 Hz, 1H), 4.60 (q, J=7.5 Hz, 1H), 3.96-3.83 (m, 2H), 3.83-3.75 (m, 2H), 3.71 (dt, J=8.8, 5.8 Hz, 1H), 3.49-3.37 (m, 2H), 3.26 (dd, J=11.4, 7.4 Hz, 1H), 3.16 (t, J=8.7 Hz, 1H), 3.09 (dd, J=13.6, 3.5 Hz, 1H), 2.38 (t, J=12.5 Hz, 1H), 2.13 (d, J=13.0 Hz, 1H), 1.91 (d, J=16.2 Hz, 1H), 1.86 (p, J=5.8 Hz, 2H), 1.50 (d, J=6.4 Hz, 3H), 1.42 (s, 9H); $^{13}$C NMR (100 MHz, CDCl$_3$) δ 172.27, 154.99, 139.66, 129.13, 128.49, 126.22, 99.99, 85.31, 80.12, 77.22, 75.10, 72.86, 72.11, 71.09, 61.25, 52.89, 47.30, 35.14, 32.59, 28.27, 18.76; HRMS-ESI (m/z) [M+Na]$^+$ calc'd for C$_{23}$H$_{35}$NO$_7$Na, 460.2306. found, 460.2320.

Example 6

Step 4: Preparation of tert-butyl ((3S,7S,8R,9S)-7-benzyl-8-(3-methoxypropoxy)-9-methyl-2-oxo-1,5-dioxonan-3-yl)carbamate (Compound 54)

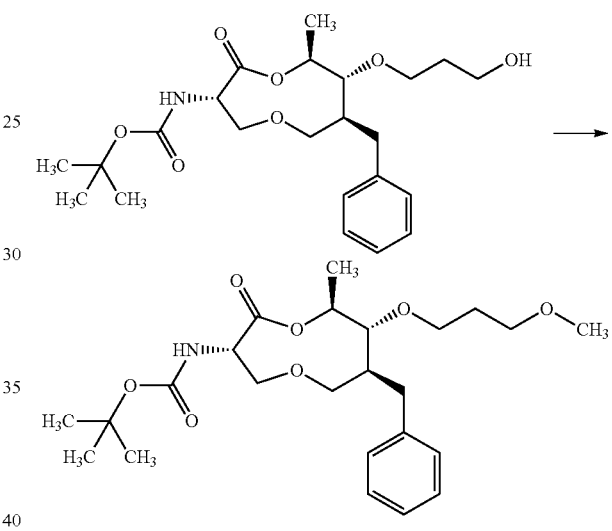

To a solution of tert-butyl ((3S,7S,8R,9S)-7-benzyl-8-(3-hydroxypropoxy)-9-methyl-2-oxo-1,5-dioxonan-3-yl)carbamate (118 mg, 0.270 mmol, 1.00 equiv) in CH$_2$Cl$_2$ (2.7 mL, 0.1 M) were added Proton Sponge™ (87 mg, 0.41 mmol, 1.5 equiv) and trimethyloxonium tetrafluoroborate (44 mg, 0.30 mmol, 1.1 equiv). A white precipitate quickly formed. The resulting mixture was stirred at room temperature for 16 h, quenched with 1 N HCl (2 mL), diluted with H$_2$O (20 mL), and extracted with CH$_2$Cl$_2$ (3×20 mL). The combined organic extracts were dried over Na$_2$SO$_4$, filtered, and concentrated to provide a white solid. Purification by automated silica gel column chromatography (4-30% acetone in hexanes) provided tert-butyl ((3S,7S,8R,9S)-7-benzyl-8-(3-methoxypropoxy)-9-methyl-2-oxo-1,5-dioxonan-3-yl)carbamate (118 mg, 72%) as a colorless oil: IR (ATR) 3347, 2978, 2928, 2875, 1750, 1710, 1496, 1354, 1367, 1385, 1327, 1163, 1088, 910, 855, 731 cm$^{-1}$; $^1$H NMR (400 MHz, CDCl$_3$) δ 7.28 (dd, J=8.6, 6.9 Hz, 2H), 7.24-7.14 (m, 3H), 5.13 (d, J=8.1 Hz, 1H), 4.94 (dq, J=9.3, 6.4 Hz, 1H), 4.60 (dd, J=14.9, 7.3 Hz, 1H), 3.88 (dd, J=11.5, 7.3 Hz, 1H), 3.76 (dt, J=12.7, 6.3 Hz, 1H), 3.63 (dt, J=8.7, 6.3 Hz, 1H), 3.53-3.42 (m, 3H), 3.41-3.33 (m, 1H), 3.30 (s, 4H), 3.28-3.22 (m, 1H), 3.18-3.05 (m, 2H), 2.29 (t, J=12.7 Hz, 1H), 1.98-1.89 (m, 1H), 1.86 (p, J=6.2 Hz, 2H), 1.48 (d, J=6.4 Hz, 3H), 1.42 (s, 10H); $^{13}$C NMR (100 MHz, CDCl$_3$) δ 172.24, 154.98, 139.94, 129.15, 128.43, 126.11, 84.99, 80.09, 75.51, 72.94, 72.51, 69.18, 58.64, 52.99, 47.23, 35.05, 30.47, 28.27, 18.70; HRMS-ESI (m/z) [M+Na]$^+$ calc'd for C$_{24}$H$_{37}$NO$_7$Na, 474.2462. found, 474.2467.

Example 7

Step 1: Preparation of tert-butyl ((3S,7S,8R,9S)-7-benzyl-8-(3-(dimethylamino)-3-oxopropoxy)-9-methyl-2-oxo-1,5-dioxonan-3-yl)carbamate (Compound 53)

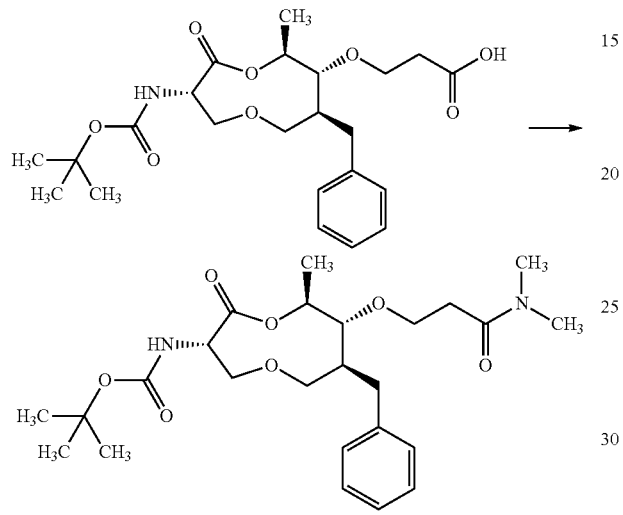

A solution of 3-(((3S,6S,7R,8S)-8-benzyl-3-((tert-butoxycarbonyl)amino)-6-methyl-4-oxo-1,5-dioxonan-7-yl)oxy)propanoic acid (250 mg, 0.554 mmol, 1.00 equiv), Hünig's base (0.484 mL, 2.77 mmol, 5.00 equiv), hydroxybenzotriazole (HOBT; 85 mg, 0.55 mmol, 1.00 equiv), and 1-ethyl-3-(3-dimethylaminopropyl)carbodiimide (EDC; 159 mg, 0.831 mmol, 1.50 equiv) in N,N-dimethylformamide (DMF; 5.5 mL, 0.1 M) were stirred at room temperature for 10 min, and then dimethylamine hydrochloride (54 mg, 0.66 mmol, 1.2 equiv) was added. The resulting solution was stirred at room temperature for 3 days (d). The reaction was diluted with EtOAc (20 mL) and washed with ½ sat'd NaCl (20 mL), and the phases separated. The aqueous phase was extracted with EtOAc (10 mL), and the combined organic extracts were dried over MgSO$_4$, filtered, and concentrated to provide a yellow oil. The product was purified by automated silica gel column chromatography (5-35% acetone in hexanes) to provide an oily solid that by TLC still had a large amount of DMF. The oily solid was taken up in 20 mL EtOAc and washed with ½ sat'd NaCl (2×10 mL), dried over MgSO$_4$, filtered and concentrated to provide tert-butyl ((3S,7S,8R, 9S)-7-benzyl-8-(3-(dimethylamino)-3-oxopropoxy)-9-methyl-2-oxo-1,5-dioxonan-3-yl)carbamate (208 mg, 78%) as an off-white solid: mp 142-143° C.; $^1$H NMR (400 MHz, CDCl$_3$) δ 7.32-7.27 (m, 2H), 7.23-7.14 (m, 3H), 5.12 (d, J=7.6 Hz, 1H), 4.94 (dq, J=9.2, 6.3 Hz, 1H), 4.60 (d, J=7.4 Hz, 1H), 4.02 (dd, J=15.5, 6.8 Hz, 1H), 3.93-3.81 (m, 2H), 3.49 (d, J=10.8 Hz, 1H), 3.42-3.33 (m, 1H), 3.34-3.25 (m, 1H), 3.21-3.08 (m, 2H), 3.02 (s, 3H), 2.94 (s, 3H), 2.71-2.51 (m, 2H), 2.31 (t, J=12.7 Hz, 1H), 1.92 (s, 1H), 1.50 (d, J=6.4 Hz, 3H), 1.42 (s, 9H); $^{13}$C NMR (100 MHz, CDCl$_3$) δ 172.15, 170.50, 154.97, 139.88, 129.11, 128.42, 126.09, 85.45, 80.09, 77.22, 75.43, 73.11, 72.81, 68.77, 53.07, 47.17, 37.35, 35.37, 35.12, 33.77, 28.26, 18.77; HRMS-ESI (m/z) [M+H]$^+$ calc'd for C$_{25}$H$_{39}$N$_2$O$_7$, 480.2784. found, 480.2785.

Example 8

Step 1: Preparation of tert-butyl ((3S,7S,8R,9S)-7-benzyl-9-methyl-2-oxo-8-(((E)-3-oxobut-1-en-1-yl)oxy)-1,5-dioxonan-3-yl)carbamate (Compound 64)

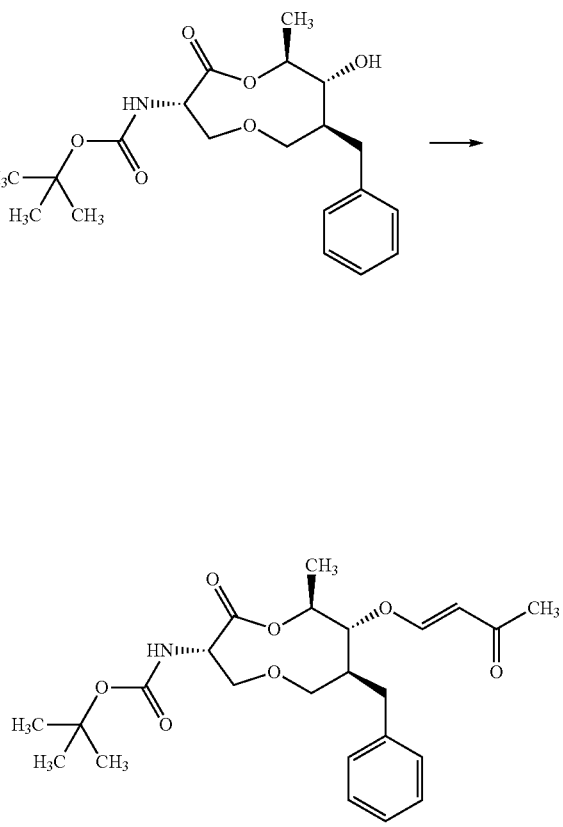

To a solution of tert-butyl ((3S,7S,8R,9S)-7-benzyl-8-hydroxy-9-methyl-2-oxo-1,5-dioxonan-3-yl)carbamate (622 mg, 1.64 mmol, 1.00 equiv) in CH$_2$Cl$_2$ (16 mL, 0.10 M) at 0° C. (ice water bath) were added but-3-yn-2-one (0.192 mL, 2.46 mmol, 1.50 equiv) and DABCO (9 mg, 0.08 mmol, 0.05 equiv). The dark solution was removed from the cold bath, stirred at room temperature for 2 h, concentrated, and purified by automated silica gel column chromatography (5-50% EtOAc in hexanes) to provide tert-butyl ((3S,7S,8R,9S)-7-benzyl-9-methyl-2-oxo-8-(((E)-3-oxobut-1-en-1-yl)oxy)-1, 5-dioxonan-3-yl)carbamate (617 mg, 84%) as an amorphous white solid: IR (ATR) 1753, 1707, 1631, 1600, 1497, 1367, 1158, 1077, 1021, 956, 909, 730, 700 cm$^{-1}$; $^1$H NMR (400 MHz, CDCl$_3$) δ 7.47-7.35 (d, J=12.3 Hz, 1H), 7.35-7.25 (m, 1H), 7.25-7.16 (m, 1H), 7.16-7.04 (m, 2H), 5.84-5.71 (d, J=12.3 Hz, 1H), 5.16-5.07 (d, J=8.2 Hz, 1H), 5.07-4.95 (dq, J=9.3, 6.4 Hz, 1H), 4.72-4.57 (q, J=7.4 Hz, 1H), 4.01-3.85 (dd, J=11.6, 7.5 Hz, 1H), 3.82-3.67 (t, J=9.2 Hz, 1H), 2.14-2.05 (m, 1H), 3.59-3.49 (m, 1H), 3.49-3.40 (m, 1H), 3.36-3.23 (dd, J=11.1, 7.6 Hz, 1H), 2.97-2.86 (dd, J=13.8, 3.7 Hz, 1H), 2.45-2.30 (m, 1H), 2.21-2.14 (s, 3H), 2.14-2.05 (s, 1H), 1.49-1.41 (s, 9H), 1.41-1.36 (d, J=6.4 Hz, 3H); $^{13}$C NMR (101 MHz, CDCl$_3$) δ 197.25, 172.15, 162.57, 138.45, 129.07, 128.58, 126.52, 108.48, 89.17, 80.33, 73.86, 72.57, 71.38, 52.71, 46.43, 35.29, 28.69, 28.26, 18.73, 14.20; HRMS-ESI (m/z) [M+Na]$^+$ calc'd for $C_{24}H_{33}NO_7Na$, 470.2149. found, 470.2160.

Example 8

Step 2: Preparation of tert-butyl ((3S,7S,8R,9S)-7-benzyl-9-methyl-2-oxo-8-(3-oxobutoxy)-1,5-dioxonan-3-yl)carbamate (Compound 75) and tert-butyl ((3S,7S,8R,9S)-7-benzyl-8-(3-hydroxybutoxy)-9-methyl-2-oxo-1,5-dioxonan-3-yl)carbamate (Compound 76)

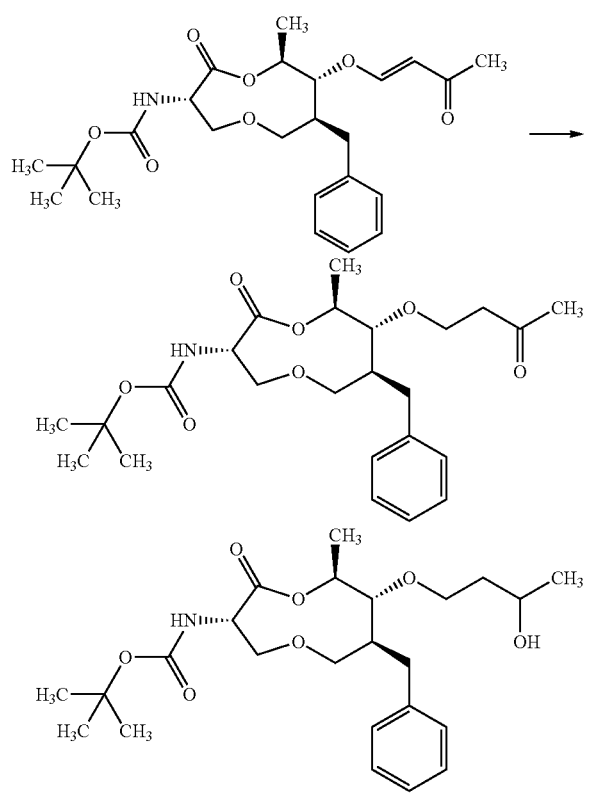

To a solution of tert-butyl ((3S,7S,8R,9S)-7-benzyl-9-methyl-2-oxo-8-(((E)-3-oxobut-1-en-1-yl)oxy)-1,5-dioxonan-3-yl)carbamate (601 mg, 1.34 mmol, 1.00 equiv) in EtOAc (13 mL) was added 10% Pd/C (72 mg, 0.067 mmol, 0.050 equiv). The resulting suspension was stirred under an atmosphere of hydrogen (1 atm, balloon) overnight. The catalyst was then filtered through a pad of Celite® that was flushed with EtOAc. The filtrate was concentrated to provide an oil. Purification by automated silica gel column chromatography (10-50% EtOAc in hexanes) provided tert-butyl ((3S,7S,8R,9S)-7-benzyl-9-methyl-2-oxo-8-(3-oxobutoxy)-1,5-dioxonan-3-yl)carbamate (417 mg, 69%) as well as tert-butyl ((3S,7S,8R,9S)-7-benzyl-8-(3-hydroxybutoxy)-9-methyl-2-oxo-1,5-dioxonan-3-yl)carbamate (86 mg, 14%).

tert-Butyl ((3S,7S,8R,9S)-7-benzyl-9-methyl-2-oxo-8-(3-oxobutoxy)-1,5-dioxonan-3-yl)carbamate: IR (ATR) 2978, 2933, 1751, 1712, 1519, 1390, 1367, 1203, 1165, 1082 cm$^{-1}$; $^1$H NMR (400 MHz, CDCl$_3$) δ 7.34-7.27 (m, 2H), 7.22-7.13 (m, 3H), 5.12 (d, J=8.2 Hz, 1H), 4.92 (dq, J=9.1, 6.4 Hz, 1H), 4.59 (q, J=7.3 Hz, 1H), 3.98-3.83 (m, 2H), 3.78 (dt, J=9.0, 6.1 Hz, 1H), 3.49-3.41 (m, 1H), 3.37 (dd, J=10.5, 6.3 Hz, 1H), 3.26 (dd, J=11.4, 7.2 Hz, 1H), 3.19-3.03 (m, 2H), 2.70 (td, J=6.1, 3.6 Hz, 2H), 2.32 (t, J=13.0 Hz, 1H), 1.89 (s, OH), 1.49 (d, J=6.4 Hz, 2H), 1.42 (s, 7H); $^{13}$C NMR (101 MHz, CDCl$_3$) δ 206.50, 172.18, 154.96, 139.78, 129.12, 128.43, 126.13, 85.39, 80.11, 77.33, 77.02, 76.70, 75.29, 72.94, 72.46, 67.16, 52.97, 47.14, 43.69, 35.16, 30.77, 28.27, 18.76; HRMS-ESI (m/z) [M+Na]$^+$ calc'd for $C_{24}H_{35}NO_7Na$, 472.2306. found, 472.2316.

tert-Butyl ((3S,7S,8R,9S)-7-benzyl-8-(3-hydroxybutoxy)-9-methyl-2-oxo-1,5-dioxonan-3-yl)carbamate: IR (ATR) 2975, 2932, 2876, 1748, 1699, 1496, 1454, 1368, 1327, 1295, 1250, 1203, 1163, 1081, 731, 701 cm$^{-1}$; $^1$H NMR (400 MHz, CDCl$_3$) δ 7.36-7.27 (m, 2H), 7.24-7.13 (m, 3H), 5.19 (dd, J=25.1, 8.2 Hz, 1H), 5.07-4.91 (m, 1H), 4.60 (d, J=6.8 Hz, 1H), 4.02 (dd, J=6.3, 3.1 Hz, 1H), 3.97-3.81 (m, 2H), 3.79-3.64 (m, 1H), 3.52-3.34 (m, 2H), 3.27 (dd, J=18.9, 11.9 Hz, 1H), 2.01-1.86 (m, 1H), 3.16 (dd, J=14.3, 8.5 Hz, 1H), 3.08 (dt, J=13.5, 3.2 Hz, 1H), 2.56 (s, 1H), 2.48-2.31 (m, 1H), 1.81-1.66 (m, 2H), 1.51 (dd, J=6.5, 1.9 Hz, 3H), 1.42 (s, 9H), 1.22 (d, J=6.2 Hz, 3H); $^{13}$C NMR (101 MHz, CDCl$_3$) δ 172.24, 155.00, 139.66, 139.56, 129.16, 129.10, 128.49, 126.22, 85.52, 85.28, 75.04, 66.93, 52.95, 47.29, 38.75, 35.20, 28.27, 23.67, 18.79; HRMS-ESI (m/z) [M+Na]$^+$ calc'd for $C_{24}H_{37}NO_7Na$ 474.2462 found 474.2474.

Example 8

Step 3: Preparation of tert-butyl ((3S,7S,8R,9S)-7-benzyl-8-(3-methoxybutoxy)-9-methyl-2-oxo-1,5-dioxonan-3-yl)carbamate (Compound 81)

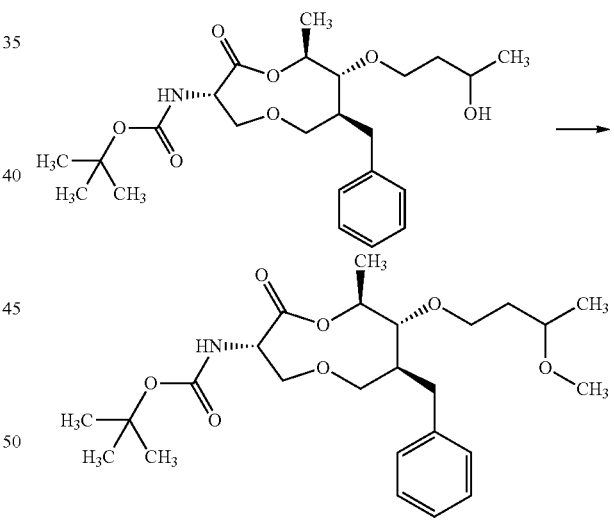

To a solution of tert-butyl ((3S,7S,8R,9S)-7-benzyl-8-(3-hydroxybutoxy)-9-methyl-2-oxo-1,5-dioxonan-3-yl)carbamate (82 mg, 0.18 mmol, 1.00 equiv) in CH$_2$Cl$_2$ (1.8 mL) were added proton sponge (156 mg, 0.726 mmol, 4.00 equiv) and trimethyloxonium tetrafluoroborate (54 mg, 0.36 mmol, 2.0 equiv). The resulting suspension was stirred at room temperature for 1 h, poured into ½ sat'd NaHCO$_3$ solution (20 mL), and extracted with CH$_2$Cl$_2$ (3×20 mL). The combined organic extracts were dried over Na$_2$SO$_4$, filtered, and concentrated to provide a yellow oil. Purification by automated silica gel column chromatography (1-6% acetone in CH$_2$Cl$_2$) provided tert-butyl ((3S,7S,8R,9S)-7-benzyl-8-(3-methoxybutoxy)-9-methyl-2-oxo-1,5-dioxonan-3-yl)carbamate (71 mg, 84%) as a sticky oil: $^1$H NMR (400 MHz, CDCl$_3$) δ 7.32-7.23 (m, 2H), 7.23-7.13 (m, 3H), 5.18 (d, J=6.9 Hz, 1H), 5.02-4.86 (m, 1H), 4.60 (q, J=7.2 Hz, 1H), 3.94-3.75 (m, 2H), 3.75-3.62 (m, 1H), 3.62-3.41 (m, 3H), 3.36 (dd, J=10.5, 6.5 Hz, 1H), 3.33-3.22 (m, 4H), 3.21-3.04 (m, 2H), 2.29 (t, J=12.5 Hz, 1H), 2.00-1.81 (m, 1H), 1.81-1.68 (m, 2H), 1.48 (s, 3H), 1.41 (s, 9H), 1.15 (d, J=6.1 Hz, 3H); $^{13}$C NMR (101 MHz, CDCl$_3$) δ 172.21, 154.98, 139.93, 139.88, 129.13, 128.42, 126.10, 85.02, 80.03, 75.51, 75.45, 73.41, 73.39, 72.91, 72.58, 69.09, 68.84, 55.94, 55.89, 53.01, 47.27, 47.14, 37.41, 37.35, 35.14, 35.03, 28.27, 19.09, 18.73.

Example 9

Step 1: Preparation of tert-butyl ((3S,7S,8R,9S)-7-benzyl-9-methyl-8-((3-methylbut-3-en-1-yl)oxy)-2-oxo-1,5-dioxonan-3-yl)carbamate (Compound 77)

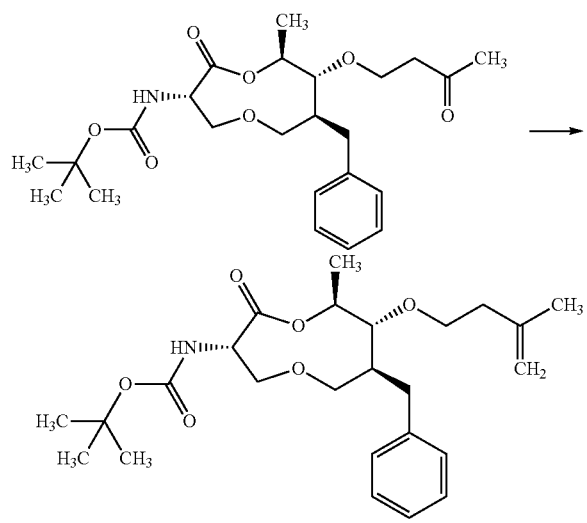

To a suspension of methyltriphenylphosphonium bromide (346 mg, 0.969 mmol, 1.40 equiv) in anhydrous THF (7 mL) at −78° C. (dry ice/acetone) was added a 2.5 M solution of n-butyllithium in hexane (n-BuLi; 332 μL, 0.830 mmol, 1.20 equiv). The flask was removed from the cold bath for 25 min and then re-cooled to −78° C. In a separate vessel, tert-butyl ((3S,7S,8R,9S)-7-benzyl-9-methyl-2-oxo-8-(3-oxobutoxy)-1,5-dioxonan-3-yl)carbamate (311 mg, 0.692 mmol, 1.00 equiv) was dissolved in anhydrous THF (7 mL), cooled to −78° C., and transferred via cannula to the phosphonium ylide solution prepared above. The resulting light yellow suspension was stirred at −78° C. for 50 min and then transferred to a −50° C. bath (deficient dry ice/acetone) and stirred for 45 min. The suspension was slowly warmed to −20° C. over 1 h and then warmed to 0° C. (ice water bath) and stirred for 20 min. The reaction was quenched with ½ sat'd aq. ammonium chloride (NH$_4$Cl; 20 mL) and extracted with EtOAc (3×20 mL). The combined organic extracts were dried over MgSO$_4$, filtered, and concentrated to give a colorless oil. Purification by automated silica gel column chromatography (2-25% acetone in hexanes) provided tert-butyl ((3S,7S,8R, 9S)-7-benzyl-9-methyl-8-((3-methylbut-3-en-1-yl)oxy)-2-oxo-1,5-dioxonan-3-yl)carbamate (68 mg, 22%) as a sticky oil: IR (ATR) 2977, 2933, 2875, 1750, 1712, 1497, 1454, 1367, 1326, 1250, 1202, 1163, 1080, 1042, 1023 cm$^{−1}$; $^1$H NMR (400 MHz, CDCl$_3$) δ 7.38-7.23 (m, 2H), 7.23-7.10 (m, 3H), 5.16 (d, J=8.2 Hz, 1H), 4.95 (dq, J=9.2, 6.4 Hz, 1H), 4.80 (s, 1H), 4.77-4.69 (m, 1H), 4.59 (q, J=7.4 Hz, 1H), 3.88 (dd, J=11.5, 7.3 Hz, 1H), 3.83-3.71 (m, 1H), 1.57-1.46 (m, 3H), 3.65 (dt, J=8.7, 7.0 Hz, 1H), 3.50-3.31 (m, 2H), 3.25 (dd, J=11.4, 7.3 Hz, 1H), 3.20-3.02 (m, 2H), 2.32 (t, J=6.9 Hz, 3H), 1.91 (s, 1H), 1.49 (d, J=6.4 Hz, 3H), 1.41 (s, 9H); $^{13}$C NMR (101 MHz, CDCl$_3$) δ 172.27, 154.98, 142.31, 139.91, 129.15, 128.43, 126.12, 111.99, 85.31, 80.06, 75.48, 72.79, 72.30, 71.29, 52.93, 47.28, 38.33, 35.19, 28.28, 22.88, 18.80; HRMS-ESI (m/z) [M+Na]$^+$ calc'd for C$_{25}$H$_{37}$NO$_6$Na, 470.2513. found, 470.2522.

Example 9

Step 2: Preparation of tert-butyl ((3S,7S,8R,9S)-7-benzyl-8-(isopentyloxy)-9-methyl-2-oxo-1,5-dioxonan-3-yl)carbamate (Compound 79)

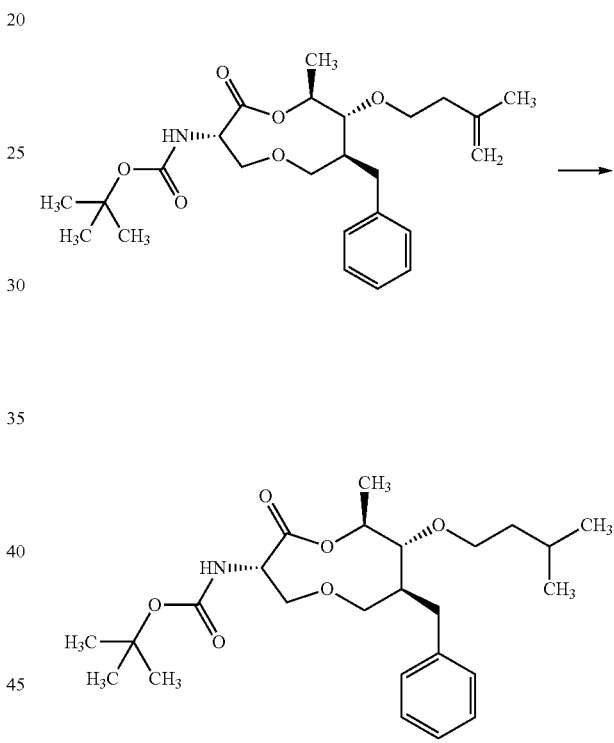

To a solution of tert-butyl ((3S,7S,8R,9S)-7-benzyl-9-methyl-8-((3-methylbut-3-en-1-yl)oxy)-2-oxo-1,5-dioxonan-3-yl)carbamate (100 mg, 0.223 mmol, 1.00 equiv) in EtOAc (3 mL) was added 10% Pd/C (12 mg, 0.011 mmol, 0.05 equiv). The resulting suspension was stirred under an atmosphere of H$_2$ (balloon pressure) for 16 h and filtered through a plug of Celite®. The filtrate was concentrated to provide tert-butyl ((3S,7S,8R,9S)-7-benzyl-8-(isopentyloxy)-9-methyl-2-oxo-1,5-dioxonan-3-yl)carbamate (97 mg, 97%) as a sticky oil: $^1$H NMR (400 MHz, CDCl$_3$) δ 7.38-7.23 (m, 2H), 7.23-7.11 (m, 3H), 5.13 (d, J=7.7 Hz, 1H), 4.94 (dq, J=9.2, 6.4 Hz, 1H), 4.59 (q, J=7.3 Hz, 1H), 3.88 (dd, J=11.5, 7.3 Hz, 1H), 3.77-3.63 (m, 1H), 3.56 (dt, J=8.7, 6.9 Hz, 1H), 3.49-3.41 (m, 1H), 3.37 (dd, J=10.5, 6.4 Hz, 1H), 3.26 (dd, J=11.3, 7.3 Hz, 1H), 3.20-3.04 (m, 2H), 2.30 (t, J=12.6 Hz, 1H), 1.90 (s, 1H), 1.73 (dp, J=13.3, 6.7 Hz, 1H), 1.55-1.46 (m, 5H), 1.42 (s, 9H), 0.91 (dd, J=6.6, 0.8 Hz, 6H); $^{13}$C NMR (101 MHz, CDCl$_3$) δ 172.25, 154.97, 139.96, 129.15, 128.43, 126.11, 85.13, 80.07, 75.58, 72.90, 72.45, 71.19, 52.97, 47.31, 39.17, 35.16, 28.27, 24.90, 22.70, 22.68, 18.77; ESIMS m/z 472.7 ([M+Na]$^+$).

Example 10

Step 1: Preparation of tert-butyl ((3S,7S,8R,9S)-7-benzyl-9-methyl-2-oxo-8-phenoxy-1,5-dioxonan-3-yl)carbamate (Compound 73)

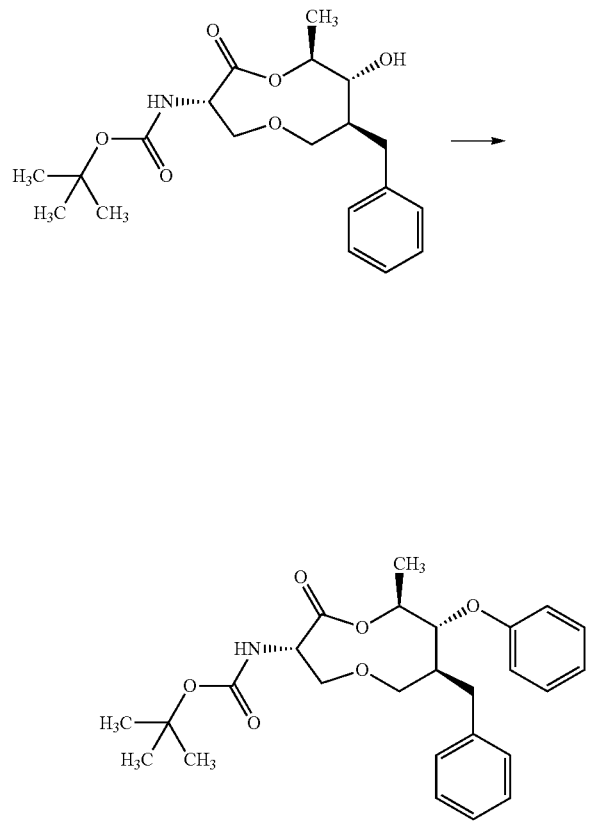

To a solution of tert-butyl ((3S,7S,8R,9S)-7-benzyl-8-hydroxy-9-methyl-2-oxo-1,5-dioxonan-3-yl)carbamate (500 mg, 1.32 mmol, 1.00 equiv) in anhydrous CH$_3$CN (13 mL) were added 2-(trimethylsilyl)phenyl trifluoromethanesulfonate (0.480 mL, 1.98 mmol, 1.50 equiv) followed by CsF (500 mg, 3.29 mmol, 2.50 equiv). The resulting mixture was stirred at room temperature for 2 d. The reaction was then poured into ½ sat'd NaCl solution (20 mL), extracted with EtOAc (3×20 mL), and the combined organic extracts were dried over MgSO$_4$, filtered, and concentrated to provide an oily yellow suspension. This was purified by automated silica gel column chromatograpy to provide tert-butyl ((3S,7S,8R,9S)-7-benzyl-9-methyl-2-oxo-8-phenoxy-1,5-dioxonan-3-yl)carbamate (69 mg, 11%) as an amorphous light yellow solid: $^1$H NMR (400 MHz, CDCl$_3$) δ 7.34-7.20 (m, 5H), 7.20-7.04 (m, 4H), 7.02-6.88 (d, J=8.7 Hz, 4H), 5.20-5.02 (dq, J=9.1, 6.4 Hz, 2H), 4.71-4.57 (m, 1H), 4.37-4.21 (t, J=8.9 Hz, 1H), 4.00-3.88 (dd, J=11.6, 7.3 Hz, 1H), 3.60-3.44 (s, 2H), 3.38-3.21 (m, 1H), 3.07-2.93 (dd, J=13.6, 3.1 Hz, 1H), 2.37-2.21 (t, J=12.5 Hz, 1H), 2.22-2.09 (m, 1H), 1.46-1.40 (s, 9H), 1.40-1.34 (d, J=6.4 Hz, 3H); $^{13}$C NMR (101 MHz, CDCl$_3$) δ 172.29, 159.20, 154.98, 139.50, 129.75, 129.11, 128.42, 126.19, 121.34, 115.48, 81.96, 80.19, 75.39, 72.88, 72.08, 52.98, 47.56, 35.29, 28.29, 18.98; ESIMS m/z 478.6 ([M+Na]$^+$).

Example 11

Steps 1 and 2: Preparation of tert-butyl N-[(3S,7S,8R,9S)-7-benzyl-8-(2,2-difluoroethoxy)-9-methyl-2-oxo-1,5-dioxonan-3-yl]-N-tert-butoxycarbonyl carbamate (Compound 80)

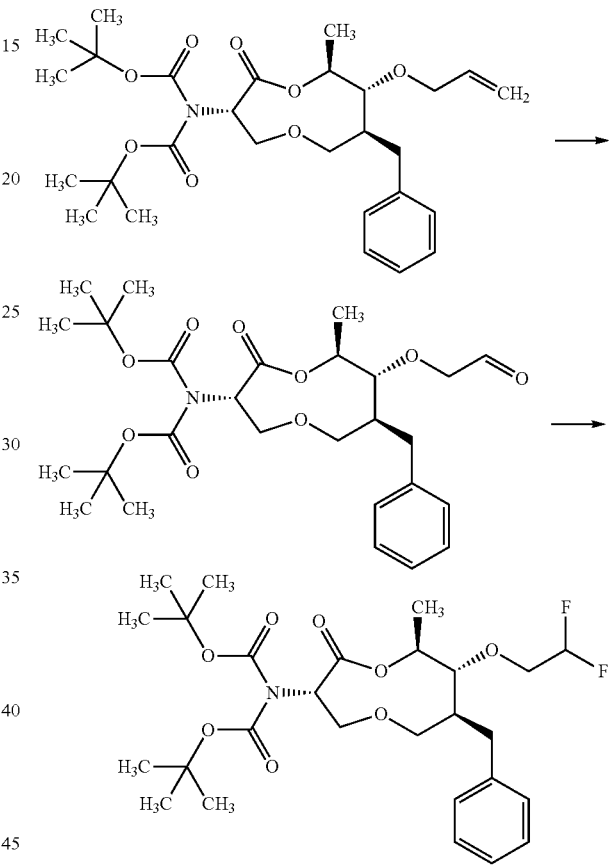

To a solution of tert-butyl N-((3S,7S,8R,9S)-8-allyloxy-7-benzyl-9-methyl-2-oxo-1,5-dioxonan-3-yl)-N-tert-butoxycarbonyl carbamate (340 mg, 0.65 mmol) in CH$_2$Cl$_2$ (6.3 mL) and MeOH (0.211 mL) was added NaHCO$_3$ (6 mg, 0.07 mmol, 0.1 equiv). This mixture was cooled to −78° C. (dry ice/acetone) and ozone was bubbled through the solution until a blue color persisted. The solution was purged with oxygen and dimethyl sulfide (0.300 mL, 4.06 mmol, 6.20 equiv) was added. The solution was removed from the cold bath and stirred at room temperature for 16 h, concentrated, and purified by automated silica gel column chromatography to provide tert-butyl N-((3S,7S,8R,9S)-7-benzyl-9-methyl-2-oxo-8-(2-oxoethoxy)-1,5-dioxonan-3-yl)-N-tert-butoxycarbonyl carbamate. The aldehyde was dissolved in CH$_2$Cl$_2$ (6.0 mL) and cooled to 0° C. (ice water bath). To this solution was added deoxofluor (0.231 mL, 1.25 mmol, 2.10 equiv) as a solution in CH$_2$Cl$_2$ (1.2 mL). The resulting solution was stirred at 0° C. for 50 min, concentrated, and purified by automated silica gel column chromatography (2-25% acetone in hexanes) to provide tert-butyl N-[(3S,7S,8R,9S)-7-benzyl- 8-(2,2-difluoroethoxy)-9-methyl-2-oxo-1,5-dioxonan-3-yl]-N-tert-butoxycarbonyl carbamate (131 mg, 37%) as an amorphous white solid: IR (ATR) 2980 (m), 2934 (m), 1742 (s), 1706 (s), 1455 (w), 1393 (w), 1367 (s), 1313 (w), 1254 (m), 1145 (s), 1120 (s), 1060 (m) cm$^{-1}$; $^1$H NMR (400 MHz, CDCl$_3$) δ 7.32-7.23 (m, 2H), 7.23-7.13 (m, 3H), 6.05-5.59 (m, 1H), 5.11 (dd, J=8.5, 6.7 Hz, 1H), 4.91 (dq, J=8.8, 6.4 Hz, 1H), 4.09 (dd, J=11.8, 6.7 Hz, 1H), 3.97-3.79 (m, 2H), 3.79-3.64 (m, 1H), 3.51 (d, J=10.7 Hz, 1H), 3.46-3.37 (m, 1H), 3.28 (t, J=8.8 Hz, 1H), 3.06 (dd, J=13.6, 3.8 Hz, 1H), 2.45 (t, J=12.3 Hz, 1H), 2.13-1.88 (m, 1H), 1.57-1.39 (m, 21H); $^{13}$C NMR (101 MHz, CDCl$_3$) δ 169.91, 152.61, 139.47, 129.20, 128.41, 126.20, 113.89, 85.92, 83.09, 74.55, 70.83, 57.30, 46.62, 35.08, 27.92, 18.88; HRMS-ESI (m/z) [M+Na]$^+$ calc'd for C$_{27}$H$_{39}$F$_2$NO$_8$Na, 566.2536. found, 566.2556.

Example 12

Step 1: Preparation of N-((3S,7S,8R,9S)-7-(cyclohexylmethyl)-8-isobutoxy-9-methyl-2-oxo-1,5-dioxonan-3-yl)-3-hydroxy-4-methoxypicolinamide (Compound 4)

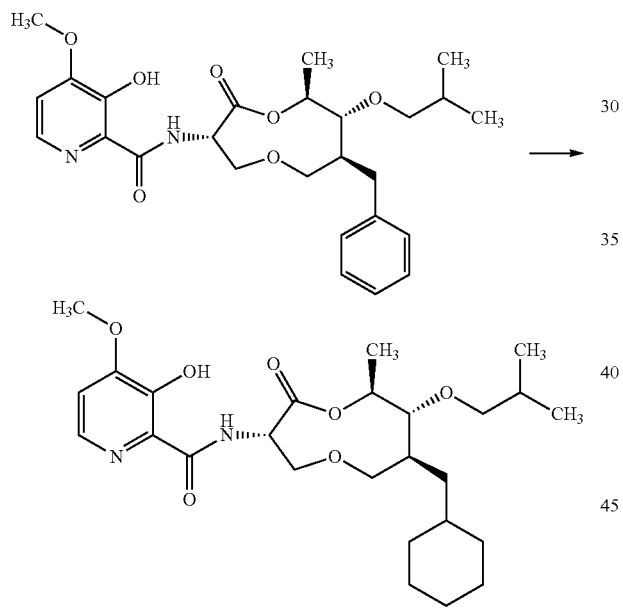

A solution of N-[(3S,7S,8R,9S)-7-benzyl-8-isobutoxy-9-methyl-2-oxo-1,5-dioxonan-3-yl]-3-hydroxy-4-methoxypyridine-2-carboxamide (25 mg, 0.05 mmol) in THF (1.2 mL) was passed through an H-cube bench top hydrogenator (5% Rh/C catalyst, 100° C., 100 bar H$_2$, 1 mL/min). The reaction mixture was concentrated to furnish N-((3S,7 S,8R, 9S)-7-(cyclohexylmethyl)-8-isobutoxy-9-methyl-2-oxo-1,5-dioxonan-3-yl)-3-hydroxy-4-methoxypicolinamide as a white solid (21 g, 83%): mp 89-92° C.; $^1$H NMR (400 MHz, CDCl$_3$) δ 11.97 (s, 1H), 8.60 (d, J=8.2 Hz, 1H), 7.99 (d, J=5.2 Hz, 1H), 6.86 (d, J=5.2 Hz, 1H), 5.07-4.85 (m, 2H), 4.07 (dd, J=11.7, 7.1 Hz, 1H), 3.93 (s, 3H), 3.60 (dd, J=10.3, 3.3 Hz, 2H), 3.57-3.45 (m, 1H), 3.35 (dd, J=8.3, 6.3 Hz, 1H), 3.23 (dd, J=8.3, 6.6 Hz, 1H), 2.96 (t, J=9.0 Hz, 1H), 1.91-1.53 (m, 9H), 1.45 (d, J=6.4 Hz, 3H), 1.37-1.08 (m, 6H), 0.92 (dd, J=6.7, 3.3 Hz, 6H); $^{13}$C NMR (101 MHz, CDCl$_3$) δ 171.0, 169.9, 155.3, 148.7, 140.6, 130.3, 125.5, 109.6, 85.0, 79.0, 76.1, 72.6, 56.1, 51.8, 42.7, 36.4, 34.9, 32.5, 30.3, 29.2, 26.6, 26.5, 26.2, 19.6, 19.5, 18.9. ESIMS m/z 493.0 ([M+H]$^+$).

Example 13

Preparation of 2-(((3S,7S,8R,9S)-7-benzyl-8-isobutoxy-9-methyl-2-oxo-1,5-dioxonan-3-yl)carbamoyl)-4-methoxypyridin-3-yl acetate (Compound 9)

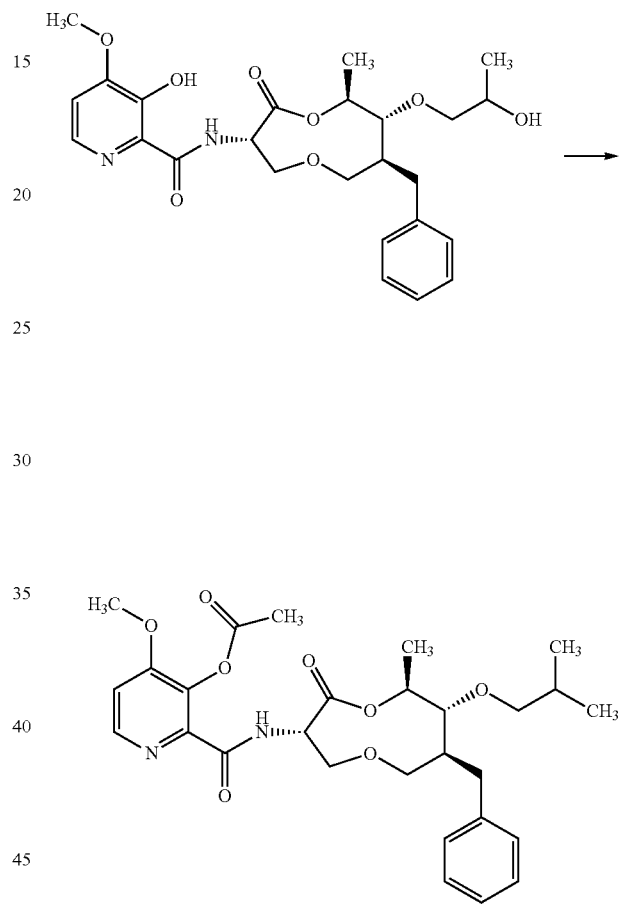

To a solution of N-((3S,7S,8R,9S)-7-benzyl-8-(2-hydroxypropoxy)-9-methyl-2-oxo-1,5-dioxonan-3-yl)-3-hydroxy-4-methoxypicolinamide (160 mg, 0.33 mmol) in CH$_2$Cl$_2$ (2 mL) were added acety chloride (26 μL, 0.36 mmol) and DMAP (44 mg, 0.36 mmol) at 0° C., and the solution was allowed to warm to room temperature overnight. The crude reaction mixture was concentrated and the residue purified via flash chromatography (SiO$_2$, 50% EtOAc/hexanes) to furnish the product as white foam (139 mg, 80%): IR (film) 3375, 3026, 2957, 2875, 1772, 1748, 1680 cm$^{-1}$; $^1$H NMR (400 MHz, CDCl$_3$) δ 8.56 (d, J=8.1 Hz, 1H), 8.32 (d, J=5.5 Hz, 1H), 7.34-7.23 (m, 2H), 7.20 (t, J=6.7 Hz, 3H), 7.00 (d, J=5.7 Hz, 1H), 5.05-4.91 (m, 2H), 3.99 (dd, J=11.7, 7.4 Hz, 1H), 3.90 (s, 3H), 3.51-3.29 (m, 5H), 3.19-3.08 (m, 2H), 2.38 (s, 3H), 2.36-2.25 (m, 1H), 2.02-1.81 (m, 2H), 1.49 (d, J=6.4 Hz, 3H), 0.96 (d, J=6.7 Hz, 6H); $^{13}$C NMR (101 MHz, CDCl$_3$) δ 171.71, 168.88, 162.67, 159.41, 146.75, 141.14, 140.00, 137.50, 129.21 (2), 128.43 (2), 126.10, 109.89, 84.55, 79.19, 75.73, 72.29, 72.09, 56.29, 51.54, 47.39, 35.09, 29.19, 20.73, 19.50 (2), 18.83; ESIMS m/z 529.02 ([M]+).

Example 14

Preparation of 2-(((3S,7S,8R,9S)-7-benzyl-8-isobutoxy-9-methyl-2-oxo-1,5-dioxonan-3-yl)carbamoyl)-4-methoxypyridin-3-yl isopropyl carbonate (Compound 10)

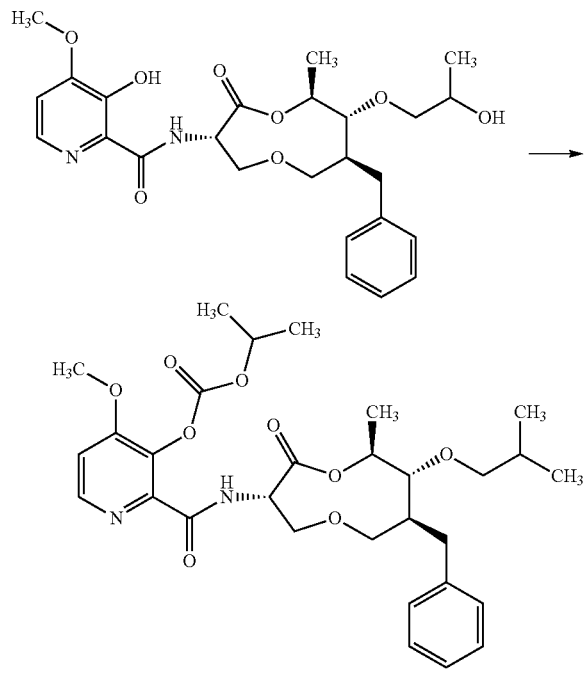 [SMILES: COc1ccnc(C(=O)N[C@H]2COC[C@H](Cc3ccccc3)[C@@H](OCC(C)O)[C@H](C)OC2=O)c1O ; COc1ccnc(C(=O)N[C@H]2COC[C@H](Cc3ccccc3)[C@@H](OCC(C)C)[C@H](C)OC2=O)c1OC(C)=O]

To a solution of N-((3S,7S,8R,9S)-7-benzyl-8-(2-hydroxypropoxy)-9-methyl-2-oxo-1,5-dioxonan-3-yl)-3-hydroxy-4-methoxypicolinamide (160 mg, 0.33 mmol) in $CH_2Cl_2$ (2 mL) were added isopropyl chloroformate (44 mg, 0.36 mmol) and DMAP (44 mg, 0.36 mmol) at 0° C., and the solution was allowed to warm to room temperature overnight. The crude reaction mixture was concentrated and the residue purified via flash chromatography ($SiO_2$, 50% EtOAc/hexanes) to furnish the product (83 mg, 44%) as white foam: IR (film) 3375, 2956, 2874, 1762, 1680 $cm^{-1}$; $^1H$ NMR (400 MHz, $CDCl_3$) δ 8.49 (d, J=8.4 Hz, 1H), 8.32 (d, J=5.4 Hz, 1H), 7.33-7.24 (m, 2H), 7.20 (dd, J=7.2, 5.3 Hz, 3H), 7.00 (d, J=5.5 Hz, 1H), 5.08-4.91 (m, 3H), 4.01 (dd, J=11.7, 7.4 Hz, 1H), 3.92 (s, 3H), 3.50-3.42 (m, 3H), 3.37-3.30 (m, 2H), 3.17-3.11 (m, 2H), 2.37-2.29 (m, 1H), 2.00-1.83 (m, 2H), 1.49 (d, J=6.4 Hz, 3H), 1.41 (d, J=6.3 Hz, 6H), 0.97-0.93 (m, 6H); $^{13}C$ NMR (101 MHz, $CDCl_3$) δ 171.79, 162.53, 159.38, 152.03, 146.81, 141.44, 140.03, 137.78, 129.20 (2), 128.43 (2), 126.09, 110.03, 84.53, 79.27, 75.68, 73.76, 72.31, 71.92, 56.32, 51.44, 47.43, 35.09, 29.19, 21.71 (2), 19.50 (2), 18.79; ESIMS m/z 574.39 ([M+H]+).

Example A

Evaluation of Fungicidal Activity: Leaf Blotch of Wheat (*Mycosphaerella Graminicola*; Anamorph: *Septoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1$^{st}$ leaves of untreated plants, infection levels were assessed on a scale of 0 to 100 percent disease severity. Percent disease control was calculated using the ratio of disease severity on treated plants relative to untreated plants.

Example B

Evaluation of Fungicidal Activity: Wheat Brown Rust (*Puccinia triticina*; Synonym: *Puccinia recondita* f. sp. *tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C

Evaluation of Fungicidal Activity: Wheat Glume Blotch (*Leptosphaeria Nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D

Evaluation of Fungicidal Activity: Spot Blotch of Barley (*Cochliobolus Sativus*; Bayer Code COCHSA)

Barley seedlings (variety Harrington) were propagated in soil-less Metro mix, with each pot having 8 to 12 plants, and used for testing when first leaf was fully emerged. Test plants were inoculated with a spore suspension of *Cochliobolus sativus* 24 hr after fungicide treatments. After inoculation the plants were placed in a dark dew room with 100% RH and temperature of 22° C. for 48 hr. The plants were then kept in a greenhouse set at 24° C. until disease fully developed. Fungicide formulation, application and disease assessment followed the procedures as described in the Example A.

Example E

Evaluation of Fungicidal Activity: Apple Scab (*Venturia Inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% RH for 48 hr, and then moved to a greenhouse set at 20° C. for disease to develop. Fungicide formulation, application and disease assessment on the sprayed leaves followed the procedures as described in the Example A.

Example F

Evaluation of Fungicidal Activity: Grape Powdery Mildew (*Uncinula Necator*; Bayer Code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example G

Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example H

Evaluation of Fungicidal Activity: Leaf Spot of Sugar Beets (*Cercospora Beticola*; Bayer Code CERCBE)

Sugar beet plants (variety HH88) were grown in soil-less Metro mix and trimmed regularly to maintain an uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example I

Evaluation of Fungicidal Activity: Asian Soybean Rust (*Phakopsora Pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 2 days prior to or 1 day after fungicide treatments. Plants were incubated for 24 h in a dark dew room at 22° C. and 100% RH then transferred to a growth room at 23° C. for disease to develop. Disease severity was assessed on the sprayed leaves.

Example J

Evaluation of Fungicidal Activity: Wheat Powdery Mildew (*Blumeria Graminis* f. sp. *Tritici*; Synonym: *Erysiphe graminis* f. sp. *Tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K

Evaluation of Fungicidal Activity: Barley Powdery Mildew (*Blumeria Graminis* f. sp. *Hordei*; Synonym: *Erysiphe Graminis* f. sp. *Hordei*; Bayer Code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example L

Evaluation of Fungicidal Activity: Barley Scald (*Rhyncosporium Secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyn-*

*cosporium secalis* 24 hr after fungicide treatments. After inoculation the plants were kept in dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example M

Evaluation of Fungicidal Activity: Rice Blast (*Magnaporthe Grisea*; Anamorph: *Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example N

Evaluation of Fungicidal Activity: Tomato Early Blight (*Alternaria Solani*; Bayer Code ALTESO)

Tomato plants (variety Outdoor girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example O

Evaluation of Fungicidal Activity: Cucumber Anthracnose (*Glomerella Lagenarium*; Anamorph: *Colletotricum Lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotricum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

Evaluation of Fungicide Mobility: Wheat Brown Rust (*Puccinia Triticina*; Synonym: *Puccinia recondita* f. sp. *Tritici*; Bayer Code PUCCRT):

"Yuma" wheat seedlings were used in the test. One mg of compound was dissolved in 9 μl of EC blank (emulsifiable concentrate) and 500 μl of acetone. Acetone was then evaporated overnight by leaving the vial open in a fume hood. Two milliliters of water containing 110 ppm Triton X-100 was added to each vial to prepare application solutions. A 2 μA drop of formulated material was applied to a marked line on the adaxial surface 5 cm from the leaf tip of the primary leaves. The primary leaves were kept in a horizontal position. Each treatment had 6 replicates. Plants were inoculated with PUCCRT 1-day after (1DPM) or 3-day prior to (3DCM) compound applications. When rust was fully expressed on primary leaves on control plants, the zone of treated leaves that was disease-free in the acropetal direction was measured with a ruler and converted to percent of the distance from marked line to leaf tip.

TABLE 1

Compound Structure

| Compound No. | Structure |
|---|---|
| 1 | |

TABLE 1-continued
Compound Structure
| Compound No. | Structure |
|---|---|
| 2 | 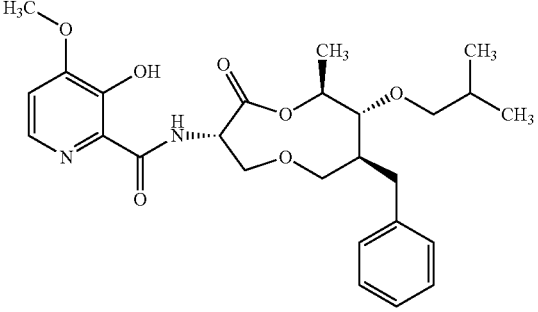 [SMILES: COc1ccnc(C(=O)N[C@H]2COC[C@H](Cc3ccccc3)[C@@H](OCC(C)C)[C@H](C)OC2=O)c1O] |
| 3 | 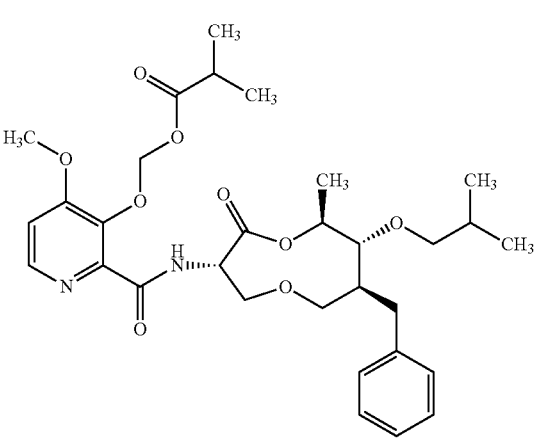 [SMILES: COc1ccnc(C(=O)N[C@H]2COC[C@H](Cc3ccccc3)[C@@H](OCC(C)C)[C@H](C)OC2=O)c1OCOC(=O)C(C)C] |
| 4 | 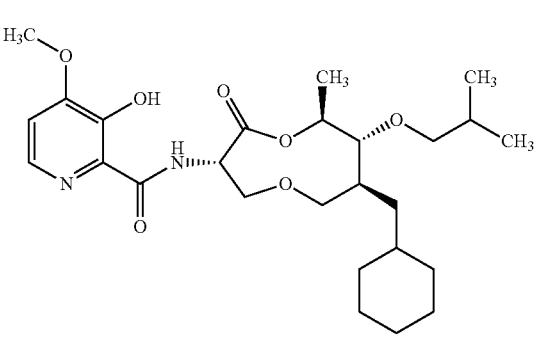 [SMILES: COc1ccnc(C(=O)N[C@H]2COC[C@H](CC3CCCCC3)[C@@H](OCC(C)C)[C@H](C)OC2=O)c1O] |
| 5 | 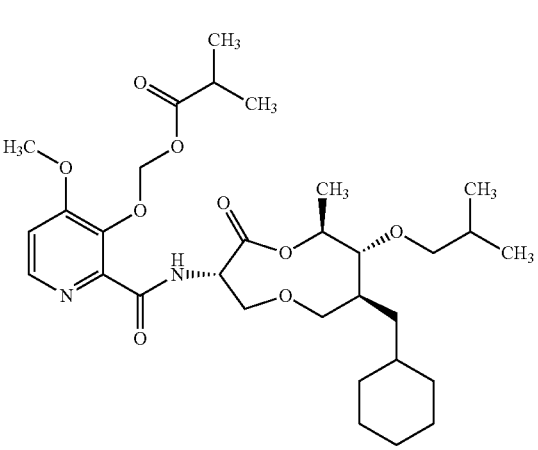 [SMILES: COc1ccnc(C(=O)N[C@H]2COC[C@H](CC3CCCCC3)[C@@H](OCC(C)C)[C@H](C)OC2=O)c1OCOC(=O)C(C)C] |

TABLE 1-continued

| Compound Structure | |
|---|---|
| Compound No. | Structure |
| 6 | |
| 7 | |
| 8 | |
| 9 | |

TABLE 1-continued
Compound Structure
| Compound No. | Structure |
|---|---|
| 10 | 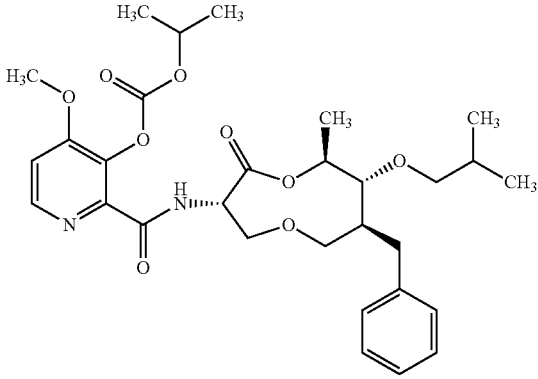 [SMILES: COc1ccnc(C(=O)N[C@H]2COC[C@H](Cc3ccccc3)[C@@H](OCC(C)C)[C@H](C)OC2=O)c1OC(=O)OC(C)C] |
| 11 | 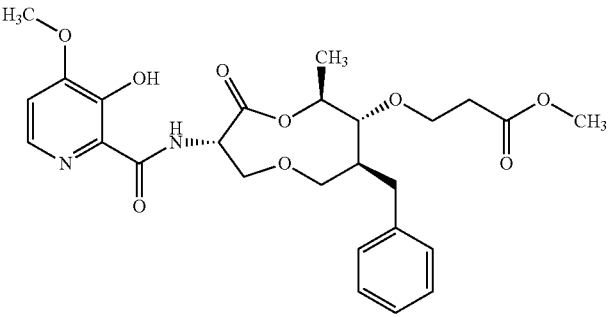 [SMILES: COC(=O)CCO[C@@H]1[C@@H](Cc2ccccc2)COC[C@H](NC(=O)c2nccc(OC)c2O)C(=O)O[C@H]1C] |
| 12 | 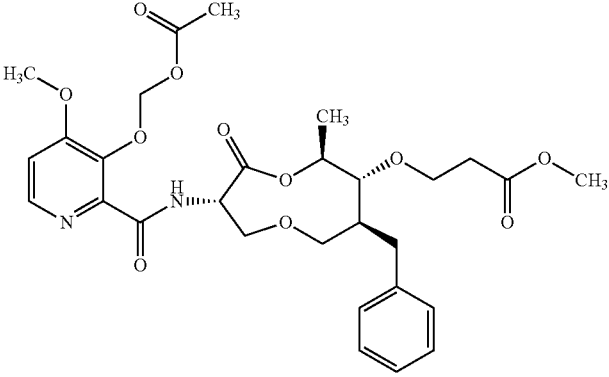 [SMILES: COC(=O)CCO[C@@H]1[C@@H](Cc2ccccc2)COC[C@H](NC(=O)c2nccc(OC)c2OCOC(C)=O)C(=O)O[C@H]1C] |
| 13 | 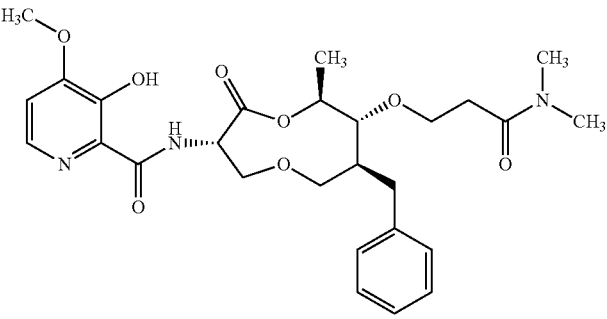 [SMILES: COc1ccnc(C(=O)N[C@H]2COC[C@H](Cc3ccccc3)[C@@H](OCCC(=O)N(C)C)[C@H](C)OC2=O)c1O] |

TABLE 1-continued

| Compound Structure | |
|---|---|
| Compound No. | Structure |
| 14 | (structure) |
| 15 | (structure) |
| 16 | (structure) |
| 17 | (structure) |

TABLE 1-continued
Compound Structure
| Compound No. | Structure |
|---|---|
| 18 | 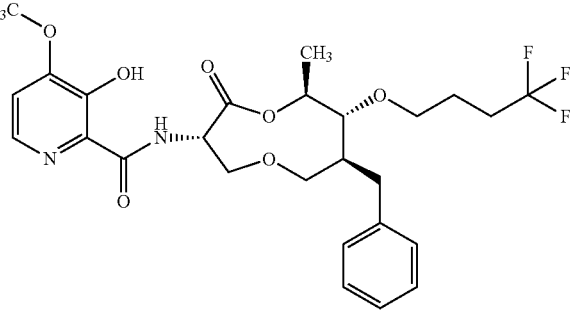 |
| 19 | 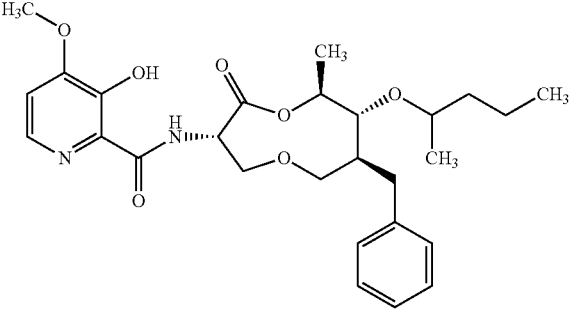 [SMILES: CCCC(C)O[C@@H]1[C@@H](Cc2ccccc2)COC[C@H](NC(=O)c2nccc(OC)c2O)C(=O)O[C@H]1C] |
| 20 | 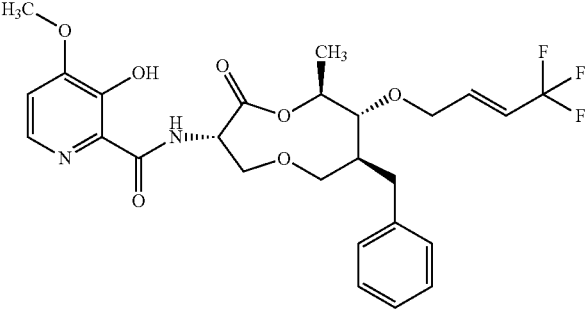 [SMILES: COc1ccnc(C(=O)N[C@H]2COC[C@H](Cc3ccccc3)[C@@H](OC/C=C/C(F)(F)F)[C@H](C)OC2=O)c1O] |
| 21 | 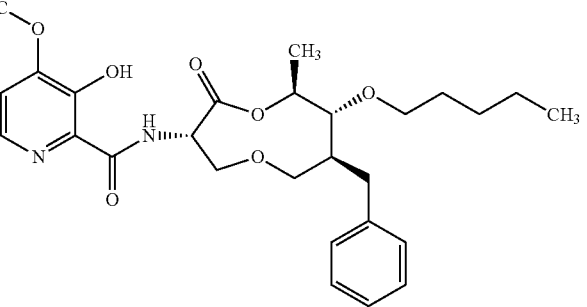 |

TABLE 1-continued

| Compound No. | Structure |
|---|---|
| 22 | |
| 23 | |
| 24 | |
| 25 | |

TABLE 1-continued
Compound Structure
| Compound No. | Structure |
|---|---|
| 26 | 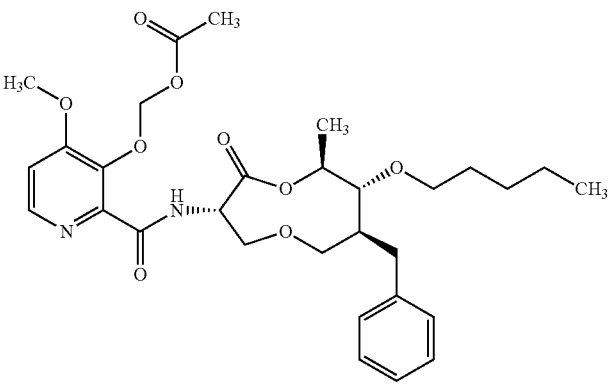 [SMILES: CCCCCO[C@@H]1[C@@H](Cc2ccccc2)COC[C@H](NC(=O)c2nccc(OC)c2OCOC(C)=O)C(=O)O[C@H]1C] |
| 27 | 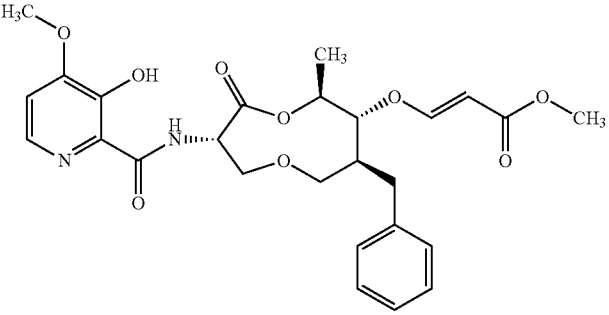 [SMILES: COC(=O)/C=C/O[C@@H]1[C@@H](Cc2ccccc2)COC[C@H](NC(=O)c2nccc(OC)c2O)C(=O)O[C@H]1C] |
| 28 | 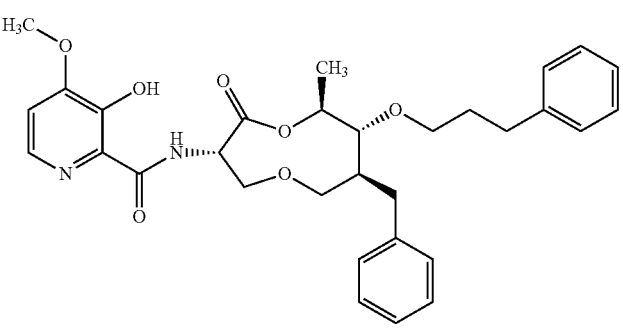 [SMILES: COc1ccnc(C(=O)N[C@H]2COC[C@H](Cc3ccccc3)[C@@H](OCCCc3ccccc3)[C@H](C)OC2=O)c1O] |
| 29 | 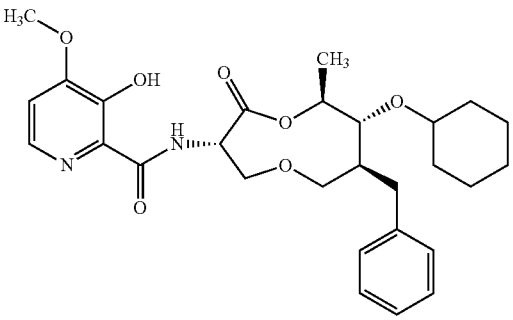 [SMILES: COc1ccnc(C(=O)N[C@H]2COC[C@H](Cc3ccccc3)[C@@H](OC3CCCCC3)[C@H](C)OC2=O)c1O] |

TABLE 1-continued

| Compound No. | Structure |
|---|---|
| 30 | |
| 31 | |
| 32 | |
| 33 | |

TABLE 1-continued

| Compound No. | Structure |
|---|---|
| 34 | |
| 35 | |
| 36 | |
| 37 | |

TABLE 1-continued

| Compound No. | Structure |
|---|---|
| 38 | (chemical structure) |
| 39 | (chemical structure) |
| 40 | (chemical structure) |
| 41 | (chemical structure) |

TABLE 1-continued

| Compound Structure | |
|---|---|
| Compound No. | Structure |

42

43

44

45

TABLE 1-continued

| Compound Structure | |
| --- | --- |
| Compound No. | Structure |
| 46 | |
| 47 | |
| 48 | |
| 49 | |

TABLE 1-continued
Compound Structure
| Compound No. | Structure |
|---|---|
| 50 | 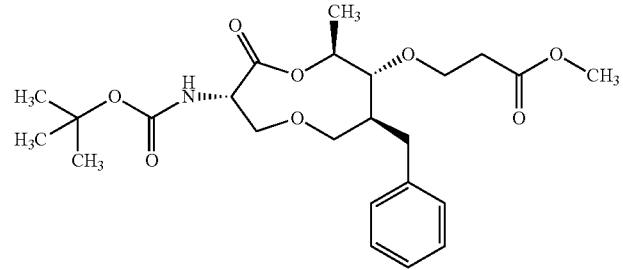 [SMILES: COC(=O)CCO[C@@H]1[C@@H](Cc2ccccc2)COC[C@H](NC(=O)OC(C)(C)C)C(=O)O[C@H]1C] |
| 51 | 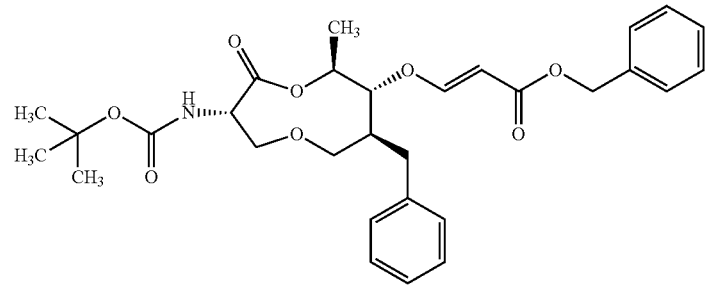 [SMILES: C[C@@H]1OC(=O)[C@@H](NC(=O)OC(C)(C)C)COC[C@H](Cc2ccccc2)[C@H]1O/C=C/C(=O)OCc1ccccc1] |
| 52 | 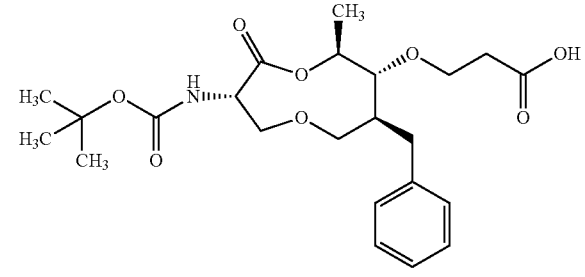 [SMILES: C[C@@H]1OC(=O)[C@@H](NC(=O)OC(C)(C)C)COC[C@H](Cc2ccccc2)[C@H]1OCCC(=O)O] |
| 53 | 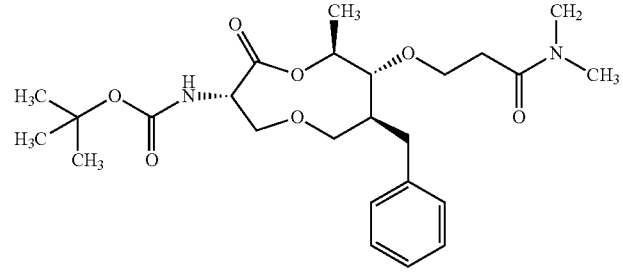 [SMILES: C[C@@H]1OC(=O)[C@@H](NC(=O)OC(C)(C)C)COC[C@H](Cc2ccccc2)[C@H]1OCCC(=O)N(C)C] |
| 54 | 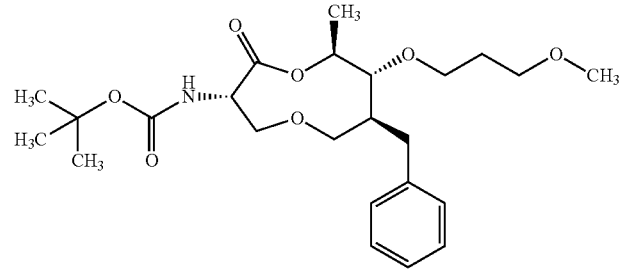 [SMILES: COCCCO[C@@H]1[C@@H](Cc2ccccc2)COC[C@H](NC(=O)OC(C)(C)C)C(=O)O[C@H]1C] |

TABLE 1-continued

| Compound No. | Structure |
|---|---|
| 55 | |
| 56 | |
| 57 | |
| 58 | |

TABLE 1-continued

| Compound No. | Structure |
|---|---|
| 59 | (structure) |
| 60 | (structure) |
| 61 | (structure) |
| 62 | (structure) |
| 63 | (structure) |

TABLE 1-continued
| Compound No. | Structure |
|---|---|
| 64 | 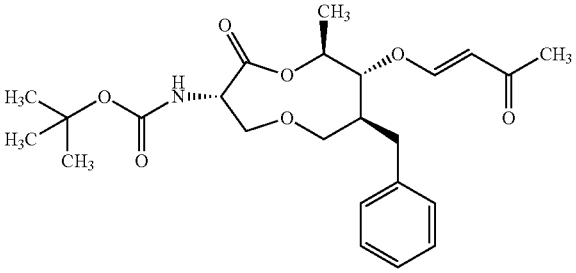 [SMILES: CC(=O)/C=C/O[C@@H]1[C@@H](Cc2ccccc2)COC[C@H](NC(=O)OC(C)(C)C)C(=O)O[C@H]1C] |
| 65 | 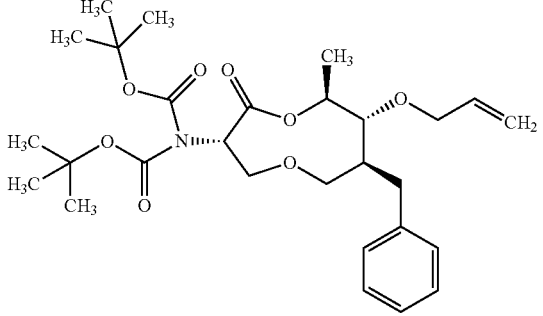 [SMILES: C=CCO[C@@H]1[C@@H](Cc2ccccc2)COC[C@H](N(C(=O)OC(C)(C)C)C(=O)OC(C)(C)C)C(=O)O[C@H]1C] |
| 66 | 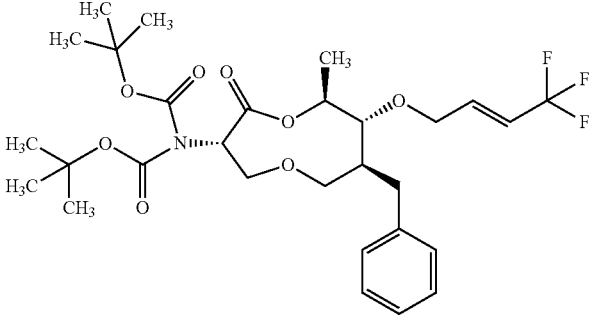 [SMILES: C[C@@H]1OC(=O)[C@@H](N(C(=O)OC(C)(C)C)C(=O)OC(C)(C)C)COC[C@H](Cc2ccccc2)[C@H]1OC/C=C/C(F)(F)F] |
| 67 | 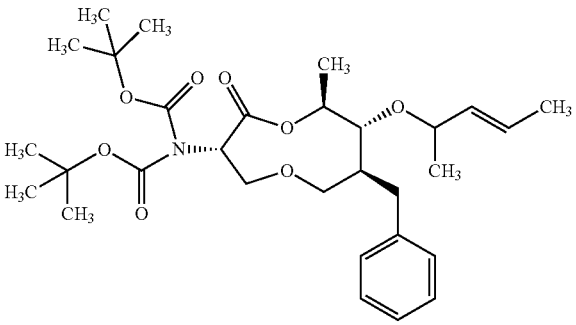 [SMILES: C/C=C/C(C)O[C@@H]1[C@@H](Cc2ccccc2)COC[C@H](N(C(=O)OC(C)(C)C)C(=O)OC(C)(C)C)C(=O)O[C@H]1C] |

TABLE 1-continued

Compound Structure

| Compound No. | Structure |
|---|---|
| 68 | 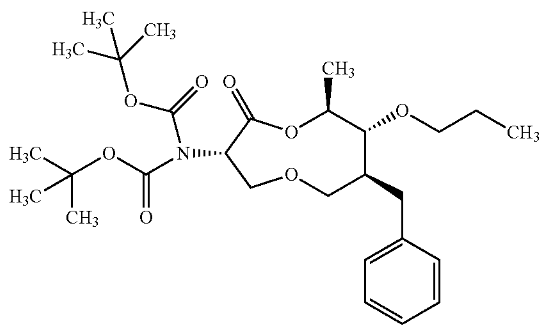 [SMILES: CCCO[C@@H]1[C@@H](Cc2ccccc2)COC[C@H](N(C(=O)OC(C)(C)C)C(=O)OC(C)(C)C)C(=O)O[C@H]1C] |
| 69 | 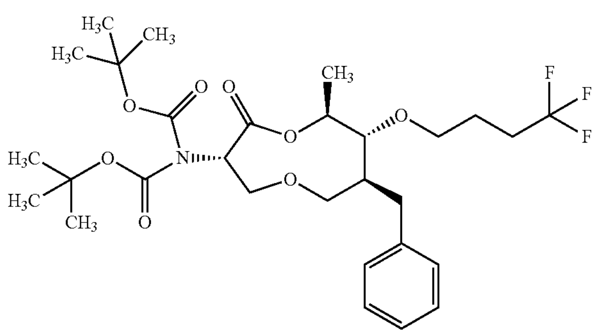 [SMILES: C[C@@H]1OC(=O)[C@@H](N(C(=O)OC(C)(C)C)C(=O)OC(C)(C)C)COC[C@H](Cc2ccccc2)[C@H]1OCCCC(F)(F)F] |
| 70 | 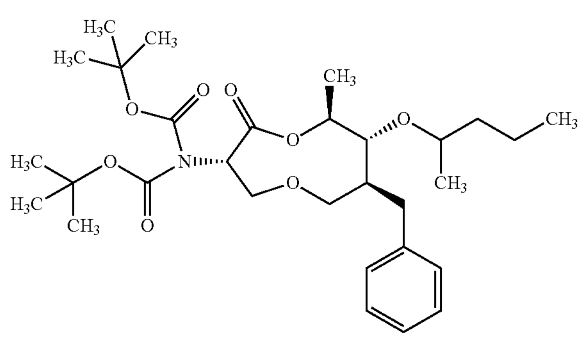 [SMILES: CCCC(C)O[C@@H]1[C@@H](Cc2ccccc2)COC[C@H](N(C(=O)OC(C)(C)C)C(=O)OC(C)(C)C)C(=O)O[C@H]1C] |
| 71 | 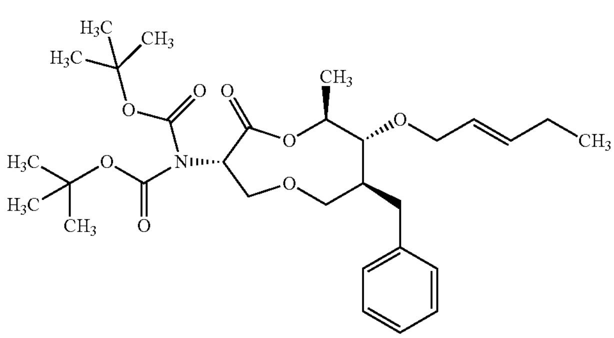 [SMILES: CC/C=C/CO[C@@H]1[C@@H](Cc2ccccc2)COC[C@H](N(C(=O)OC(C)(C)C)C(=O)OC(C)(C)C)C(=O)O[C@H]1C] |

TABLE 1-continued

| Compound No. | Structure |
|---|---|
| 72 | |
| 73 | |
| 74 | |
| 75 | |
| 76 | |

TABLE 1-continued

| Compound No. | Structure |
|---|---|
| 77 | 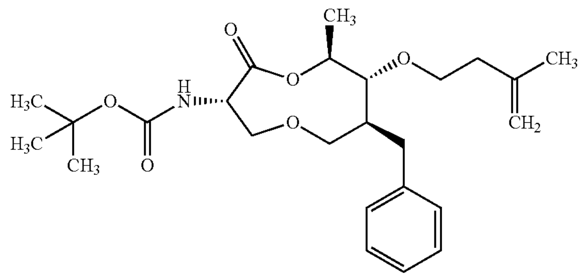 [SMILES: C=C(C)CCO[C@@H]1[C@@H](Cc2ccccc2)COC[C@H](NC(=O)OC(C)(C)C)C(=O)O[C@H]1C] |
| 78 | 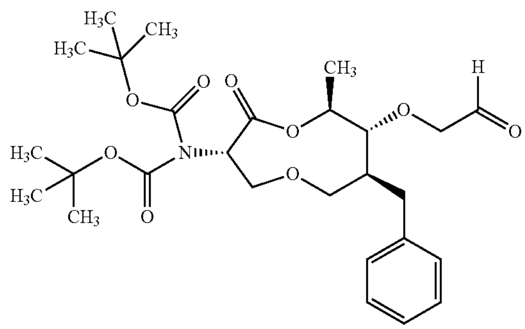 [SMILES: C[C@@H]1OC(=O)[C@@H](N(C(=O)OC(C)(C)C)C(=O)OC(C)(C)C)COC[C@H](Cc2ccccc2)[C@H]1OCC=O] |
| 79 | 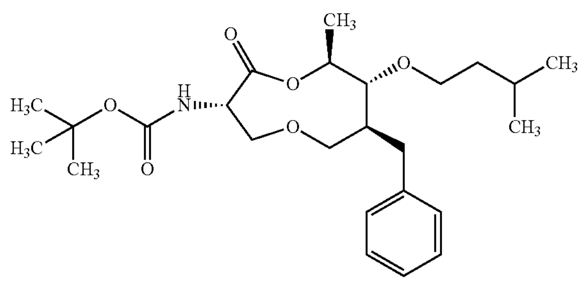 [SMILES: CC(C)CCO[C@@H]1[C@@H](Cc2ccccc2)COC[C@H](NC(=O)OC(C)(C)C)C(=O)O[C@H]1C] |
| 80 | 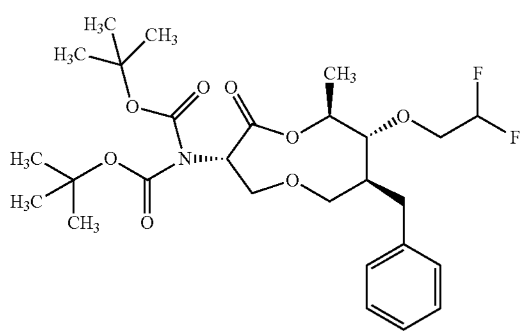 [SMILES: C[C@@H]1OC(=O)[C@@H](N(C(=O)OC(C)(C)C)C(=O)OC(C)(C)C)COC[C@H](Cc2ccccc2)[C@H]1OCC(F)F] |
| 81 | 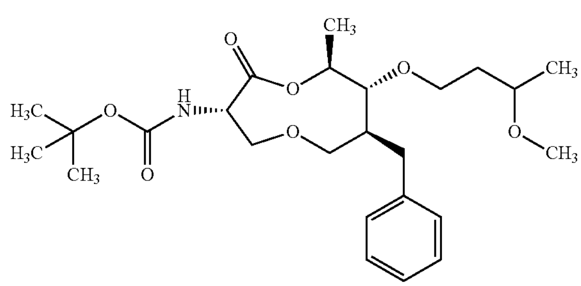 [SMILES: COC(C)CCO[C@@H]1[C@@H](Cc2ccccc2)COC[C@H](NC(=O)OC(C)(C)C)C(=O)O[C@H]1C] |

TABLE 1-continued

Compound Structure

| Compound No. | Structure |
| --- | --- |
| 82 | |
| 83 | |
| 84 | |
| 85 | |
| 86 | |

TABLE 1-continued
Compound Structure
| Compound No. | Structure |
|---|---|
| 87 | 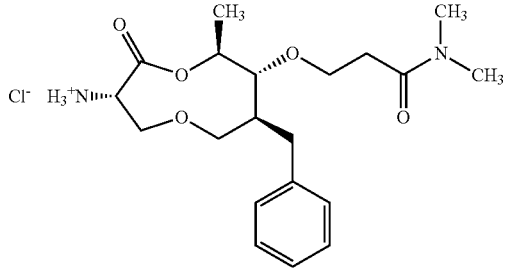 |
| 88 | 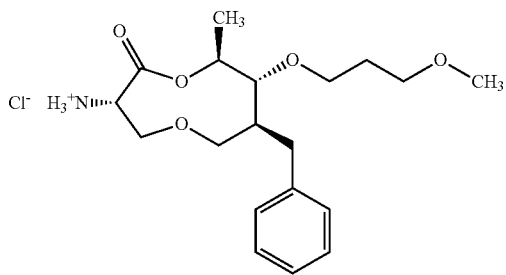 |
| 89 | 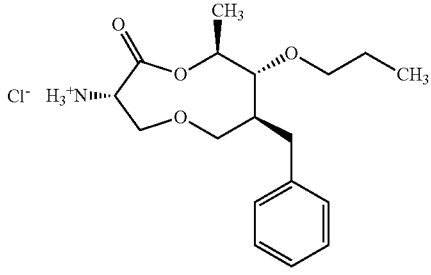 |
| 90 | 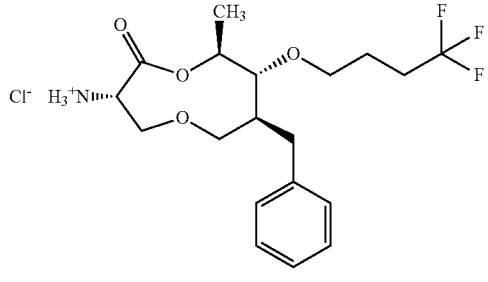 |
| 91 | 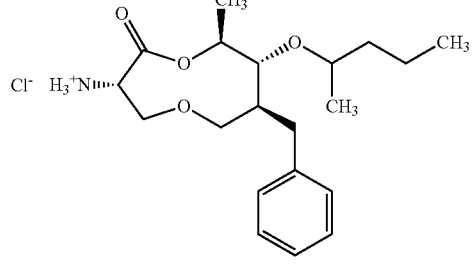 |

103
TABLE 1-continued
Compound Structure
| Compound No. | Structure |
|---|---|
| 92 | 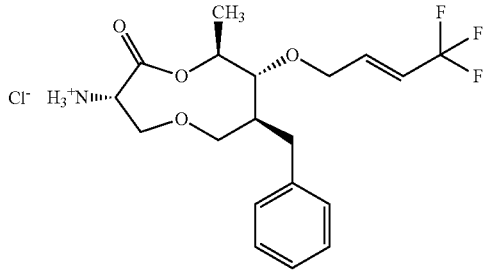 |
| 93 | 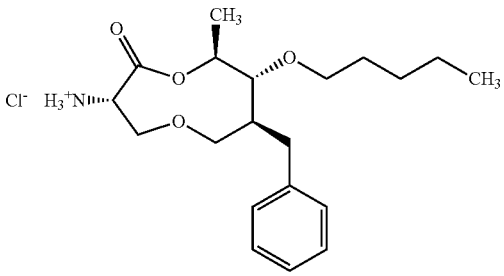 |
| 94 | 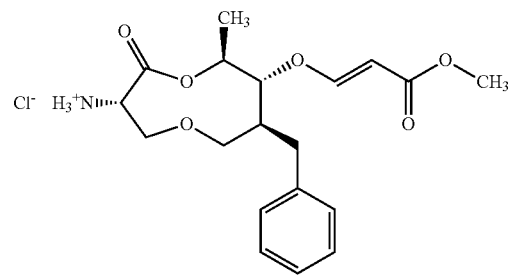 |
| 95 | 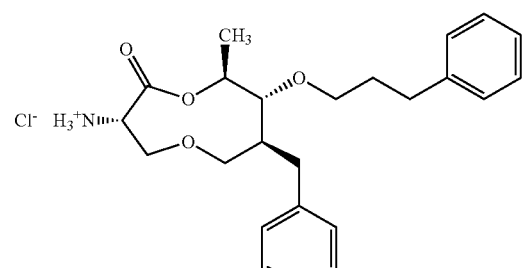 |
| 96 | 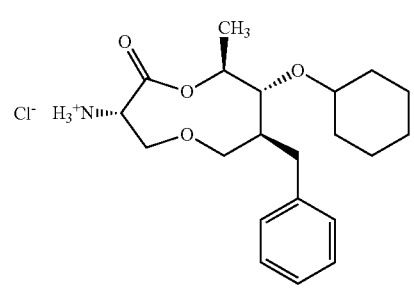 |

TABLE 1-continued

Compound Structure

| Compound No. | Structure |
|---|---|
| 97 | |
| 98 | |
| 99 | |
| 100 | |
| 101 | |

TABLE 1-continued

| Compound No. | Structure |
|---|---|
| 102 | *(chemical structure)* |
| 103 | *(chemical structure)* |
| 104 | *(chemical structure)* |
| 105 | *(chemical structure)* |
| 106 | *(chemical structure)* |

TABLE 1-continued
| Compound No. | Structure |
|---|---|
| 107 | 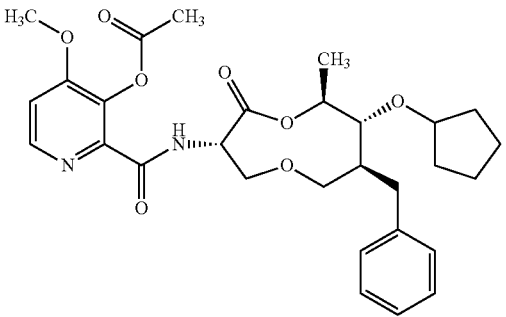 [SMILES: COc1ccnc(C(=O)N[C@H]2COC[C@H](Cc3ccccc3)[C@@H](OC3CCCC3)[C@H](C)OC2=O)c1OC(C)=O] |
| 108 | 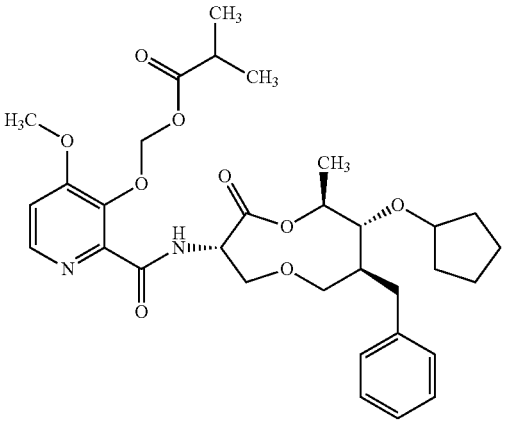 [SMILES: COc1ccnc(C(=O)N[C@H]2COC[C@H](Cc3ccccc3)[C@@H](OC3CCCC3)[C@H](C)OC2=O)c1OCOC(=O)C(C)C] |
| 109 | 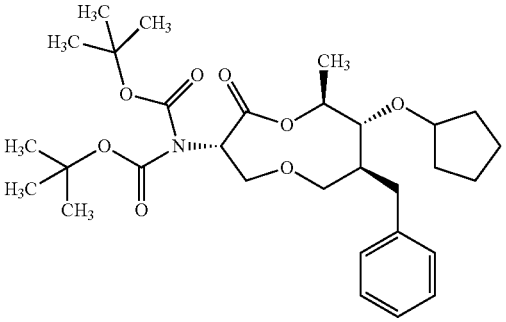 [SMILES: C[C@@H]1OC(=O)[C@@H](N(C(=O)OC(C)(C)C)C(=O)OC(C)(C)C)COC[C@H](Cc2ccccc2)[C@H]1OC1CCCC1] |
| 110 | 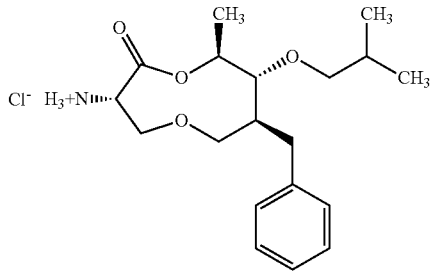 |

TABLE 1-continued

Compound Structure

| Compound No. | Structure |
|---|---|
| 111 | (chemical structure: bicyclic lactone with CH₃, cyclopentyloxy, benzyl substituents, and Cl⁻ ⁺H₃N— group) |

TABLE 2

Compound Appearance and Preparation

| Compound No. | Appearance | Prepared as described in: | Precursor |
|---|---|---|---|
| 1 | White solid | Example 2, Steps 5-6 | 104 |
| 2 | White crystalline solid | Example 2 | — |
| 3 | White solid | Example 2, Step 7 | 2 |
| 4 | White solid | Example 14 | — |
| 5 | Colorless oil | Example 2, Step 7 | 4 |
| 6 | White solid | Example 2, Step 6 | 85 |
| 7 | White foam | Example 2, Step 7 | 2 |
| 8 | White foam | Example 2, Step 7 | 2 |
| 9 | White foam | Example 13 | 2 |
| 10 | White foam | Example 14 | 2 |
| 11 | Colorless film | Example 2, Steps 5-6 | 50 |
| 12 | Colorless film | Example 2, Step 7 | 11 |
| 13 | Sticky white solid | Example 2, Steps 5-6 | 53 |
| 14 | Sticky solid | Example 2, Steps 5-6 | 54 |
| 15 | Colorless oil | Example 2, Step 7 | 13 |
| 16 | Colorless oil | Example 2, Step 7 | 14 |
| 17 | White solid | Example 2, Steps 5-6 | 68 |
| 18 | Colorless oil | Example 2, Steps 5-6 | 69 |
| 19 | White solid | Example 2, Steps 5-6 | 70 |
| 20 | Colorless oil | Example 2, Steps 5-6 | 66 |
| 21 | White solid | Example 2, Steps 5-6 | 72 |
| 22 | White foam | Example 2, Step 7 | 17 |
| 23 | White foam | Example 2, Step 7 | 18 |
| 24 | White foam | Example 2, Step 7 | 19 |
| 25 | Colorless oil | Example 2, Step 7 | 20 |
| 26 | White foam | Example 2, Step 7 | 21 |
| 27 | Amorphous solid | Example 2, Steps 5-6 | 64 |
| 28 | White solid | Example 2, Steps 5-6 | 59 |
| 29 | White solid | Example 2, Steps 5-6 | 60 |
| 30 | White powder | Example 2, Steps 5-6 | 61 |
| 31 | White powder | Example 2, Steps 5-6 | 62 |
| 32 | Amorphous white solid | Example 2, Steps 5-6 | 74 |
| 33 | Amorphous white solid | Example 2, Steps 5-6 | 73 |
| 34 | White solid | Example 2, Step 7 | 28 |
| 35 | Fluffy white solid | Example 2, Step 7 | 29 |
| 36 | Amorphous white solid | Example 2, Step 7 | 27 |
| 37 | Amorphous white solid | Example 2, Step 7 | 30 |
| 38 | Amorphous white solid | Example 2, Step 7 | 31 |
| 39 | Amorphous white solid | Example 2, Step 7 | 32 |
| 40 | Amorphous white solid | Example 2, Step 7 | 33 |
| 41 | Amorphous white solid | Example 2, Steps 5-6 | 79 |
| 42 | Colorless oil | Example 2, Step 7 | 41 |
| 43 | Sticky white solid | Example 2, Steps 5-6 | 80 |
| 44 | Sticky white solid | Example 2, Step 7 | 43 |
| 45 | Sticky colorless solid | Example 2, Steps 5-6 | 81 |
| 46 | Colorless oil | Example 2, Step 7 | 45 |
| 47 | Amorphous white solid | Example 1 | — |
| 48 | Amorphous white solid | Example 4 | — |
| 49 | White crystalline solid | Example 5 | — |
| 50 | Clear colorless foam | Example 5 | — |
| 51 | Amorphous white solid | Example 6 | — |
| 52 | — | Example 6 | — |
| 53 | White solid | Example 7 | — |
| 54 | Colorless goo | Example 6 | — |
| 55 | Colorless oil | Example 2 | — |
| 56 | Yellow oil | Example 2, Step 3 | 57 |
| 57 | White solid | Example 2 | — |
| 58 | Sticky yellow solid | Example 2, Step 3 | 57 |
| 59 | Clear, colorless oil | Example 2, Step 4 | 56 |
| 60 | White solid | Example 2, Step 4 | 58 |
| 61 | White solid | Example 4, Step 2 | 57 |
| 62 | White solid | Example 4, Step 2 | 57 |
| 63 | Oily white solid | Example 6 | — |
| 64 | Amorphous white solid | Example 8 | — |
| 65 | White solid | Example 2, Step 3 | 57 |
| 66 | Pinkish solid | Example 2, Step 3 | 57 |
| 67 | Yellow solid | Example 2, Step 3 | 57 |
| 68 | White solid | Example 2, Step 4 | 65 |
| 69 | White solid | Example 2, Step 4 | 66 |
| 70 | Colorless oil | Example 2, Step 4 | 67 |
| 71 | Yellowish solid | Example 2, Step 3 | 57 |
| 72 | White solid | Example 2, Step 4 | 71 |
| 73 | Amorphous yellow | Example 10 | — |

TABLE 2-continued

Compound Appearance and Preparation

| Compound No. | Appearance | Prepared as described in: | Precursor |
|---|---|---|---|
| | solid | | |
| 74 | — | Example 3 | — |
| 75 | — | Example 8 | — |
| 76 | — | Example 8 | — |
| 77 | Oil | Example 9 | — |
| 78 | — | Example 11 | — |
| 79 | Oil | Example 9 | — |
| 80 | Amorphous white solid | Example 11 | — |
| 81 | Oil | Example 8 | — |
| 82 | White solid | Example 2 | — |
| 83 | White crystalline solid | Example 2 | — |
| 84 | White solid | Example 2, Step 5 | 104 |
| 85 | White solid | Example 2, Step 5 | 82 |
| 86 | — | Example 2, Step 5 | 50 |
| 87 | — | Example 2, Step 5 | 53 |
| 88 | — | Example 2, Step 5 | 54 |
| 89 | White solid | Example 2, Step 5 | 68 |
| 90 | White solid | Example 2, Step 5 | 69 |
| 91 | White solid | Example 2, Step 5 | 70 |
| 92 | White solid | Example 2, Step 5 | 66 |
| 93 | White solid | Example 2, Step 5 | 72 |
| 94 | — | Example 2, Step 5 | 49 |
| 95 | — | Example 2, Step 5 | 59 |
| 96 | — | Example 2, Step 5 | 60 |
| 97 | — | Example 2, Step 5 | 61 |
| 98 | — | Example 2, Step 5 | 62 |
| 99 | White solid | Example 2, Step 5 | 74 |
| 100 | — | Example 2, Step 5 | 73 |
| 101 | — | Example 2, Step 5 | 79 |
| 102 | — | Example 2, Step 5 | 80 |
| 103 | — | Example 2, Step 5 | 81 |
| 104 | White foam | Example 4 | — |
| 105 | Thick, pale-yellow oil | Example 2, Steps 5, 6 | 109 |
| 106 | Thick yellow oil | Example 2, Step 7 | 105 |
| 107 | Colorless solid | Example 13 | 105 |
| 108 | Thick, colorless oil | Example 13 | 105 |
| 109 | Colorless oil | Example 2, Steps 3, 4 | — |
| 110 | — | Example 2, Step 5 | 83 |
| 111 | White solid | Example 2, Step 5 | 109 |

TABLE 3

Analytical Data

| Cmpd No.* | MP (° C.) | IR (cm$^{-1}$) | MASS | $^1$H NMR* | $^{13}$C NMR* |
|---|---|---|---|---|---|
| 1 | 66-70 | — | ESIMS m/z 501.4 ([M + H]$^+$) | $^1$H NMR (CDCl$_3$) δ 11.91 (s, 1H), 8.55 (d, J = 8.3 Hz, 1H), 7.98 (d, J = 5.2 Hz, 1H), 7.33-7.26 (m, 2H), 7.20 (dd, J = 8.6, 5.9 Hz, 1H), 7.14 (d, J = 6.9 Hz, 2H), 6.86 (d, J = 5.2 Hz, 1H), 5.18-4.93 (m, 3H), 4.03 (dd, J = 11.7, 7.2 Hz, 1H), 3.93 (s, 3H), 3.62 (d, J = 9.5 Hz, 1H), 3.57-3.46 (m, 2H), 2.74 (dd, J = 13.9, 3.6 Hz, 1H), 2.60 (dt, J = 14.0, 7.0 Hz, 1H), 2.35-2.22 (m, 1H), 2.12 (m, 1H), 1.36 (d, J = 6.3 Hz, 3H), 1.22 (dd, J = 7.0, 0.8 Hz, 6H) | — |
| 2 | 126-128 | — | — | $^1$H NMR (CDCl$_3$) δ 11.94 (s, 1H), 8.53 (d, J = 8.3 Hz, 1H), 7.98 (d, J = 5.2 Hz, 1H), 7.29 (dd, J = 9.1, 5.8 Hz, 2H), 7.20 (dd, J = 7.0, 4.7 Hz, 3H), 6.85 (d, J = 5.2 Hz, 1H), 5.09-4.92 (m, 2H), 4.02 (dd, J = 11.7, 7.3 Hz, 1H), 3.93 (s, 3H), 3.55-3.40 (m, 4H), 3.40-3.29 (m, 1H), 3.21-3.09 (m, 2H), 2.41-2.25 (m, 1H), 2.07-1.80 (m, 2H), 1.51 (d, J = 6.4 Hz, 3H), 0.96 (d, J = 6.7 Hz, 6H) | $^{13}$C NMR (CDCl$_3$) δ 171.6, 169.3, 155.7, 149.1, 141.1, 140.3, 130.5, 129.6 (2), 128.9 (2), 126.6, 110.0, 84.9, 79.8, 76.4, 72.7, 72.5, 56.5, 51.8, 47.9, 35.5, 29.6, 20.0 (2), 19.3 |
| 3 | 54-58 | — | ESIMS m/z 609.0 ([M + Na]$^+$) | $^1$H NMR (CDCl$_3$) δ 8.44 (d, J = 8.1 Hz, 1H), 8.25 (d, J = 5.3 Hz, 1H), 7.36-7.10 (m, 5H), 6.92 (d, J = 5.4 Hz, 1H), 5.74 (s, 2H), 5.00 (dt, J = 13.7, 6.9 Hz, 2H), 4.01 (dd, J = 11.6, 7.4 Hz, 1H), | — |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | | | 3.87 (s, 3H), 3.53-3.25 (m, 5H), 3.21-3.03 (m, 2H), 2.59-2.44 (m, 1H), 2.32 (t, J = 12.7 Hz, 1H), 1.95-1.84 (m, 2H), 1.49 (d, J = 6.3 Hz, 3H), 1.12 (d, J = 7.0 Hz, 6H), 0.95 (d, J = 6.7 Hz, 6H) | |
| 4 | 89-92 | — | — | ¹H NMR (CDCl₃) δ 11.97 (s, 1H), 8.60 (d, J = 8.2 Hz, 1H), 7.99 (d, J = 5.2 Hz, 1H), 6.86 (d, J = 5.2 Hz, 1H), 5.07-4.85 (m, 2H), 4.07 (dd, J = 11.7, 7.1 Hz, 1H), 3.93 (s, 3H), 3.60 (dd, J = 10.3, 3.3 Hz, 2H), 3.57-3.45 (m, 1H), 3.35 (dd, J = 8.3, 6.3 Hz, 1H), 3.23 (dd, J = 8.3, 6.6 Hz, 1H), 2.96 (t, J = 9.0 Hz, 1H), 1.91-1.53 (m, 9H), 1.45 (d, J = 6.4 Hz, 3H), 1.37-1.08 (m, 6H), 0.92 (dd, J = 6.7, 3.3 Hz, 6H) | ¹³C NMR (CDCl₃) δ 171.0, 169.9, 155.3, 148.7, 140.6, 130.3, 125.5, 109.6, 85.0, 79.0, 76.1, 72.6, 56.1, 51.8, 42.7, 36.4, 34.9, 32.5, 30.3, 29.2, 26.6, 26.5, 26.2, 19.6, 19.5, 18.9 |
| 5 | — | — | ESIMS m/z 593.42 ([M + H]⁺) | ¹H NMR (CDCl₃) δ 8.51 (d, J = 8.2 Hz, 1H), 8.27 (d, J = 5.3 Hz, 1H), 6.93 (d, J = 5.4 Hz, 1H), 5.80-5.71 (m, 2H), 5.07-4.88 (m, 2H), 4.06 (dd, J = 11.7, 7.2 Hz, 1H), 3.88 (s, 3H), 3.62-3.45 (m, 3H), 3.35 (dd, J = 8.3, 6.3 Hz, 1H), 3.27-3.19 (m, 1H), 2.95 (t, J = 9.1 Hz, 1H), 2.54 (dt, J = 14.0, 7.0 Hz, 1H), 1.89-1.52 (m, 8H), 1.44 (d, J = 6.4 Hz, 3H), 1.37-1.16 (m, 4H), 1.13 (d, J = 6.9 Hz, 6H), 1.06-0.95 (m, 2H), 0.92 (dd, J = 6.7, 3.6 Hz, 6H), 0.87-0.70 (m, 1H) | ¹³C NMR (CDCl₃) δ 176.26, 171.70, 163.17, 160.21, 145.66, 144.17, 141.88, 109.62, 89.79, 84.94, 78.92, 75.88, 74.45, 72.71, 56.14, 52.01, 42.67, 36.41, 34.97, 34.92, 33.86, 32.50, 29.14, 26.62, 26.48, 26.19, 19.56, 19.48, 18.89, 18.68 (2) |
| 6 | 96-104 | — | — | ¹H NMR (CDCl₃) δ 11.94 (s, 1H), 7.98 (d, J = 5.2 Hz, 1H), 7.33-7.27 (m, 2H), 7.20 (t, J = 6.6 Hz, 3H), 6.86 (d, J = 5.3 Hz, 1H), 5.10-4.96 (m, 3H), 4.91 (s, 1H), 4.13 (d, J = 11.7 Hz, 1H), 4.04 (dd, J = 11.7, 7.3 Hz, 1H), 3.99 (d, J = 11.8 Hz, 1H), 3.97-3.92 (m, 4H), 3.54-3.37 (m, 3H), 3.30-3.21 (m, 1H), 3.16 (dd, J = 13.6, 3.3 Hz, 1H), 2.43-2.33 (m, 1H), 2.05-1.95 (m, 1H), 1.79 (s, 3H), 1.53 (d, J = 6.5 Hz, 3H) | ¹³C NMR (CDCl₃) δ 171.17, 168.91, 155.34, 148.72, 141.70, 140.65, 139.82, 130.19, 129.21 (2), 128.47 (2), 126.18, 112.24, 109.57, 85.06, 76.44, 75.75, 72.14, 56.10, 51.47, 47.40, 38.63, 35.14, 19.83, 18.85 |
| 7 | — | — | ESIMS m/z 602.51 ([M + H]⁺) | ¹H NMR (CDCl₃) δ 8.48 (d, J = 8.2 Hz, 1H), 8.25 (d, J = 5.3 Hz, 1H), 7.34-7.24 (m, 2H), 7.20 (dd, J = 6.9, 4.0 Hz, 3H), 6.94 (dd, J = 10.6, 5.4 Hz, 1H), 5.80-5.68 (m, 2H), 5.08-4.92 (m, 2H), 4.02 (dd, J = 11.6, 7.4 Hz, 1H), 3.89 (s, 3H), 3.52-3.28 (m, 5H), 3.21-3.10 (m, 2H), 2.37-2.26 (m, | ¹³C NMR (CDCl₃) δ 177.49, 171.63, 162.90, 159.98, 145.34, 144.12, 141.33, 139.82, 129.00 (2), 128.22 (2), 125.88, 109.39, 89.94, 84.33, 79.05, 75.52, 72.04, 71.79, 55.92, 51.52, 47.23, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | | | 1H), 2.01-1.93 (m, 1H), 1.88 (td, J = 13.3, 6.7 Hz, 1H), 1.50 (d, J = 6.4 Hz, 3H), 1.15 (s, 9H), 0.96 (d, J = 6.7 Hz, 6H) | 38.73, 34.88, 28.98, 26.76 (3), 19.29 (2), 18.61 |
| 8 | — | — | ESIMS m/z 560.36 ([M + H]$^+$) | $^1$H NMR (CDCl$_3$) δ 8.39 (d, J = 8.2 Hz, 1H), 8.27 (d, J = 5.4 Hz, 1H), 7.34-7.23 (m, 2H), 7.20 (dd, J = 7.2, 4.8 Hz, 3H), 6.95 (d, J = 5.4 Hz, 1H), 5.80-5.64 (m, 2H), 5.13-4.92 (m, 2H), 4.02 (dd, J = 11.7, 7.4 Hz, 1H), 3.90 (s, 3H), 3.54-3.28 (m, 5H), 3.14 (dd, J = 11.7, 6.4 Hz, 2H), 2.40-2.23 (m, 1H), 2.06 (s, 3H), 2.01-1.82 (m, 2H), 1.50 (d, J = 6.4 Hz, 3H), 0.93 (d, J = 6.7 Hz, 6H) | $^{13}$C NMR (CDCl$_3$) δ 171.81, 170.31, 163.18, 160.20, 145.79, 143.93, 142.15, 140.02, 129.21 (2), 128.44 (2), 126.10, 109.69, 89.41, 84.58, 79.26, 75.74, 72.34, 72.16, 56.19, 51.81, 47.45, 35.09, 29.19, 20.88, 19.50 (2), 18.83 |
| 9 | — | — | ESIMS m/z 529.02 ([M]$^+$) | $^1$H NMR (CDCl$_3$) δ 8.56 (d, J = 8.1 Hz, 1H), 8.32 (d, J = 5.5 Hz, 1H), 7.34-7.23 (m, 2H), 7.20 (t, J = 6.7 Hz, 3H), 7.00 (d, J = 5.7 Hz, 1H), 5.05-4.91 (m, 2H), 3.99 (dd, J = 11.7, 7.4 Hz, 1H), 3.90 (s, 3H), 3.51-3.29 (m, 5H), 3.19-3.08 (m, 2H), 2.38 (s, 3H), 2.36-2.25 (m, 1H), 2.02-1.81 (m, 2H), 1.49 (d, J = 6.4 Hz, 3H), 0.96 (d, J = 6.7 Hz, 6H) | $^{13}$C NMR (CDCl$_3$) δ 171.71, 168.88, 162.67, 159.41, 146.75, 141.14, 140.00, 137.50, 129.21 (2), 128.43 (2), 126.10, 109.89, 84.55, 79.19, 75.73, 72.29, 72.09, 56.29, 51.54, 47.39, 35.09, 29.19, 20.73, 19.50 (2), 18.83 |
| 10 | — | — | ESIMS m/z 574.39 ([M + H]$^+$) | $^1$H NMR (CDCl$_3$) δ 8.49 (d, J = 8.4 Hz, 1H), 8.32 (d, J = 5.4 Hz, 1H), 7.33-7.24 (m, 2H), 7.20 (dd, J = 7.2, 5.3 Hz, 3H), 7.00 (d, J = 5.5 Hz, 1H), 5.08-4.91 (m, 3H), 4.01 (dd, J = 11.7, 7.4 Hz, 1H), 3.92 (s, 3H), 3.50-3.42 (m, 3H), 3.37-3.30 (m, 2H), 3.17-3.11 (m, 2H), 2.37-2.29 (m, 1H), 2.00-1.83 (m, 2H), 1.49 (d, J = 6.4 Hz, 3H), 1.41 (d, J = 6.3 Hz, 6H), 0.97-0.93 (m, 6H) | $^{13}$C NMR (CDCl$_3$) δ 171.79, 162.53, 159.38, 152.03, 146.81, 141.44, 140.03, 137.78, 129.20 (2), 128.43 (2), 126.09, 110.03, 84.53, 79.27, 75.68, 73.76, 72.31, 71.92, 56.32, 51.44, 47.43, 35.09, 29.19, 21.71 (2), 19.50 (2), 18.79 |
| 11 | — | — | ESIMS m/z 517.3 ([M + H]$^+$) | $^1$H NMR (CDCl$_3$) δ 11.93 (d, J = 0.5 Hz, 1H), 8.53 (d, J = 8.3 Hz, 1H), 7.98 (d, J = 5.2 Hz, 1H), 7.34-7.27 (m, 2H), 7.23-7.16 (m, 3H), 6.86 (d, J = 5.1 Hz, 1H), 5.04-4.95 (m, 2H), 4.06-3.95 (m, 2H), 3.93 (s, 3H), 3.84 (dt, J = 8.9, 6.1 Hz, 1H), 3.69 (s, 3H), 3.54-3.39 (m, 3H), 3.21 (t, J = 9.1 Hz, 1H), 3.13 (dd, J = 13.6, 3.4 Hz, 1H), 2.80 (s, 4H), 2.61 (t, J = 6.2 Hz, 2H), 2.36 (dd, J = 13.5, 11.8 Hz, 1H), 2.02-1.90 (m, 1H), 1.52 (d, J = 6.4 Hz, 3H) | $^{13}$C NMR (100 MHz, CDCl$_3$) δ 171.72, 171.12, 168.91, 155.35, 148.73, 140.63, 139.72, 130.20, 129.17, 128.47, 126.18, 109.57, 85.19, 75.64, 72.34, 72.17, 67.70, 56.09, 51.82, 51.48, 47.20, 38.62, 35.25, 35.09, 18.71 |
| 12 | — | — | HRMS-ESI (m/z) [M + H]$^+$ calc'd for C$_{29}$H$_{37}$N$_2$O$_{11}$, | $^1$H NMR (CDCl$_3$) δ 8.38 (d, J = 8.2 Hz, 1H), 8.26 (d, J = 5.4 Hz, 1H), 7.34-7.25 (m, 3H), 7.20 (dd, | $^{13}$C NMR (100 MHz, CDCl$_3$) δ 171.76, 171.73, 170.26, 163.18, |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | | 589.2392; found, 589.2396 | J = 10.3, 4.4 Hz, 3H), 6.94 (d, J = 5.4 Hz, 1H), 5.71 (s, 2H), 5.08-4.89 (m, 2H), 4.07-3.95 (m, 2H), 3.90 (s, 3H), 3.86-3.79 (m, 1H), 3.69 (s, 3H), 3.52-3.35 (m, 3H), 3.19 (t, J = 9.1 Hz, 1H), 3.12 (dd, J = 13.6, 3.3 Hz, 1H), 2.61 (t, J = 6.1 Hz, 2H), 2.34 (dd, J = 13.5, 11.8 Hz, 1H), 2.05 (s, 3H), 2.00-1.90 (m, 1H), 1.51 (d, J = 6.4 Hz, 3H) | 160.21, 145.78, 143.94, 142.14, 139.81, 129.18, 128.44, 126.13, 109.72, 89.41, 85.18, 75.45, 72.34, 72.11, 67.61, 56.20, 51.80, 47.20, 35.27, 35.12, 20.86, 18.72 |
| 13 | — | (Thin film) 3366, 2937, 1746, 1640, 1577, 1528, 1481, 1399, 1202, 1140, 911, 727 | HRMS-ESI (m/z) [M + Na]⁺ calc'd for $C_{27}H_{35}N_3O_8Na$, 552.2316; found, 552.2331. | ¹H NMR (CDCl₃) δ 11.94 (d, J = 0.5 Hz, 1H), 8.54 (d, J = 8.1 Hz, 1H), 7.98 (d, J = 5.2 Hz, 1H), 7.32-7.27 (m, 3H), 7.23-7.14 (m, 3H), 6.86 (d, J = 5.2 Hz, 1H), 5.01 (ddd, J = 15.3, 8.7, 5.6 Hz, 2H), 4.10-3.97 (m, 2H), 3.93 (s, 3H), 3.91-3.83 (m, 1H), 3.55 (d, J = 9.9 Hz, 1H), 3.50-3.40 (m, 2H), 3.21 (t, J = 9.1 Hz, 1H), 3.14 (dd, J = 13.6, 3.6 Hz, 1H), 3.03 (s, 3H), 2.94 (s, 3H), 2.62 (dd, J = 11.0, 6.6 Hz, 2H), 2.42-2.27 (m, 1H), 2.00 (s, 1H), 1.64-1.47 (m, 25H) | ¹³C NMR (CDCl₃) δ 171.05, 170.47, 168.89, 155.33, 148.72, 140.62, 139.82, 130.20, 129.13, 128.46, 126.14, 109.54, 85.40, 77.22, 75.75, 72.85, 72.40, 68.78, 56.08, 51.62, 47.19, 38.62, 37.35, 35.38, 35.15, 33.78, 18.79 |
| 14 | — | (Thin film) 3363, 2925, 2876, 1746, 1648, 1576, 1529, 1481, 1452, 1389, 1327, 1190, 1086, 911, 731 | HRMS-FAB (m/z) [M + Na]⁺ calc'd for $C_{26}H_{34}N_2O_8Na$, 525.2207; found, 525.2219 | ¹H NMR (CDCl₃) δ 11.94 (s, 1H), 8.54 (d, J = 8.3 Hz, 1H), 7.98 (d, J = 5.2 Hz, 1H), 7.34-7.27 (m, 2H), 7.24-7.17 (m, 3H), 6.86 (d, J = 5.2 Hz, 1H), 5.01 (dt, J = 15.5, 4.8 Hz, 2H), 4.02 (dd, J = 11.7, 7.3 Hz, 1H), 3.94 (s, 3H), 3.85-3.73 (m, 1H), 3.70-3.60 (m, 1H), 3.55-3.39 (m, 5H), 3.31 (s, 3H), 3.21-3.08 (m, 2H), 2.44-2.27 (m, 1H), 1.98 (s, 1H), 1.87 (p, J = 6.1 Hz, 2H), 1.51 (d, J = 6.4 Hz, 3H) | ¹³C NMR (100 MHz, CDCl₃) δ 171.13, 168.90, 155.33, 148.72, 140.63, 139.86, 130.20, 129.17, 128.47, 126.15, 109.55, 84.92, 77.22, 75.83, 72.55, 72.23, 69.21, 69.17, 58.66, 56.09, 51.52, 47.25, 35.07, 30.47, 18.72 |
| 15 | — | (Thin film) 3373, 2933, 2881, 1750, 1674, 1632, 1580, 1506, 1455, 1384, 1312, 1202, 1083, 1058, 1004, 970, 831, 730 | HRMS-ESI (m/z) [M + Na]⁺ calc'd for $C_{30}H_{39}N_3O_{10}Na$, 624.2528; found, 624.2539 | ¹H NMR (CDCl₃) δ 8.40 (d, J = 8.1 Hz, 1H), 8.26 (d, J = 5.4 Hz, 1H), 7.33-7.24 (m, 2H), 7.19 (t, J = 6.6 Hz, 3H), 6.94 (d, J = 5.4 Hz, 1H), 5.72 (s, 2H), 5.13-4.88 (m, 2H), 4.11-3.94 (m, 2H), 3.90 (s, 3H), 3.89-3.82 (m, 1H), 3.53 (d, J = 10.1 Hz, 1H), 3.49-3.39 (m, 2H), 3.20 (t, J = 9.1 Hz, 1H), 3.14 (dd, J = 13.9, 3.5 Hz, 1H), 3.03 (s, 3H), 2.94 (s, 3H), 2.69-2.53 (m, 3H), 2.41-2.27 (m, 1H), 2.05 (s, 3H), 2.02-1.92 (m, 1H), 1.62 (s, 4H), 1.52 (d, J = 6.4 Hz, 3H) | ¹³C NMR (100 MHz, CDCl₃) δ 171.69, 170.51, 170.30, 163.17, 160.20, 145.78, 143.95, 142.14, 139.89, 129.14, 128.43, 126.09, 109.69, 89.42, 85.38, 75.56, 72.57, 68.69, 56.19, 53.77, 51.92, 47.18, 37.36, 35.37, 35.19, 33.80, 29.27, 20.87, 18.82 |
| 16 | — | (Thin film) 3372, 2929, 2877, 1752, | HRMS-ESI (m/z) [M + H]⁺ calc'd for | ¹H NMR (CDCl₃) δ 8.40 (d, J = 8.2 Hz, 1H), 8.27 (d, J = 5.4 Hz, 1H), | ¹³C NMR (101 MHz, CDCl₃) δ 171.77, 170.30, |

TABLE 3-continued

Analytical Data

| Cmpd No.* | MP (° C.) | IR (cm⁻¹) | MASS | ¹H NMR* | ¹³C NMR* |
|---|---|---|---|---|---|
|  |  | 1677, 1578, 1505, 1455, 1311, 1276, 1242, 1087, 1044, 1004, 969, 830, 731 | C₂₉H₃₈N₂O₁₀Na, 597.2419; found, 597.2427 | 7.35-7.24 (m, 2H), 7.20 (dd, J = 7.1, 4.5 Hz, 3H), 6.94 (d, J = 5.4 Hz, 1H), 5.72 (s, 2H), 5.13-4.90 (m, 2H), 4.01 (dd, J = 11.7, 7.4 Hz, 1H), 3.90 (s, 3H), 3.78 (dt, J = 8.5, 6.3 Hz, 1H), 3.64 (dt, J = 8.6, 6.3 Hz, 1H), 3.57-3.36 (m, 5H), 3.31 (s, 3H), 3.21-3.08 (m, 2H), 2.38-2.26 (m, 1H), 2.06 (s, 3H), 2.02-1.91 (m, 1H), 1.87 (p, J = 6.2 Hz, 2H), 1.50 (d, J = 6.4 Hz, 3H) | 163.17, 160.20, 145.79, 143.94, 142.13, 139.94, 129.18, 128.44, 126.11, 109.69, 89.41, 84.90, 75.64, 72.39, 72.30, 69.19, 69.11, 58.66, 56.19, 51.83, 47.25, 35.09, 30.47, 20.88, 18.74 |
| 17 | 102-104 | — | ESIMS m/z 474 ([M + H]⁺) | ¹H NMR (CDCl₃) δ 11.98-11.95 (s, 2H), 8.59-8.54 (d, J = 8.3 Hz, 2H), 8.03-7.99 (d, J = 5.2 Hz, 2H), 7.35-7.29 (m, 4H), 7.28-7.17 (m, 7H), 6.90-6.86 (d, J = 5.2 Hz, 2H), 5.09-4.99 (m, 5H), 4.09-4.02 (dd, J = 11.7, 7.3 Hz, 2H), 4.02-3.94 (s, 6H), 3.72-3.65 (dt, J = 8.3, 6.6 Hz, 2H), 3.59-3.52 (m, 5H), 3.52-3.43 (m, 5H), 3.23-3.16 (m, 5H), 2.85-2.81 (s, 2H), 2.40-2.33 (t, J = 12.7 Hz, 2H), 2.03-1.96 (dt, J = 8.2, 5.8 Hz, 2H), 1.72-1.63 (h, J = 7.1 Hz, 12H), 1.63-1.59 (s, 3H), 1.33-1.27 (s, 1H), 1.03-0.94 (t, J = 7.4 Hz, 6H) | ¹³C NMR (CDCl₃) δ 171.14, 168.90, 155.34, 148.73, 140.62, 139.90, 130.22, 129.17, 128.46, 126.14, 109.56, 84.92, 77.22, 77.01, 76.80, 75.94, 74.43, 72.22, 56.08, 51.53, 47.38, 35.16, 23.50, 18.78, 10.71 |
| 18 | — | — | ESIMS m/z 542 ([M + H]⁺) | ¹H NMR (CDCl₃) δ 11.95 (s, 1H), 8.55 (d, J = 8.3 Hz, 1H), 8.01 (d, J = 5.2 Hz, 1H), 7.33 (t, J = 7.5 Hz, 2H), 7.27-7.19 (m, 3H), 6.89 (d, J = 5.2 Hz, 1H), 5.07-4.98 (m, 2H), 4.06 (dd, J = 11.8, 7.3 Hz, 1H), 3.96 (s, 3H), 3.80-3.73 (m, 1H), 3.67-3.60 (m, 1H), 3.56-3.42 (m, 3H), 3.23 (t, J = 8.9 Hz, 1H), 3.09 (dd, J = 13.7, 3.6 Hz, 1H), 2.40 (d, J = 13.5 Hz, 1H), 2.30-2.20 (m, 2H), 2.01 (dt, J = 8.8, 5.7 Hz, 1H), 1.89 (dt, J = 16.2, 6.2 Hz, 3H), 1.53 (d, J = 6.4 Hz, 3H) | ¹³C NMR (CDCl₃) δ 171.12, 168.92, 155.36, 148.74, 140.64, 139.52, 130.19, 129.09, 128.53, 126.29, 109.58, 85.12, 75.51, 72.19, 70.61, 56.09, 51.48, 47.23, 38.62, 35.26, 23.02, 18.80 |
| 19 | 52-56 | — | ESIMS m/z 500 ([M]⁻) | (1:1 mixture of diastereomers); ¹H NMR (CDCl₃) δ 11.98 (s, 1H), 8.54 (d, J = 6.3 Hz, 1H), 8.01 (d, J = 5.2 Hz, 1H), 7.35-7.19 (m, 5H), 6.88 (d, J = 5.2 Hz, 1H), 5.11-5.02 (m, 1H), 4.99-4.92 (m, 1H), 4.10 (dt, J = 12.0, 6.1 Hz, 1H), 3.96 (s, 3H), 3.66 (dtd, J = 18.2, 12.2, 6.2 Hz, 1H), 3.56-3.45 (m, 2H), 3.45-3.31 (m, 2H), 3.23 (ddd, J = 13.5, 10.0, 3.6 Hz, 1H), 2.36 (dt, J = 42.3, 12.9 Hz, 1H), | ¹³C NMR (CDCl₃) δ 171.22, 168.89, 155.34, 148.73, 140.60, 140.41, 140.28, 130.25, 129.13, 128.46, 128.44, 126.10, 126.05, 109.54, 81.38, 81.15, 76.44, 76.18, 73.36, 72.45, 56.08, 51.76, 47.85, 47.42, 39.31, 38.93, 35.15, 35.06, 19.95, 19.70, 18.91, 18.84, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | | | 1.98-1.90 (m, 1H), 1.71-1.58 (m, 1H), 1.53 (t, J = 6.8 Hz, 4H), 1.52-1.27 (m, 3H), 1.22 (dd, J = 8.6, 6.2 Hz, 3H), 0.96 (dt, J = 11.6, 7.2 Hz, 3H) | 18.80, 14.27 |
| 20 | — | — | ESIMS m/z 540 ([M + H]$^+$) | $^1$H NMR (600 MHz, CDCl$_3$) δ 11.93 (s, 1H), 8.56 (d, J = 8.3 Hz, 1H), 8.01 (d, J = 5.2 Hz, 1H), 7.35-7.31 (m, 2H), 7.26-7.22 (m, 1H), 7.21 (d, J = 7.2 Hz, 2H), 6.89 (d, J = 5.2 Hz, 1H), 6.43 (dtd, J = 15.7, 3.8, 2.0 Hz, 1H), 6.06-5.97 (m, 1H), 5.12-4.99 (m, 2H), 4.37 (ddd, J = 15.1, 5.9, 3.0 Hz, 1H), 4.25 (ddd, J = 15.2, 5.9, 3.0 Hz, 1H), 4.08 (dd, J = 11.7, 7.4 Hz, 1H), 3.96 (s, 3H), 3.59-3.43 (m, 3H), 3.32 (t, J = 9.0 Hz, 1H), 3.07 (dd, J = 13.7, 3.7 Hz, 1H), 2.44 (dd, J = 13.4, 11.6 Hz, 1H), 2.06 (dt, J = 8.9, 5.6 Hz, 1H), 1.53 (d, J = 6.4 Hz, 3H) | $^{13}$C NMR (CDCl$_3$) δ 171.52, 169.33, 155.76, 149.15, 141.05, 139.68, 136.12, 130.56, 129.48 (2), 128.94 (2), 126.74 (2), 119.11, 110.00, 85.94, 75.68, 72.51, 70.33, 56.49, 51.81, 47.55, 39.01 (2), 35.73, 19.12 |
| 21 | 51-56 | — | ESIMS m/z 502 ([M + H]$^+$) | $^1$H NMR (CDCl$_3$) δ 11.96 (s, 1H), 8.56 (d, J = 8.3 Hz, 1H), 8.01 (d, J = 5.1 Hz, 1H), 7.34-7.30 (m, 2H), 7.25-7.21 (m, 3H), 6.88 (d, J = 5.2 Hz, 1H), 5.07-5.00 (m, 2H), 4.05 (dd, J = 11.7, 7.3 Hz, 1H), 3.96 (s, 3H), 3.74-3.68 (m, 1H), 3.61-3.52 (m, 2H), 3.50-3.43 (m, 2H), 3.21-3.15 (m, 2H), 2.36 (t, J = 12.7 Hz, 1H), 1.99 (d, J = 8.5 Hz, 1H), 1.64 (dt, J = 13.4, 6.4 Hz, 2H), 1.54 (d, J = 6.4 Hz, 3H), 1.43-1.33 (m, 4H), 0.93 (t, J = 7.0 Hz, 3H) | $^{13}$C NMR (CDCl$_3$) δ 171.53, 169.30, 155.74, 149.13, 141.01, 140.30, 130.62, 129.57 (2), 128.85 (2), 126.54, 109.95, 85.37, 76.32, 73.28, 72.62, 56.48, 51.93, 47.76, 35.57, 30.41, 28.75, 22.99, 19.18, 14.41 |
| 22 | — | — | ESIMS m/z 546 ([M + H]$^+$) | $^1$H NMR (CDCl$_3$) δ 8.41 (d, J = 7.7 Hz, 1H), 8.29 (d, J = 4.7 Hz, 1H), 7.31 (t, J = 7.2 Hz, 2H), 7.22 (d, J = 7.2 Hz, 3H), 6.96 (d, J = 4.6 Hz, 1H), 5.74 (s, 2H), 5.04 (dt, J = 26.5, 7.1 Hz, 2H), 4.04 (dd, J = 11.7, 7.4 Hz, 1H), 3.93 (s, 3H), 3.70-3.64 (m, 1H), 3.54 (t, J = 7.5 Hz, 2H), 3.50-3.40 (m, 2H), 3.18 (t, J = 8.4 Hz, 2H), 2.35 (t, J = 12.7 Hz, 1H), 2.08 (s, 3H), 2.03-1.95 (m, 1H), 1.70-1.63 (m, 2H), 1.53 (d, J = 5.9 Hz, 3H), 1.00 (t, J = 7.0 Hz, 3H) | $^{13}$C NMR (CDCl$_3$) δ 172.18, 170.66, 163.58, 160.60, 146.17, 144.32, 142.59, 140.38, 129.59, 128.83, 126.49, 110.09, 89.81, 85.31, 76.14, 74.74, 72.79, 72.68, 56.59, 52.25, 47.78, 35.59, 23.90, 21.26, 19.19, 11.10 |
| 23 | — | — | ESIMS m/z 614 ([M + H]$^+$) | $^1$H NMR (CDCl$_3$) δ 8.38 (d, J = 8.1 Hz, 1H), 8.27 (d, J = 5.4 Hz, 1H), 7.35-7.25 (m, 2H), 7.25-7.16 (m, 3H), 6.94 (d, J = 5.4 Hz, 1H), 5.72 (d, J = 0.7 Hz, 2H), 5.08-4.92 (m, 2H), 4.06-4.00 (m, | $^{13}$C NMR (CDCl$_3$) δ 171.78, 170.29, 163.20, 160.22, 145.79, 143.96, 142.12, 139.61, 129.12, 128.52, 126.25, 109.72, 89.41, 85.09, |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | | | 1H), 3.91 (s, 3H), 3.78-3.70 (m, 1H), 3.64-3.57 (m, 1H), 3.52-3.43 (m, 2H), 3.40 (dd, J = 11.7, 7.3 Hz, 1H), 3.19 (t, J = 9.0 Hz, 1H), 3.09-3.03 (m, 1H), 2.41-2.33 (m, 1H), 2.29-2.16 (m, 2H), 2.06 (s, 3H), 1.97 (m, J = 2.5 Hz, 1H), 1.90-1.81 (m, 2H), 1.49 (d, J = 6.4 Hz, 3H) | 77.22, 75.33, 72.34, 72.09, 70.54, 56.20, 51.79, 47.24, 35.28, 30.78 (q), 22.99, 20.87, 18.81 |
| 24 | — | — | ESIMS m/z 574 ([M + H]⁺) | (1:1 mixture of diastereomers); ¹H NMR (CDCl₃) δ 8.37 (d, J = 7.0 Hz, 1H), 8.27 (d, J = 5.4 Hz, 1H), 7.33-7.25 (m, 2H), 7.23-7.16 (m, 3H), 6.94 (d, J = 5.4 Hz, 1H), 5.75-5.67 (m, 3H), 5.06-4.92 (m, 2H), 4.10-4.03 (m, 1H), 3.90 (s, 3H), 3.68-3.57 (m, 1H), 3.52-3.33 (m, 2H), 3.33-3.25 (m, 1H), 3.25-3.14 (m, 1H), 2.40-2.24 (m, 1H), 2.05 (s, 3H), 1.96-1.83 (m, 1H), 1.69-1.60 (m, 1H), 1.52-1.47 (m, 3H), 1.45-1.30 (m, 3H), 1.23-1.14 (m, 3H), 0.97-0.89 (m, 3H) | ¹³C NMR (CDCl₃) δ 171.86, 170.30, 163.15, 160.21, 145.77, 143.94, 142.20, 140.50, 140.37, 129.15, 128.44, 128.42, 126.05, 126.00, 109.68, 100.00, 89.43, 81.39, 81.16, 77.22, 76.60, 76.52, 76.25, 76.15, 73.14, 72.64, 72.56, 56.19, 52.08, 47.91, 47.46, 39.32, 38.92, 35.19, 35.10, 20.87, 19.98, 19.70, 18.92, 18.85, 18.80, 14.28 |
| 25 | — | — | ESIMS m/z 612 ([M + H]⁺) | ¹H NMR (CDCl₃) δ 8.39 (d, J = 8.2 Hz, 1H), 8.27 (d, J = 5.3 Hz, 1H), 7.35-7.24 (m, 2H), 7.24-7.15 (m, 3H), 6.95 (d, J = 5.4 Hz, 1H), 6.45-6.35 (m, 1H), 6.06-5.92 (m, 1H), 5.72 (d, J = 1.1 Hz, 2H), 5.09-4.96 (m, 2H), 4.39-4.30 (m, 1H), 4.26-4.18 (m, 1H), 4.07-4.01 (m, 1H), 3.91 (s, 3H), 3.55-3.45 (m, 2H), 3.44-3.37 (m, 1H), 3.28 (t, J = 9.0 Hz, 1H), 3.03 (dd, J = 13.6, 3.5 Hz, 1H), 2.46-2.35 (m, 1H), 2.06 (s, 3H), 2.03 (m, 1H), 1.49 (d, J = 6.4 Hz, 3H) | ¹³C NMR (CDCl₃) δ 171.79, 170.30, 163.21, 160.23, 145.80, 143.97, 142.09, 139.37, 129.11, 128.53, 126.31, 118.76 (q), 109.74, 89.40, 85.54, 77.22, 75.11, 72.27, 71.86, 69.88, 56.21, 51.72, 47.16, 38.62, 35.36, 20.87, 18.73 |
| 26 | — | — | ESIMS m/z 572 ([M]⁺) | ¹H NMR (CDCl₃) δ 8.39 (d, J = 8.2 Hz, 1H), 8.26 (d, J = 5.4 Hz, 1H), 7.33-7.26 (m, 2H), 7.24-7.16 (m, 3H), 6.94 (d, J = 5.4 Hz, 1H), 5.72 (s, 2H), 5.07-4.95 (m, 2H), 4.05-3.97 (m, 1H), 3.90 (s, 3H), 3.72-3.64 (m, 1H), 3.59-3.47 (m, 2H), 3.47-3.36 (m, 2H), 3.18-3.11 (m, 2H), 2.36-2.28 (m, 1H), 2.05 (s, 3H), 1.96 (d, J = 8.9 Hz, 1H), 1.65-1.57 (m, 2H), 1.50 (d, J = 6.4 Hz, 3H), 1.39-1.32 (m, 4H), 0.94-0.87 (m, 3H) | ¹³C NMR (CDCl₃) δ 171.80, 170.29, 163.18, 160.21, 145.79, 143.93, 142.17, 139.98, 129.20, 128.44, 126.11, 109.69, 89.42, 84.95, 75.74, 72.81, 72.39, 72.27, 56.20, 51.83, 47.37, 35.19, 30.01, 28.35, 22.59, 20.87, 18.80, 14.02 |
| 27 | 76-84 | (Thin film) 3358, 2948, 1751, 1706 | HRMS-ESI (m/z) [M + H]⁺ calc'd for | ¹H NMR (CDCl₃) δ 11.88 (d, J = 0.5 Hz, 1H), 8.52 (d, J = 8.4 Hz, 1H), | ¹³C NMR (CDCl₃) δ 171.01, 168.94, 167.94, 162.87, |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | 1641, 1577, 1530, 1481, 1437, 1328, 1184, 1130, 909, 729 | $C_{26}H_{31}N_2O_9$, 515.2024; found, 515.2022 | 7.99 (d, J = 5.2 Hz, 1H), 7.49 (d, J = 12.2 Hz, 1H), 7.34-7.27 (m, 2H), 7.25-7.19 (m, 1H), 7.19-7.12 (m, 3H) 6.87 (d, J = 5.1 Hz, 1H), 5.42 (d, J = 12.2 Hz, 1H), 5.15-4.99 (m, 2H), 4.05 (dd, J = 11.7, 7.4 Hz, 1H), 3.94 (s, 3H), 3.84-3.73 (m, 1H), 3.72 (s, 3H), 3.61-3.55 (m, 1H), 3.54-3.43 (m, 3H), 2.95 (dd, J = 13.8, 3.5 Hz, 1H), 2.38 (dd, J = 13.7, 11.3 Hz, 1H), 2.13 (dd, J = 9.2, 5.6 Hz, 1H), 1.44 (d, J = 6.4 Hz, 3H) | 155.38, 148.76, 140.67, 138.47, 130.08, 129.10, 128.60, 126.51, 109.63, 98.58, 88.93, 74.25, 71.98, 71.49, 56.10, 51.26, 46.50, 35.22, 18.75 |
| 28 | — | (Thin film) 3363, 3061, 3026, 2937, 2872, 1746, 1648, 1602, 1576, 1480, 1452, 1439, 1389, 1327, 1280, 1262, 1242, 1202, 1138, 1083, 1053, 908, 849, 728, 699 | HRMS-ESI (m/z) [M + H]⁺ calc'd for $C_{31}H_{37}N_2O_7$, 549.2595; found, 549.2610 | ¹H NMR (CDCl₃) δ 12.00-11.84 (d, J = 0.5 Hz, 1H), 8.60-8.46 (d, J = 8.3 Hz, 1H), 8.01-7.94 (d, J = 5.2 Hz, 1H), 7.34-7.23 (m, 4H), 7.23-7.13 (m, 6H), 6.90-6.80 (d, J = 5.1 Hz, 1H), 5.08-4.93 (m, 2H), 4.08-3.97 (dd, J = 11.7, 7.3 Hz, 1H), 3.97-3.87 (s, 3H), 3.77-3.66 (dt, J = 8.7, 6.4 Hz, 1H), 3.62-3.55 (dt, J = 8.8, 6.5 Hz, 1H), 3.54-3.49 (dd, J = 10.7, 1.4 Hz, 1H), 3.48-3.39 (m, 2H), 3.22-3.07 (m, 2H), 2.78-2.65 (dd, J = 8.8, 6.7 Hz, 2H), 2.42-2.26 (dd, J = 13.6, 11.7 Hz, 1H), 2.05-1.88 (m, 3H), 1.53-1.47 (d, J = 6.4 Hz, 3H) | ¹³C NMR (CDCl₃) δ 171.16, 168.95, 155.39, 148.79, 141.66, 140.63, 139.85, 130.28, 129.18, 128.49, 128.42, 128.35, 126.18, 125.94, 109.60, 85.15, 75.83, 72.55, 72.26, 71.95, 56.09, 51.57, 47.27, 35.25, 32.43, 31.87, 18.84 |
| 29 | — | (Thin film) 3364, 3026, 2933, 2857, 1742, 1649, 1602, 1577, 1528, 1481, 1451, 1379, 1327, 1280, 1261, 1204, 1137, 1069, 907, 849, 799, 728, 700 | HRMS-ESI (m/z) [M + H]⁺ calc'd for $C_{28}H_{37}N_2O_7$, 513.2595; found, 513.2631 | ¹H NMR (CDCl₃) δ 12.06-11.79 (d, J = 0.5 Hz, 1H), 8.62-8.38 (d, J = 8.3 Hz, 1H), 8.11-7.79 (d, J = 5.2 Hz, 1H), 7.33-7.26 (m, 2H), 7.23-7.15 (m, 3H), 6.90-6.81 (d, J = 5.2 Hz, 1H), 5.09-4.97 (dq, J = 13.0, 6.5 Hz, 1H), 4.97-4.87 (dd, J = 1.52, 7.5 Hz, 1H), 4.11-3.99 (dd, J = 11.6, 6.9 Hz, 1H), 3.99-3.86 (s, 3H), 3.75-3.64 (s, 2H), 3.53-3.28 (m, 5H), 3.26-3.14 (dd, J = 13.6, 3.5 Hz, 1H), 2.42-2.24 (m, 1H), 2.08-1.97 (m, 2H), 1.96-1.85 (m, 1H), 1.84-1.72 (m, 2H), 1.63-1.56 (m, 1H), 1.54-1.47 (d, J = 6.5 Hz, 3H), 1.38-1.11 (m, 6H) | ¹³C NMR (CDCl₃) δ 171.26, 168.94, 155.39, 148.79, 140.61, 140.35, 130.32, 129.17, 128.47, 126.09, 109.58, 81.70, 79.63, 76.61, 73.38, 72.46, 67.12, 56.08, 51.80, 47.72, 35.20, 33.30, 33.08, 25.65, 24.76, 24.69, 18.81 |
| 30 | — | (Neat film) 2261, 3062, 3027, 2939, 1752, 1720, 1649, 1577, 1529, 1480, 1451, 1439, 1380, 1326, 1263, 1243, 1200, 1177, 1107, 1069, | HRMS-ESI (m/z) [M + H]⁺ calc'd for $C_{29}H_{31}N_2O_8$, 535.2075; found, 535.2078 | ¹H NMR (CDCl₃) δ 11.93 (s, 1H), 8.59 (d, J = 8.3 Hz, 1H), 8.06 (dd, J = 8.3, 1.3 Hz, 2H), 8.00 (d, J = 5.2 Hz, 1H), 7.68-7.55 (m, 3H), 7.53-7.41 (m, 1H), 7.24 (d, J = 7.5 Hz, 1H), 7.20-7.10 (m, 2H), 6.87 (d, J = 5.2 Hz, 1H), 5.34-5.20 (m, 1H), 5.17-5.05 (m, 1H), | ¹³C NMR (CDCl₃) δ 171.07, 168.93, 165.87, 155.37, 148.77, 140.64, 138.86, 133.52, 130.17, 129.81, 129.37, 128.98, 128.60, 128.51, 126.33, 109.59, 77.67, 74.45, 73.11, 72.68, |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | 1026, 976, 909, 848, 799, 729, 711 | | 4.07 (dd, J = 11.7, 7.2 Hz, 1H), 3.94 (s, 2H), 3.71 (s, 1H), 3.60 (td, J = 11.6, 11.2, 6.6 Hz, 1H), 2.84 (dd, J = 13.4, 3.2 Hz, 1H), 2.42-2.24 (m, 1H), 1.41 (d, J = 5.9 Hz, 2H) | 56.10, 51.78 45.89, 35.10, 18.39 |
| 31 | — | (Neat film) 3361, 3024, 2939, 1727, 1649, 1601, 1577, 1529, 1481, 1453, 1439, 1388, 1327, 1281, 1262, 1242, 1196, 1165, 1117, 1059, 909, 848, 799, 728 | HRMS-FAB (m/z) [M + H]⁺ calc'd for C₂₆H₃₁N₂O₈, 499.2075; found, 499.2081 | ¹H NMR (CDCl₃) δ 11.92 (d, J = 0.6 Hz, 1H), 8.56 (d, J = 8.3 Hz, 1H), 7.99 (d, J = 5.2 Hz, 1H), 7.35-7.27 (m, 2H), 7.24-7.12 (m, 3H), 6.86 (d, J = 5.1 Hz, 1H), 5.19-5.02 (m, 2H), 4.98 (t, J = 9.3 Hz, 1H), 4.02 (dd, J = 11.7, 7.2 Hz, 1H), 3.94 (s, 3H), 3.65 (d, J = 9.7 Hz, 1H), 3.60-3.47 (m, 2H), 2.78 (dd, J = 14.0, 3.7 Hz, 1H), 2.29 (dd, J = 13.9, 11.3 Hz, 1H), 2.20-2.08 (m, 1H), 1.71-1.61 (m, 1H), 1.37 (d, J = 6.3 Hz, 3H), 1.10-1.01 (m, 3H), 0.98-0.85 (m, 3H) | ¹³C NMR (CDCl₃) δ 174.29, 171.02, 168.90, 155.36, 148.75, 140.63, 139.02, 130.16, 129.03, 128.54, 126.36, 109.58, 76.93, 74.42, 72.95, 72.56, 56.09, 51.70, 45.79, 35.00, 18.25, 12.85, 8.70, 8.68 |
| 32 | 57-70 | 3362, 2938, 2833, 1746, 1648, 1576, 1529, 1481, 1439, 1391, 1327, 1281, 1262, 1242, 1194, 1139, 1094, 1052, 909, 849, 730, 701 | HRMS-ESI (m/z) [M + CH₃CNNH₄]⁺ calc'd for C₂₅H₃₅N₄O₇, 503.2500; found, 503.2541 | ¹H NMR (CDCl₃) δ 11.96-11.91 (d, J = 0.6 Hz, 1H), 8.57-8.50 (d, J = 8.3 Hz, 1H), 8.01-7.95 (d, J = 5.2 Hz, 1H), 7.34-7.26 (m, 2H), 7.25-7.17 (m, 3H), 6.89-6.83 (d, J = 5.1 Hz, 1H), 5.33-5.28 (s, 0H), 5.07-4.95 (m, 2H), 4.07-3.98 (dd, J = 11.7, 7.4 Hz, 1H), 3.96-3.90 (s, 3H), 3.57-3.49 (s, 4H), 3.49-3.40 (m, 2H), 3.19-3.12 (dd, J = 13.7, 3.5 Hz, 1H), 3.12-3.05 (t, J = 9.1 Hz, 1H), 2.43-2.32 (dd, J = 13.6, 11.6 Hz, 1H), 2.20-2.15 (s, 0H), 2.02-1.91 (dt, J = 9.1, 5.7 Hz, 1H), 1.56-1.49 (d, J = 6.4 Hz, 3H) | ¹³C NMR (CDCl₃) δ 171.12, 168.90, 155.33, 148.72, 140.63, 139.69, 130.19, 129.18, 128.46, 126.18, 109.56, 86.60, 75.64, 72.31, 72.16, 60.11, 56.08, 51.47, 47.05, 35.21, 18.78 |
| 33 | 65-80 | (Thin film) 3357, 3026, 2937, 1748, 1648, 1597, 1577, 1529, 1491, 1481, 1452, 1391, 1263, 1281, 1263, 1238, 1201, 1136, 1078, 1054, 1030, 909, 848, 799, 751, 730, 692, 648, 623, 600 | HRMS-ESI (m/z) [M + H]⁺ calc'd for C₂₈H₃₁N₂O₇, 507.2126; found, 507.2167 | ¹H NMR (CDCl₃) δ 11.97-11.88 (s, 1H), 8.65-8.47 (d, J = 8.2 Hz, 1H), 8.05-7.92 (d, J = 5.2 Hz, 1H), 7.35-7.23 (m, 6H), 7.22-7.11 (m, 3H), 7.03-6.94 (dd, J = 7.6, 4.3 Hz, 3H), 6.89-6.84 (d, J = 5.2 Hz, 1H), 5.26-5.14 (m, 1H), 5.11-4.99 (q, J = 7.4 Hz, 1H), 4.42-4.28 (t, J = 8.9 Hz, 1H), 4.15-4.03 (dd, J = 11.7, 7.4 Hz, 1H), 3.99-3.88 (s, 3H), 3.65-3.54 (d, J = 4.1 Hz, 2H), 3.53-3.41 (dd, J = 11.7, 7.4 Hz, 1H), 3.13-2.99 (dd, J = 13.6, 3.0 Hz, 1H), 2.40-2.28 (m, 1H), 2.27-2.18 (m, 1H), 1.49-1.35 (d, J = 6.4 Hz, 3H) | ¹³C NMR (CDCl₃) δ 171.17, 168.92, 159.12, 155.35, 148.74, 140.65, 139.38, 130.15, 129.76, 129.11, 128.44, 126.22, 121.36, 115.45, 109.59, 81.84, 75.68, 72.16, 72.06, 67.09, 56.10, 51.46, 47.57, 35.28, 19.00 |
| 34 | — | (Thin film) 3374, 3062, | HRMS-ESI (m/z) [M + H]⁺ | ¹H NMR (CDCl₃) δ 8.48-8.34 (d, J = 8.2 Hz, | ¹³C NMR (CDCl₃) δ 171.78, 170.28, |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | 3026, 2938, 2873, 1750, 1676, 1577, 1505, 1454, 1436, 1382, 1310, 1275, 1243, 1200, 1140, 1083, 1045, 1003, 969, 908, 830, 807, 728, 700, 647 | calc'd for C₃₄H₄₁N₂O₉, 621.2807; found, 621.2809 | 1H), 8.34-8.20 (d, J = 5.4 Hz, 1H), 7.36-7.24 (d, J = 7.5 Hz, 4H), 7.23-7.12 (m, 6H), 6.98-6.87 (d, J = 5.4 Hz, 1H), 5.77-5.66 (s, 2H), 5.10-4.93 (m, 3H), 4.09-3.96 (dd, J = 11.6, 7.4 Hz, 1H), 3.97-3.83 (s, 3H), 3.76-3.66 (dd, J = 15.1, 6.5 Hz, 1H), 3.64-3.53 (m, 1H), 3.54-3.47 (m, 1H), 3.47-3.36 (m, 2H), 3.19-3.09 (m, 3H), 2.79-2.68 (dd, J = 8.9, 6.7 Hz, 3H), 2.37-2.27 (t, J = 12.7 Hz, 1H), 2.10-2.02 (s, 3H), 2.02-1.87 (q, J = 7.8, 7.2 Hz, 4H), 1.55-1.44 (d, J = 6.4 Hz, 3H) | 163.17, 160.19, 145.77, 143.92, 142.13, 141.65, 139.87, 129.17, 128.44, 128.39, 128.33, 126.12, 125.90, 109.69, 89.40, 85.05, 75.62, 72.36, 72.22, 71.88, 56.19, 51.81, 47.26, 35.23, 32.42, 31.88, 20.87, 18.84 |
| 35 | — | (Thin film) 2935, 1752, 1679, 1581, 1506, 1454, 1376, 1311, 1203, 1074, 1005, 971 | HRMS-ESI (m/z) [M + H]⁺ calc'd for C₃₁H₄₁N₂O₉, 585.2807; found, 585.2814 | ¹H NMR (CDCl₃) δ 8.44-8.32 (m, 1H), 8.31-8.20 (d, J = 5.3 Hz, 1H), 7.34-7.22 (m, 2H), 7.22-7.10 (d, J = 7.4 Hz, 3H), 6.99-6.87 (d, J = 5.4 Hz, 1H), 5.77-5.62 (s, 2H), 5.08-4.86 (dt, J = 15.2, 8.1 Hz, 3H), 4.09-3.99 (dd, J = 11.6, 7.0 Hz, 1H), 3.93-3.85 (s, 3H), 3.50-3.34 (m, 5H), 3.33-3.26 (dd, J = 11.3, 7.5 Hz, 2H), 3.25-3.16 (d, J = 13.2 Hz, 1H), 2.34-2.24 (t, J = 12.9 Hz, 1H), 2.12-1.97 (m, 3H), 1.94-1.84 (m, 0H), 1.84-1.72 (s, 2H), 1.63-1.54 (s, 5H), 1.53-1.44 (d, J = 6.4 Hz, 4H), 1.37-1.09 (m, 3H) | ¹³C NMR (CDCl₃) δ 171.86, 170.29, 163.14, 160.19, 145.76, 143.92, 142.17, 140.38, 129.16, 128.42, 126.02, 109.66, 89.42, 81.64, 79.65, 76.41, 73.10, 72.60, 56.18, 52.06, 47.73, 35.20, 33.31, 33.07, 25.62, 24.78, 24.70, 20.87, 18.80 |
| 36 | — | (Thin film) 3370, 3027, 2986, 2948, 1752, 1706, 1639, 1579, 1505, 1455, 1436, 1379, 1237, 1197, 1130, 1044, 969, 830, 728 | HRMS-ESI (m/z) [M + H]⁺ calc'd for C₂₉H₃₄N₂O₁₁Na, 609.2055; found, 609.2057 | ¹H NMR (CDCl₃) δ 8.43-8.35 (d, J = 8.2 Hz, 1H), 8.29-8.24 (d, J = 5.4 Hz, 1H), 7.53-7.45 (d, J = 12.2 Hz, 1H), 7.33-7.27 (m, 2H), 7.24-7.18 (m, 1H), 7.17-7.11 (m, 2H), 6.97-6.93 (d, J = 5.4 Hz, 1H), 5.75-5.70 (d, J = 1.0 Hz, 2H), 5.45-5.37 (d, J = 12.2 Hz, 1H), 5.12-5.02 (m, 2H), 4.09-4.00 (dd, J = 11.7, 7.5 Hz, 1H), 3.95-3.89 (s, 3H), 3.83-3.73 (m, 1H), 3.73-3.69 (s, 3H), 3.59-3.54 (m, 1H), 3.54-3.47 (m, 1H), 3.47-3.39 (dd, J = 11.7, 7.4 Hz, 1H), 2.98-2.90 (dd, J = 13.8, 3.4 Hz, 1H), 2.43-2.32 (dd, J = 13.7, 11.3 Hz, 1H), 2.16-2.08 (m, 1H), 2.08-2.04 (s, 3H), 1.48-1.39 (d, J = 6.4 Hz, 3H) | ¹³C NMR (CDCl₃) δ 171.65, 170.27, 167.95, 163.20, 162.93, 160.23, 145.78, 144.00, 141.97, 138.54, 129.11, 128.57, 126.47, 109.77, 98.51, 89.38, 88.98, 74.06, 72.13, 71.27, 56.21, 51.58, 51.25, 46.51, 35.25, 20.87, 18.77 |
| 37 | — | (Neat film) 3370, 2986, 2939, 1754, 1720, 1677, 1601, 1581, 1506, 1452, | HRMS-FAB (m/z) [M + Na]⁺ calc'd for C₃₂H₃₄N₂O₁₀Na, 629.2106; found, | ¹H NMR (CDCl₃) δ 8.50-8.40 (d, J = 8.1 Hz, 1H), 8.33-8.22 (d, J = 5.4 Hz, 1H), 8.10-8.01 (dd, J = 8.4, 1.3 Hz, 2H), 7.66-7.55 (m, 1H), | ¹³C NMR (CDCl₃) δ 171.70, 170.29, 165.88, 163.20, 160.23, 145.77, 144.02, 142.09, 138.94, 133.48, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | 1437, 1378, 1264, 1200, 1107, 1003, 970, 909, 830, 729, 713 | 629.2105 | 7.54-7.42 (t, J = 7.7 Hz, 2H), 7.25-7.21 (d, J = 7.5 Hz, 2H), 7.19-7.08 (m, 3H), 6.97-6.93 (d, J = 5.4 Hz, 1H), 5.77-5.67 (d, J = 0.9 Hz, 2H), 5.29-5.19 (m, 2H), 5.18-5.08 (q, J = 7.1 Hz, 1H), 4.12-4.02 (dd, J = 11.7, 7.3 Hz, 1H), 3.95-3.87 (s, 3H), 3.74-3.67 (m, 1H), 3.65-3.58 (m, 1H), 3.58-3.52 (dd, J = 11.7, 6.6 Hz, 1H), 2.89-2.77 (dd, J = 13.3, 3.0 Hz, 1H), 2.42-2.24 (m, 2H), 2.09-2.04 (s, 3H), 1.43-1.34 (d, J = 6.0 Hz, 3H) | 129.81, 129.43, 128.99, 128.58, 128.48, 126.29, 109.73, 89.43, 77.72, 74.26, 72.85, 56.20, 52.09, 45.93, 35.16, 20.87, 18.41 |
| 38 | — | (Neat film) 3371, 2987, 2937, 1752, 1728, 1579, 1506, 1455, 1437, 1383, 1310, 1243, 1198, 1166, 1100, 1003, 969, 908, 830, 727, 701 | HRMS-ESI (m/z) [M + Na]$^+$ calc'd for C$_{29}$H$_{34}$N$_2$O$_{10}$Na, 593.2106; found, 593.2104 | $^1$H NMR (CDCl$_3$) δ 8.53-8.34 (d, J = 8.1 Hz, 1H), 8.34-8.17 (d, J = 5.4 Hz, 1H), 7.33-7.27 (m, 2H), 7.24-7.18 (m, 1H), 7.18-7.12 (m, 2H), 6.97-6.92 (d, J = 5.4 Hz, 1H), 5.75-5.68 (d, J = 0.8 Hz, 2H), 5.14-5.03 (m, 2H), 5.01-4.92 (t, J = 9.3 Hz, 1H), 4.06-3.97 (dd, J = 11.7, 7.3 Hz, 1H), 3.94-3.87 (s, 3H), 3.68-3.59 (m, 1H), 3.57-3.47 (m, 2H), 2.83-2.72 (dd, J = 14.0, 3.7 Hz, 1H), 2.35-2.23 (dd, J = 13.9, 11.3 Hz, 1H), 2.21-2.08 (m, 1H), 2.08-2.03 (s, 3H), 1.70-1.62 (m, 1H), 1.43-1.31 (d, J = 6.3 Hz, 3H), 1.10-1.00 (m, 2H), 0.97-0.85 (m, 2H) | $^{13}$C NMR (CDCl$_3$) δ 174.28, 171.65, 170.28, 163.17, 160.22, 145.76, 144.00, 142.09, 139.10, 129.04, 128.52, 126.31, 109.72, 89.42, 74.23, 72.74, 56.20, 52.01, 45.83, 35.06, 20.86, 18.27, 12.86, 8.67 |
| 39 | — | (Thin film) 3375, 2940, 1753, 1678, 1579, 1506, 1384, 1310, 1243, 1202, 1141, 1097, 1048, 1005, 970 | HRMS-ESI (m/z) [M + Na]$^+$ calc'd for C$_{26}$H$_{32}$N$_2$O$_9$Na, 539.2000; found, 539.2006 | $^1$H NMR (CDCl$_3$) δ 8.49-8.32 (d, J = 8.2 Hz, 1H), 8.32-8.17 (d, J = 5.4 Hz, 1H), 7.34-7.27 (m, 2H), 7.24-7.16 (dd, J = 7.3, 3.4 Hz, 3H), 6.97-6.92 (d, J = 5.4 Hz, 1H), 5.78-5.66 (s, 2H), 5.08-5.00 (q, J = 7.4 Hz, 1H), 5.00-4.93 (dd, J = 9.2, 6.4 Hz, 1H), 4.08-3.96 (dd, J = 11.7, 7.4 Hz, 1H), 1.54-1.48 (m, 3H), 3.94-3.86 (s, 3H), 3.57-3.49 (s, 4H), 3.48-3.37 (m, 2H), 3.18-3.11 (dd, J = 13.7, 3.4 Hz, 1H), 3.11-3.04 (t, J = 9.1 Hz, 1H), 2.42-2.30 (m, 1H), 2.08-2.03 (s, 3H), 2.03-1.90 (s, 1H), 1.54-1.48 (d, J = 6.4 Hz, 3H) | $^{13}$C NMR (CDCl$_3$) δ 171.77, 170.27, 163.17, 160.19, 145.78, 143.93, 142.13, 139.76, 129.19, 128.43, 126.13, 109.69, 89.40, 86.57, 75.45, 72.32, 72.07, 60.04, 56.19, 51.77, 47.05, 35.24, 20.87, 18.81 |
| 40 | — | (Thin film) 2939, 1752, 1676, 1585, 1492, 1455, 1436, 1380, 1210, 1235, 1200, 1138, 1044, 1004, 970, 910, 830, 752, | HRMS-ESI (m/z) [M + Na]$^+$ calc'd for C$_{32}$H$_{34}$N$_2$O$_9$Na, 601.2157; found, 601.2158 | $^1$H NMR (CDCl$_3$) δ 8.44-8.38 (d, J = 8.2 Hz, 1H), 8.32-8.23 (d, J = 5.4 Hz, 1H), 7.35-7.27 (m, 4H), 7.25-7.09 (m, 5H), 7.04-6.92 (m, 5H), 5.78-5.66 (s, 2H), 5.22-5.12 (dd, J = 9.1, 6.5 Hz, 1H), 5.12-5.02 (q, J = 7.5 Hz, 1H), | $^{13}$C NMR (CDCl$_3$) δ 171.81, 170.29, 163.19, 160.21, 159.17, 145.78, 143.97, 142.08, 139.46, 129.74, 129.13, 128.41, 126.17, 121.30, 115.46, 109.73, 89.40, 81.86, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | 731, 701 | | 4.39-4.26 (t, J = 8.9 Hz, 1H), 4.14-4.02 (dd, J = 11.7, 7.4 Hz, 1H), 3.95-3.84 (s, 3H), 3.62-3.53 (d, J = 4.0 Hz, 2H), 3.48-3.37 (dd, J = 11.6, 7.4 Hz, 1H), 3.10-2.94 (dd, J = 13.5, 2.8 Hz, 2H), 2.37-2.25 (m, 1H), 2.25-2.12 (m, 1H), 2.11-2.01 (s, 3H), 1.44-1.35 (d, J = 6.4 Hz, 3H) | 75.51, 72.34, 71.85, 56.20, 51.79, 47.61, 35.32, 20.88, 19.03 |
| 41 | — | (Thin film) 2955, 2927, 2871, 1747, 1649, 1577, 1529, 1481, 1452, 1328, 1281, 1263, 1242, 1203, 1139, 1083, 1054 | HRMS-ESI (m/z) [M + H]$^+$ calc'd for C$_{27}$H$_{37}$N$_2$O$_7$, 501.2595; found, 501.2601 | $^1$H NMR (CDCl$_3$) δ 12.04-11.87 (s, 1H), 8.65-8.43 (d, J = 8.2 Hz, 1H), 8.05-7.90 (d, J = 5.2 Hz, 1H), 7.35-7.27 (m, 2H), 7.24-7.15 (m, 3H), 6.89-6.82 (d, J = 5.2 Hz, 1H), 5.12-4.92 (m, 2H), 4.12-3.97 (dd, J = 11.7, 7.3 Hz, 1H), 3.97-3.87 (s, 3H), 3.79-3.64 (m, 1H), 3.64-3.54 (m, 1H), 3.54-3.48 (m, 1H), 3.48-3.38 (m, 2H), 3.21-3.07 (m, 2H), 2.41-2.26 (t, J = 12.7 Hz, 1H), 2.01-1.89 (s, 1H), 1.82-1.65 (m, 1H), 1.58-1.55 (s, 3H), 1.54-1.48 (m, 5H), 1.01-0.84 (m, 6H) | $^{13}$C NMR (CDCl$_3$) δ 171.14, 168.91, 155.35, 148.74, 140.62, 139.91, 130.24, 129.18, 128.47, 126.15, 109.56, 85.11, 75.91, 72.55, 72.24, 71.23, 56.08, 51.55, 47.35, 39.19, 35.21, 24.93, 22.71, 22.68, 18.79 |
| 42 | — | (Thin film) 3366, 2954, 2871, 1754, 1679, 1506, 1465, 1384, 1311, 1246, 1202, 1084, 1046, 1005, 971 | HRMS-ESI (m/z) [M + H]$^+$ calc'd for C$_{30}$H$_{41}$N$_2$O$_9$, 573.2807; found, 573.2812 | $^1$H NMR (CDCl$_3$) δ 8.51-8.31 (d, J = 8.1 Hz, 1H), 8.31-8.17 (d, J = 5.4 Hz, 1H), 7.38-7.24 (m, 2H), 7.24-7.14 (m, 3H), 7.00-6.88 (d, J = 5.4 Hz, 1H), 5.82-5.63 (s, 2H), 5.10-4.91 (m, 2H), 4.11-3.95 (dd, J = 11.7, 7.4 Hz, 1H), 3.95-3.82 (s, 3H), 3.75-3.64 (m, 1H), 3.64-3.54 (m, 1H), 3.54-3.47 (m, 1H), 3.47-3.34 (m, 2H), 3.20-3.09 (m, 2H), 2.40-2.27 (m, 1H), 2.08-2.02 (s, 3H), 2.02-1.89 (m, 1H), 1.81-1.67 (tt, J = 13.3, 6.6 Hz, 2H), 1.55-1.46 (m, 5H), 0.99-0.86 (d, J = 6.6 Hz, 6H) | $^{13}$C NMR (CDCl$_3$) δ 171.78, 170.25, 163.18, 160.19, 145.78, 143.91, 142.16, 139.97, 129.18, 128.43, 126.10, 109.71, 89.39, 85.07, 75.71, 72.39, 72.29, 71.14, 56.19, 51.85, 47.36, 39.18, 35.21, 24.91, 22.71, 22.68, 20.86, 18.80 |
| 43 | — | (Neat film) 3361, 2939, 1748, 1649, 1576, 1530, 1453, 1577, 1439, 1328, 1439, 1263, 1281, 1204, 1101, 733 | HRMS-ESI (m/z) [M + H]$^+$ calc'd for C$_{24}$H$_{29}$F$_2$N$_2$O$_7$, 495.1937; found, 495.1942 | $^1$H NMR (CDCl$_3$) δ 11.92 (s, 1H), 8.52 (d, J = 8.4 Hz, 1H), 7.98 (d, J = 5.2 Hz, 1H), 7.35-7.27 (m, 2H), 7.24-7.14 (m, 3H), 6.86 (d, J = 5.2 Hz, 1H), 5.85 (tt, J = 55.1, 4.0 Hz, 1H), 5.09-4.92 (m, 2H), 4.05 (dd, J = 11.7, 7.3 Hz, 1H), 1.58-1.46 (m, 3H), 3.93 (s, 4H), 3.77 (tdd, J = 13.8, 10.8, 4.0 Hz, 1H), 3.54-3.46 (m, 2H), 3.46-3.37 (m, 1H), 3.30 (t, J = 8.9 Hz, 1H), 3.11 (dd, J = 13.6, 3.7 Hz, 1H), 2.42 (dd, J = 13.5, 11.6 Hz, 1H), 2.02 (ddt, J = 11.7, 8.2, 4.5 Hz, 1H), 1.53 (d, J = 6.4 Hz, 3H) | $^{13}$C NMR (CDCl$_3$) δ 171.12, 168.93, 155.35, 148.73, 140.66, 139.29, 130.12, 129.14, 128.53, 126.33, 116.22, 113.82, 111.42, 109.61, 86.02, 75.11, 72.03, 71.94, 71.75, 71.48, 71.20, 56.09, 51.37, 47.03, 35.15, 18.76 |

TABLE 3-continued

Analytical Data

| Cmpd No.* | MP (° C.) | IR (cm⁻¹) | MASS | ¹H NMR* | ¹³C NMR* |
|---|---|---|---|---|---|
| 44 | — | (Neat film) 3938, 1752, 1677, 1579, 1506, 1378, 1311, 1276, 1243, 1202, 1142, 1100, 1052, 1004, 970, 909, 831, 733 | HRMS-ESI (m/z) [M + H]⁺ calc'd for $C_{27}H_{33}F_2N_2O_9$, 568.2181; found, 568.2184 | ¹H NMR (CDCl₃) δ 8.38 (d, J = 8.2 Hz, 1H), 8.26 (d, J = 5.4 Hz, 1H), 7.34-7.25 (m, 2H), 7.25-7.13 (m, 3H), 6.95 (d, J = 5.4 Hz, 1H), 6.03-5.64 (m, 3H), 5.16-4.91 (m, 2H), 4.04 (dd, J = 11.7, 7.4 Hz, 1H), 3.98-3.84 (m, 4H), 1.58-1.46 (m, 3H), 3.77 (tdd, J = 13.7, 10.8, 4.0 Hz, 1H), 3.56-3.43 (m, 2H), 3.39 (dd, J = 11.7, 7.5 Hz, 1H), 3.29 (t, J = 9.0 Hz, 1H), 3.10 (dd, J = 13.6, 3.6 Hz, 1H), 2.42 (dd, J = 13.5, 11.5 Hz, 1H), 2.06 (s, 3H), 2.00 (dq, J = 8.6, 4.2 Hz, 1H), 1.52 (d, J = 6.4 Hz, 3H) | ¹³C NMR (CDCl₃) δ 171.75, 170.27, 163.18, 160.22, 145.79, 143.96, 142.05, 139.36, 129.15, 128.51, 126.29, 116.23, 113.84, 111.44, 109.76, 89.38, 86.00, 74.91, 72.20, 71.73, 71.39, 56.21, 51.68, 47.02, 35.19, 20.87, 18.78 |
| 45 | — | IR (neat film) 3366, 2937, 1747, 1649, 1577, 1529, 1481, 1452, 1328, 1263, 1281, 1203, 1140, 1080 | HRMS-ESI (m/z) [M + Na]⁺ calc'd for $C_{27}H_{36}N_2O_8Na$, 539.2364; found, 539.2362 | (1:1 mixture of diastereomers); ¹H NMR (CDCl₃) δ 11.95 (s, 1H), 8.55 (d, J = 8.3 Hz, 1H), 7.97 (d, J = 5.2 Hz, 1H), 7.33-7.24 (m, 2H), 7.24-7.12 (m, 3H), 6.85 (d, J = 5.2 Hz, 1H), 5.09-4.90 (m, 2H), 4.09-3.94 (m, 1H), 3.92 (s, 3H), 3.89-3.77 (m, 1H), 3.77-3.65 (m, 1H), 3.65-3.39 (m, 5H), 2.91-2.72 (m, 3H), 3.32 (s, 2H), 3.27 (s, 1H), 3.21-3.08 (m, 2H), 2.42-2.28 (m, 1H), 2.07-1.92 (m, 1H), 1.82-1.62 (m, 2H), 1.52 (dd, J = 6.4, 3.3 Hz, 3H), 1.16 (d, J = 6.1 Hz, 3H) | ¹³C NMR (CDCl₃) δ 171.12, 171.09, 168.90, 155.31, 148.70, 140.62, 139.86, 139.81, 130.17, 129.15, 128.45, 126.14, 109.57, 84.98, 75.85, 75.79, 73.41, 73.39, 72.67, 72.57, 72.27, 72.21, 69.14, 68.90, 56.07, 55.95, 55.90, 51.57, 51.54, 47.31, 47.18, 38.60, 37.42, 37.36, 35.15, 35.05, 19.10, 18.74 |
| 46 | — | (Neat film) 3371, 2974, 2939, 2878, 1754, 1679, 1506, 1202, 1081 | HRMS-ESI (m/z) [M + Na]⁺ calc'd for $C_{30}N_{40}N_2O_{10}Na$, 611.2575; found, 611.2580 | (1:1 mixture of diastereomers); ¹H NMR (CDCl₃) δ 8.40 (d, J = 8.1 Hz, 1H), 8.26 (d, J = 5.3 Hz, 1H), 7.34-7.24 (m, 2H), 7.24-7.13 (m, 3H), 6.94 (d, J = 5.4 Hz, 1H), 5.71 (s, 2H), 5.12-4.90 (m, 2H), 4.01 (dd, J = 11.7, 7.3 Hz, 1H), 3.90 (s, 3H), 3.82 (q, J = 7.4, 6.9 Hz, 0.5H), 3.71 (q, J = 6.0 Hz, 1H), 3.63-3.36 (m, 4.5H), 3.31 (s, 1.5H), 3.26 (s, 1.5H), 3.22-3.07 (m, 2H), 2.32 (t, J = 12.7 Hz, 1H), 2.11-2.02 (m, 3H), 1.97 (d, J = 8.7 Hz, 1H), 1.84-1.66 (m, 2H), 1.51 (dd, J = 6.3, 3.0 Hz, 3H), 1.16 (d, J = 6.1 Hz, 3H) | ¹³C NMR (CDCl₃) δ 171.76, 171.73, 170.26, 163.17, 160.19, 145.78, 143.91, 142.14, 139.94, 139.89, 129.16, 128.43, 126.11, 109.71, 89.39, 84.97, 75.66, 75.60, 73.44, 73.41, 72.45, 72.33, 69.05, 68.80, 56.20, 55.95, 55.91, 51.88, 51.85, 47.31, 47.17, 37.42, 37.37, 35.19, 35.08, 20.86, 19.11, 18.76 |
| 47 | — | — | HRMS (m/z) [M + H]⁺calc'd for $C_{29}H_{49}NO_6SiNa$ 558.3221; found, 558.3224 | ¹H NMR (CDCl₃) δ 7.34-7.07 (m, 5H), 5.30-5.14 (m, 1H), 5.11 (d, J = 8.1 Hz, 1H), 4.53 (q, J = 8.3 Hz, 1H), 4.08 (dd, J = 11.6, 6.9 Hz, 1H), 3.88 (dd, J = 6.3, 5.0 Hz, 1H), 3.60 (dd, J = 11.7, 5.9 Hz, 1H), 3.44 (d, J = 11.6 Hz, 1H), 3.07 (t, J = 10.3 Hz, 1H), 2.92 (dd, J = 13.3, 4.0 Hz, 1H), 2.76 (t, | ¹³C NMR (CDCl₃) δ 171.75, 154.92, 140.37, 129.13, 128.35, 126.01, 79.99, 78.88, 73.17, 70.69, 52.89, 49.64, 34.63, 28.28, 19.51, 18.24, 18.19, 13.14 |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | | | J = 12.4 Hz, 1H), 1.99 (td, J = 10.6, 5.0 Hz, 1H), 1.50-1.38 (m, 12H), 1.14-0.99 (m, 21H) | |
| 48 | 62-67 | — | HRMS-ESI (m/z) [M + H]⁺ calc'd for C₂₀H₂₉NNaO₆, 402.1887, found, 402.1892. | ¹H NMR (CDCl₃) δ 7.29 (t, J = 7.2 Hz, 2H), 7.24-7.16 (m, 3H), 5.14 (d, J = 8.3 Hz, 1H), 4.88 (dq, J = 8.8, 6.3 Hz, 1H), 4.66 (dd, J = 15.4, 7.6 Hz, 1H), 3.91 (dd, J = 11.6, 7.6 Hz, 1H), 3.57 (d, J = 10.4 Hz, 1H), 3.45 (dt, J = 11.4, 7.8 Hz, 2H), 3.33 (dd, J = 11.5, 7.3 Hz, 1H), 3.10 (dd, J = 13.8, 4.3 Hz, 1H), 2.57-2.44 (m, 1H), 1.90 (d, J = 6.9 Hz, 1H), 1.48 (d, J = 6.4 Hz, 3H), 1.42 (s, 8H) | ¹³C NMR (CDCl₃) δ 172.37, 154.99, 139.47, 129.15, 128.55, 126.32, 80.21, 77.22, 77.16, 76.01, 72.47, 52.71, 48.03, 36.20, 28.27, 18.80 |
| 49 | 128-129 | IR (neat film) 3342, 2980, 2949, 1753, 1703, 1639, 1497, 1329, 1132, 910, 731 | HRMS-ESI (m/z) [M + Na]⁺ calc'd for C₂₄H₃₃NO₈Na 486.2098; found, 486.2104. | ¹H NMR (CDCl₃) δ 7.48 (d, J = 12.2 Hz, 1H), 7.32-7.27 (m, 2H), 7.23-7.18 (m, 1H), 7.15-7.11 (m, 2H), 5.40 (d, J = 12.2 Hz, 1H), 5.10 (d, J = 8.3 Hz, 1H), 5.02 (dd, J = 9.3, 6.4 Hz, 1H), 4.64 (dd, J = 15.3, 7.5 Hz, 1H), 3.92 (dd, J = 11.6, 7.6 Hz, 1H), 3.74 (d, J = 9.1 Hz, 1H), 3.71 (s, 3H), 3.51 (d, J = 11.1 Hz, 1H), 3.43 (dd, J = 10.5, 6.4 Hz, 1H), 3.29 (dd, J = 11.3, 7.5 Hz, 1H), 2.92 (dd, J = 13.8, 3.5 Hz, 1H), 2.34 (t, J = 12.5 Hz, 1H), 2.06 (s, 1H), 1.42 (s, 9H), 1.41 (d, J = 6.5 Hz, 3H) | ¹³C NMR (100 MHz, CDCl₃) δ 172.16, 167.97, 162.94, 154.91, 138.54, 129.09, 128.57, 126.48, 98.50, 89.01, 80.31, 73.94, 72.57, 71.33, 52.70, 51.26, 46.47, 35.18, 28.25, 18.73 |
| 50 | — | (Neat film) 3357, 3026, 2978, 2880, 1741, 1711, 1497, 1367, 1294, 1198, 1163, 1070, 1023, 911, 731 | HRMS-ESI (m/z) [M + Na]⁺ calc'd for C₂₄H₃₅NO₈Na; 488.2255, found, 488.2260 | ¹H NMR (CDCl₃) δ 7.34-7.27 (m, 2H), 7.24-7.10 (m, 3H), 5.18-5.03 (d, J = 8.3 Hz, 1H), 5.01-4.81 (dq, J = 9.2, 6.4 Hz, 1H), 4.69-4.47 (q, J = 7.3 Hz, 1H), 4.07-3.76 (m, 3H), 3.75-3.61 (s, 3H), 3.53-3.31 (m, 2H), 3.31-3.03 (m, 3H), 2.71-2.52 (t, J = 6.2 Hz, 2H), 2.41-2.22 (t, J = 12.6 Hz, 1H), 1.98-1.75 (s, 1H), 1.53-1.46 (d, J = 6.4 Hz, 3H), 1.46-1.36 (s, 9H) | ¹³C NMR (100 MHz, CDCl₃) δ 172.23, 171.73, 139.78, 129.15, 128.44, 126.14, 85.23, 80.11, 75.32, 72.86, 72.28, 67.67, 52.91, 51.82, 47.16, 35.24, 35.05, 28.26, 18.68 |
| 51 | 182-185 | (ATR) 3344, 2982, 2941, 1752, 1717, 1690, 1638, 1527, 1454, 1381, 1205, 1079, 833, 751, 697 | HRMS-ESI (m/z) [M + Na]⁺ calc'd for C₃₀H₃₇NO₈Na, 562.2411; found, 562.2427 | ¹H NMR (CDCl₃) δ 7.50 (d, J = 12.2 Hz, 1H), 7.40-7.09 (m, 10H), 5.44 (d, J = 12.2 Hz, 1H), 5.16 (s, 2H), 5.09 (d, J = 8.2 Hz, 1H), 5.01 (dd, J = 9.3, 6.4 Hz, 1H), 4.64 (dd, J = 15.3, 7.5 Hz, 1H), 3.91 (dd, J = 11.6, 7.5 Hz, 1H), 3.73 (t, J = 9.2 Hz, 1H), 3.45 (dt, J = 10.6, 8.5 Hz, 2H), 3.28 (dd, J = 11.3, 7.5 Hz, 1H), 2.92 (dd, J = 13.8, 3.5 Hz, 1H), 2.34 (t, J = 12.4 Hz, 1H), 2.05 (s, 1H), 1.51-1.35 (m, 12H) | ¹³C NMR (100 MHz, CDCl₃) δ 172.15, 167.40, 163.21, 138.54, 136.22, 129.10, 128.57, 128.25, 128.19, 126.48, 98.54, 89.01, 80.31, 73.94, 72.60, 71.36, 65.87, 52.72, 46.48, 35.21, 28.26, 18.74 |

TABLE 3-continued

Analytical Data

| Cmpd No.* | MP (° C.) | IR (cm⁻¹) | MASS | ¹H NMR* | ¹³C NMR* |
|---|---|---|---|---|---|
| 52 | — | (ATR) 3319, 2977, 2930, 2879, 1710, 1497, 1391, 1368, 1246, 1201, 1161, 1065, 851, 750 | HRMS-ESI [M + Na]⁺ calc'd for $C_{23}H_{33}NO_8Na$, 474.2098; found, 474.2118 | ¹H NMR (CDCl₃) δ 7.31-7.22 (m, 2H), 7.22-7.12 (m, 3H), 5.14 (d, J = 8.2 Hz, 1H), 4.93 (dq, J = 9.0, 6.4 Hz, 1H), 4.59 (dd, J = 15.2, 7.4 Hz, 1H), 3.99-3.84 (m, 2H), 3.79 (dt, J = 8.9, 6.1 Hz, 1H), 3.48-3.31 (m, 2H), 3.24 (dd, J = 11.2, 7.5 Hz, 1H), 3.16 (t, J = 9.0 Hz, 1H), 3.12-3.06 (m, 1H), 2.60 (t, J = 6.1 Hz, 2H), 2.32 (t, J = 12.6 Hz, 1H), 1.90 (s, 1H), 1.48 (d, J = 6.4 Hz, 3H), 1.42 (s, 9H) | ¹³C NMR (100 MHz, CDCl₃) δ 176.37, 172.28, 154.99, 139.74, 129.16, 128.42, 126.13, 85.30, 80.17, 75.27, 72.78, 72.16, 67.35, 52.88, 47.20, 35.09, 28.27, 18.71 |
| 53 | 142-143 | — | HRMS-ESI [M + H]⁺ calc'd for $C_{25}H_{39}N_2O_7$, 480.2784; found, 480.2785 | ¹H NMR (CDCl₃) δ 7.32-7.27 (m, 2H), 7.23-7.14 (m, 3H), 5.12 (d, J = 7.6 Hz, 1H), 4.94 (dq, J = 9.2, 6.3 Hz, 1H), 4.60 (d, J = 7.4 Hz, 1H), 4.02 (dd, J = 15.5, 6.8 Hz, 1H), 3.93-3.81 (m, 2H), 3.49 (d, J = 10.8 Hz, 1H), 3.42-3.33 (m, 1H), 3.34-3.25 (m, 1H), 3.21-3.08 (m, 2H), 3.02 (s, 3H), 2.94 (s, 3H), 2.71-2.51 (m, 2H), 2.31 (t, J = 12.7 Hz, 1H), 1.92 (s, 1H), 1.50 (d, J = 6.4 Hz, 3H), 1.42 (s, 9H) | ¹³C NMR (100 MHz, CDCl₃) δ 172.15, 170.50, 154.97, 139.88, 129.11, 128.42, 126.09, 85.45, 80.09, 77.22, 75.43, 73.11, 72.81, 68.77, 53.07, 47.17, 37.35, 35.37, 35.12, 33.77, 28.26, 18.77 |
| 54 | — | (ATR) 3347, 2978, 2928, 2875, 1750, 1710, 1496, 1354, 1367, 1385, 1327, 1163, 1088, 910, 855, 731 | HRMS-ESI (m/z) [M + Na]⁺ calc'd for $C_{24}H_{37}NO_7Na$, 474.2462; found, 474.2467 | ¹H NMR (CDCl₃) δ 7.28 (dd, J = 8.6, 6.9 Hz, 2H), 7.24-7.14 (m, 3H), 5.13 (d, J = 8.1 Hz, 1H), 4.94 (dq, J = 9.3, 6.4 Hz, 1H), 4.60 (dd, J = 14.9, 7.3 Hz, 1H), 3.88 (dd, J = 11.5, 7.3 Hz, 1H), 3.76 (dt, J = 12.7, 6.3 Hz, 1H), 3.63 (dt, J = 8.7, 6.3 Hz, 1H), 3.53-3.42 (m, 3H), 3.41-3.33 (m, 1H), 3.30 (s, 4H), 3.28-3.22 (m, 1H), 3.18-3.05 (m, 2H), 2.29 (t, J = 12.7 Hz, 1H), 1.98-1.89 (m, 1H), 1.86 (p, J = 6.2 Hz, 2H), 1.48 (d, J = 6.4 Hz, 3H), 1.42 (s, 10H) | ¹³C NMR (100 MHz, CDCl₃) δ 172.24, 154.98, 139.94, 129.15, 128.43, 126.11, 84.99, 80.09, 75.51, 72.94, 72.51, 69.18, 58.64, 52.99, 47.23, 35.05, 30.47, 28.27, 18.70 |
| 55 | — | — | HRMS-ESI (m/z) [M + Na]⁺ calc'd for $C_{34}H_{57}NNaO_8Si$, 658.3746; found; 658.3722 | ¹H NMR (CDCl₃) δ 7.28 (d, J = 7.0 Hz, 2H), 7.25-7.17 (m, 2H), 5.14 (dd, J = 7.0, 3.3 Hz, 1H), 5.00 (dd, J = 9.2, 6.9 Hz, 1H), 4.07 (qd, J = 11.6, 8.1 Hz, 2H), 3.92 (dd, J = 6.0, 3.3 Hz, 1H), 3.73-3.64 (m, 1H), 3.64-3.54 (m, 1H), 2.90 (d, J = 10.9 Hz, 1H), 2.87-2.76 (m, 1H), 2.04 (dd, J = 11.0, 5.3 Hz, 1H), 1.54-1.46 (m, 21H), 1.43 (d, J = 7.0 Hz, 4H), 1.06 (d, J = 2.2 Hz, 18H) | ¹³C NMR (CDCl₃) δ 169.50, 152.72, 140.67, 129.13, 128.31, 125.93, 82.88, 78.83, 72.71, 57.79, 49.97, 34.16, 28.28, 27.91, 19.67, 18.24, 18.18, 18.13, 13.14, 12.78 |
| 56 | — | (ATR) 3061, 3026, 2980, 2933, 1741, 1705, 1654, 1601, 1495, 1451, | HRMS-ESI (m/z) [M + NH4]⁺ calc'd for $C_{35}H_{51}N_2O_8$, 627.3640; | ¹H NMR (CDCl₃) δ 7.46-7.27 (m, 7H), 7.25-7.15 (m, 3H), 6.63 (d, J = 15.9 Hz, 1H), 6.28 (dt, J = 15.9, 5.9 Hz, 1H), 5.13 (dd, J = 8.5, 6.5 Hz, 1H), | ¹³C NMR (CDCl₃) δ 169.98, 152.61, 143.34, 139.92, 136.48, 132.49, 130.51, 129.57, 129.25, 128.97, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | 1392, 1367, 1310, 1254, 1144, 1119, 1060, 967 909, 852, 730, 698 | found, 627.3642 | 4.94 (dq, J = 12.8, 6.3 Hz, 1H), 4.35 (ddd, J = 12.2, 5.9, 1.3 Hz, 1H), 4.24 (ddd, J = 12.2, 6.0, 1.3 Hz, 1H), 4.09 (dd, J = 11.8, 6.5 Hz, 1H), 3.86 (dd, J = 11.8, 8.6 Hz, 1H), 3.54 (d, J = 10.7 Hz, 1H), 3.41 (dd, J = 10.9, 6.1 Hz, 1H), 3.29 (t, J = 8.9 Hz, 1H), 3.17 (dd, J = 13.7, 3.5 Hz, 1H), 2.42 (t, J = 12.5 Hz, 1H), 2.05 (s, 1H), 1.53 (d, J = 6.4 Hz, 3H), 1.48 (s, 18H) | 128.85, 128.56, 128.39, 128.36, 128.29, 127.80, 126.69, 126.52, 126.05, 125.41, 125.31, 84.87, 83.04, 75.32, 72.84, 70.97, 57.43, 46.94, 35.27, 27.92, 19.03 |
| 57 | 139-141 | — | HRMS-ESI (m/z) [M + Na]$^+$ calc'd for C$_{25}$H$_{37}$NNaO$_8$, 502.2411; found, 502.2418 | $^1$H NMR (CDCl$_3$) δ 7.31-7.27 (m, 2H), 7.23-7.16 (m, 3H), 5.21 (dd, J = 8.8, 4.8 Hz, 1H), 5.06-4.91 (m, 1H), 4.16 (dd, J = 12.1, 4.8 Hz, 1H), 3.89 (dd, J = 12.1, 8.8 Hz, 1H), 3.77 (d, J = 9.9 Hz, 1H), 3.55-3.42 (m, 2H), 3.00 (dd, J = 13.8, 5.0 Hz, 1H), 2.57 (dd, J = 13.8, 9.4 Hz, 1H), 2.26 (d, J = 7.8 Hz, 1H), 2.10 (s, 1H), 1.50 (s, 18H), 1.47 (d, J = 6.5 Hz, 3H) | $^{13}$C NMR (CDCl$_3$) δ 169.75, 152.71, 139.53, 129.10, 128.49, 126.28, 83.15, 77.20, 76.51, 71.67, 57.69, 47.63, 36.34, 27.95, 18.58 |
| 58 | — | (ATR) 3027, 2979, 2934, 1741, 1706, 1454, 1393, 1357, 1313, 1206, 1145, 1121, 1067, 913, 731 | HRMS-ESI (m/z) [M + Na]$^+$ calc'd for C$_{31}$H$_{45}$NO$_8$Na, 582.3037; found, 582.3018 | (1:1 mixture of diastereomers); $^1$H NMR (CDCl$_3$) δ 7.30-7.23 (m, 2H), 7.22-7.15 (m, 3H), 5.95-5.86 (m, 1H), 5.86-5.76 (m, 1H), 5.04 (q, J = 7.6 Hz, 1H), 4.93-4.81 (m, 1H), 4.10-3.94 (m, 2H), 3.88 (ddd, J = 11.8, 7.9, 4.0 Hz, 1H), 3.51-3.34 (m, 3H), 3.22 (dd, J = 13.8, 3.5 Hz, 1H), 2.36 (dt, J = 26.2, 13.0 Hz, 1H), 2.17-2.01 (m, 1H), 2.02-1.84 (m, 2H), 1.84-1.70 (m, 3H), 1.53-1.49 (m, 4H), 1.47 (s, 8H), 1.47 (s, 8H) | $^{13}$C NMR (CDCl$_3$) δ 170.22, 152.59, 140.51, 140.36, 131.71, 131.46, 129.25, 129.18, 128.36, 128.33, 127.43, 126.95, 125.96, 82.83, 82.48, 82.25, 76.34, 75.98, 74.12, 73.86, 57.57, 57.35, 47.45, 47.36, 35.14, 34.98, 29.24, 28.92, 27.90, 25.28, 25.23, 19.02, 18.92 |
| 59 | — | (ATR) 3062, 3026, 2979, 2932, 1742, 1705, 1603, 1496, 1477, 1454, 1392, 1367, 1311, 1253, 1143, 1120, 909, 852, 730, 698 | HRMS-ESI (m/z) [M + Na]$^+$ calc'd for C$_{34}$H$_{47}$NO$_8$Na, 620.3194; found, 620.3186 | $^1$H NMR (CDCl$_3$) δ 7.27 (dd, J = 9.7, 5.2 Hz, 3H), 7.22-7.13 (m, 5H), 5.12 (dd, J = 8.5, 6.5 Hz, 1H), 4.89 (dq, J = 12.8, 6.3 Hz, 1H), 4.07 (dd, J = 11.8, 6.4 Hz, 1H), 3.84 (dd, J = 11.8, 8.6 Hz, 1H), 3.73-3.63 (m, 1H), 3.37 (dd, J = 10.8, 6.1 Hz, 1H), 3.15 (t, J = 9.0 Hz, 1H), 3.10 (dd, J = 13.6, 3.4 Hz, 1H), 2.35 (t, J = 12.6 Hz, 1H), 2.03-1.96 (m, 1H), 1.96-1.88 (m, 2H), 1.52-1.44 (m, 21H) | $^{13}$C NMR (CDCl$_3$) δ 169.98, 152.63, 141.70, 140.00, 129.24, 128.50, 128.39, 128.35, 128.31, 126.11, 126.03, 125.89, 84.96, 83.02, 75.29, 71.42, 71.00, 57.46, 46.86, 44.51, 35.11, 32.42, 31.87, 29.72, 27.92, 18.97 |
| 60 | — | — | HRMS-ESI (m/z) [M + Na]$^+$ calc'd for C$_{31}$H$_{47}$NO$_8$Na, 584.3194; found, 584.3171 | $^1$H NMR (CDCl$_3$) δ 7.32-7.23 (m, 2H), 7.22-7.13 (m, 3H), 5.04 (t, J = 7.6 Hz, 1H), 4.86 (dq, J = 13.0, 6.5 Hz, 1H), 3.99 (dd, J = 11.7, 7.5 Hz, 1H), 3.87 (dd, J = 11.7, 7.9 Hz, 1H), 3.44 (d, J = 3.8 Hz, 2H), | $^{13}$C NMR (CDCl$_3$) δ 170.20, 152.60, 140.50, 129.20, 128.33, 125.94, 99.99, 82.98, 81.56, 79.33, 76.24, 72.98, 71.08, 57.53, 47.39, 35.02, |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | | | 3.41-3.28 (m, 2H), 3.18 (dd, J = 13.5, 3.4 Hz, 1H), 2.34 (t, J = 12.8 Hz, 1H), 2.03-1.95 (m, 2H), 1.89 (ddd, J = 11.7, 7.7, 3.6 Hz, 1H), 1.81-1.72 (m, 2H), 1.52-1.43 (m, 21H), 1.35-1.08 (m, 6H) | 33.25, 33.01, 27.90, 25.63, 24.71, 24.65, 18.94. |
| 61 | 54-63 | (ATR) 3358, 3063, 3028, 2980, 2934, 1755, 1714, 1602, 1584, 1496, 1452, 1367, 1316, 1263, 1201, 1161, 1094, 1068, 1043, 1026, 909, 731, 710 | HRMS-ESI (m/z) [M + Na]⁺ calc'd for $C_{27}H_{33}NO_7Na$; 506.2149, found, 506.2158 | ¹H NMR (CDCl₃) δ 8.05 (dd, J = 8.4, 1.3 Hz, 2H), 7.63-7.55 (m, 1H), 7.51-7.43 (m, 2H), 7.24-7.19 (m, 2H), 7.19-7.06 (m, 3H), 5.27-5.13 (m, 3H), 4.71 (q, J = 7.1 Hz, 1H), 3.93 (dd, J = 11.7, 7.2 Hz, 1H), 3.66 (d, J = 10.9 Hz, 1H), 3.54 (dd, J = 10.5, 6.9 Hz, 1H), 3.42 (dd, J = 11.3, 6.4 Hz, 1H), 2.81 (dd, J = 13.6, 3.4 Hz, 1H), 2.38-2.28 (m, 1H), 2.25 (s, 0H), 1.43 (s, 9H), 1.38 (d, J = 6.0 Hz, 3H) | ¹³C NMR (CDCl₃) δ 172.16, 165.87, 138.91, 133.49, 129.79, 129.38, 128.95, 128.58, 128.48, 126.29, 80.21, 77.73, 74.11, 73.37, 73.04, 53.26, 45.88, 35.08, 28.27, 18.38 |
| 62 | 72-85 | (ATR) 3358, 2980, 2935, 1712, 1497, 1454, 1387, 1367, 1329, 1257, 1197, 1117, 1097, 1062, 1027, 910, 730, 700 | HRMS-ESI (m/z) [M + Na]⁺ calc'd for $C_{24}H_{33}NO_7Na$; 470.2149, found, 470.2152 | ¹H NMR (CDCl₃) δ 7.34-7.27 (m, 2H), 7.24-7.17 (t, J = 7.3 Hz, 1H), 7.17-7.10 (m, 2H), 5.20-5.10 (d, J = 8.1 Hz, 1H), 5.09-4.99 (dq, J = 9.4, 6.3 Hz, 1H), 4.73-4.60 (q, J = 6.8 Hz, 1H), 3.94-3.84 (dd, J = 11.6, 7.2 Hz, 1H), 3.65-3.53 (d, J = 10.6 Hz, 1H), 3.49-3.41 (dd, J = 10.6, 7.0 Hz, 1H), 3.41-3.31 (dd, J = 11.5, 6.6 Hz, 1H), 2.85-2.66 (dd, J = 14.0, 3.8 Hz, 1H), 2.34-2.18 (t, J = 12.7 Hz, 1H), 2.15-2.00 (d, J = 8.3 Hz, 1H), 1.68-1.60 (tt, J = 8.0, 4.6 Hz, 1H), 1.60-1.56 (d, J = 2.4 Hz, 2H), 1.45-1.39 (s, 9H), 1.37-1.31 (d, J = 6.3 Hz, 3H), 1.08-0.98 (m, 2H), 0.97-0.83 (m, 2H) | ¹³C NMR (CDCl₃) δ 174.28, 172.12, 154.95, 139.08, 129.00, 128.51, 126.31, 80.18, 74.08, 73.25, 72.88, 53.42, 53.18, 45.79, 34.98, 28.26, 18.23, 12.84, 8.65 |
| 63 | — | (ATR) 3365, 2927, 2874, 1747, 1695, 1496, 1454, 1367, 1295, 1202, 1071, 853, 746 | HRMS-ESI (m/z) [M + Na]⁺ calc'd for $C_{23}H_{35}NO_7Na$; 460.2306, found, 460.2320 | ¹H NMR (CDCl₃) δ 7.35-7.12 (m, 5H), 5.17 (d, J = 8.3 Hz, 1H), 4.98 (dq, J = 8.6, 6.4 Hz, 1H), 4.60 (q, J = 7.5 Hz, 1H), 3.96-3.83 (m, 2H), 3.83-3.75 (m, 2H), 3.71 (dt, J = 8.8, 5.8 Hz, 1H), 3.49-3.37 (m, 2H), 3.26 (dd, J = 11.4, 7.4 Hz, 1H), 3.16 (t, J = 8.7 Hz, 1H), 3.09 (dd, J = 13.6, 3.5 Hz, 1H), 2.38 (t, J = 12.5 Hz, 1H), 2.13 (d, J = 13.0 Hz, 1H), 1.91 (d, J = 16.2 Hz, 1H), 1.86 (p, J = 5.8 Hz, 2H), 1.50 (d, J = 6.4 Hz, 3H), 1.42 (s, 9H) | ¹³C NMR (100 MHz, CDCl₃) δ 172.27, 154.99, 139.66, 129.13, 128.49, 126.22, 99.99, 85.31, 80.12, 77.22, 75.10, 72.86, 72.11, 71.09, 61.25, 52.89, 47.30, 35.14, 32.59, 28.27, 18.76 |
| 64 | — | (ATR) 1753, 1707, 1631, 1600, 1497, 1367, 1158, 1077, 1021, 956, 909, 730, | HRMS-ESI (m/z) [M + Na]⁺ calc'd for $C_{24}H_{33}NO_7Na$; 470.2149, found, 470.2160 | ¹H NMR (CDCl₃) δ 7.47-7.35 (d, J = 12.3 Hz, 1H), 7.35-7.25 (m, 1H), 7.25-7.16 (m, 1H), 7.16-7.04 (m, 2H), 5.84-5.71 (d, J = 12.3 Hz, 1H), 5.16-5.07 (d, J = 8.2 Hz, | ¹³C NMR (CDCl₃) δ 197.25, 172.15, 162.57, 138.45, 129.07, 128.58, 126.52, 108.48, 89.17, 80.33, 73.86, 72.57, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | 700 | | 1H), 5.07-4.95 (dq, J = 9.3, 6.4 Hz, 1H), 4.72-4.57 (q, J = 7.4 Hz, 1H), 4.01-3.85 (dd, J = 11.6, 7.5 Hz, 1H), 3.82-3.67 (t, J = 9.2 Hz, 1H), 2.14-2.05 (m, 1H), 3.59-3.49 (m, 1H), 3.49-3.40 (m, 1H), 3.36-3.23 (dd, J = 11.1, 7.6 Hz, 1H), 2.97-2.86 (dd, J = 13.8, 3.7 Hz, 1H), 2.45-2.30 (m, 1H), 2.21-2.14 (s, 3H), 2.14-2.05 (s, 1H), 1.49-1.41 (s, 9H), 1.41-1.36 (d, J = 6.4 Hz, 3H) | 71.38, 52.71, 46.43, 35.29, 28.69, 28.26, 18.73, 14.20 |
| 65 | 88-90 | (Thin film) 2980, 2933, 1744, 1708 | ESIMS m/z 541 ([M + Na]$^+$) | $^1$H NMR (CDCl$_3$) δ 7.31-7.24 (m, 2H), 7.22-7.16 (m, 3H), 5.98-5.87 (m, 1H), 5.35-5.28 (m, 1H), 5.19 (dd, J = 10.4, 1.4 Hz, 1H), 5.12 (dd, J = 8.5, 6.5 Hz, 1H), 4.94-4.86 (m, 1H), 4.22-4.16 (m, 1H), 4.11-4.04 (m, 2H), 3.85 (dd, J = 11.8, 8.6 Hz, 1H), 3.52 (d, J = 10.7 Hz, 1H), 3.42-3.35 (m, 1H), 3.23 (t, J = 8.9 Hz, 1H), 3.15-3.08 (m, 1H), 2.43-2.33 (m, 1H), 2.00 (s, 1H), 1.51-1.46 (m, 21H) | — |
| 66 | 131-133 | (Thin film) 2981, 1743, 1706 | ESIMS m/z 611 ([M + Na]$^+$) | $^1$H NMR (CDCl$_3$) δ 7.31-7.25 (m, 2H), 7.23-7.15 (m, 3H), 6.42-6.34 (m, 1H), 6.02-5.90 (m, 1H), 5.16-5.10 (m, 1H), 4.97-4.89 (m, 1H), 4.33-4.24 (m, 1H), 4.21-4.08 (m, 2H), 3.87 (dd, J = 11.8, 8.6 Hz, 1H), 3.54 (d, J = 10.5 Hz, 1H), 3.45-3.39 (m, 1H), 3.27 (t, J = 8.7 Hz, 1H), 3.03-2.97 (m, 1H), 2.49-2.40 (m, 1H), 2.05 (s, 1H), 1.49 (s, 18H), 1.46 (d, J = 6.4 Hz, 3H) | — |
| 67 | 80-83 | (Thin film) 1707, 1742, 2933, 2979 | ESIMS m/z 571 ([M + Na]$^+$) | (1:1 mixture of diastereomers); $^1$H NMR (CDCl$_3$) δ 7.31-7.23 (m, 6H), 7.18 (t, J = 6.8 Hz, 4H), 5.61 (ddd, J = 21.4, 15.2, 6.5 Hz, 2H), 5.42-5.29 (m, 2H), 5.03 (td, J = 7.6, 3.0 Hz, 2H), 4.93-4.79 (m, 2H), 4.04-3.82 (m, 6H), 3.52-3.31 (m, 6H), 3.18-3.09 (m, 2H), 2.30 (dt, J = 35.7, 12.6 Hz, 2H), 2.03-1.91 (m, 1H), 1.88-1.75 (m, 1H), 1.72 (dt, J = 6.4, 2.0 Hz, 6H), 1.47 (d, J = 2.9 Hz, 39H), 1.40 (d, J = 6.5 Hz, 3H), 1.25 (t, J = 5.8 Hz, 6H) | — |
| 68 | 98-100 | (Thin film) 1708, 1744, 2878, 2934, 2978 | ESIMS m/z 545 ([M + Na]$^+$) | $^1$H NMR (CDCl$_3$) δ 7.30-7.24 (m, 2H), 7.19 (dd, J = 5.0, 2.6 Hz, 3H), 5.12 (dd, J = 8.5, 6.4 Hz, 1H), 4.88 (dq, J = 9.1, 6.3 Hz, 1H), 4.07 (dd, J = 11.8, | — |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | | | 6.3 Hz, 1H), 3.84 (dd, J = 11.8, 8.6 Hz, 1H), 3.65-3.57 (m, 1H), 3.55-3.44 (m, 2H), 3.37 (dd, J = 10.8, 6.1 Hz, 1H), 3.19-3.07 (m, 2H), 2.35 (t, J = 12.7 Hz, 1H), 2.03-1.91 (m, 1H), 1.62 (q, J = 6.9 Hz, 2H), 1.48 (s, 21H), 0.95 (t, J = 7.4 Hz, 3H) | |
| 69 | 100-102 | (Thin film) 1707, 1743, 2936, 2980 | ESIMS m/z 613 ([M + Na]$^+$) | $^1$H NMR (CDCl$_3$) δ 7.27 (d, J = 8.6 Hz, 2H), 7.23-7.16 (m, 3H), 5.11 (dd, J = 8.4, 6.6 Hz, 1H), 4.98-4.81 (m, 1H), 4.08 (dd, J = 11.8, 6.6 Hz, 1H), 3.86 (dd, J = 11.8, 8.6 Hz, 1H), 3.73-3.64 (m, 1H), 3.61-3.48 (m, 2H), 3.39 (dd, J = 10.9, 6.0 Hz, 1H), 3.18 (t, J = 8.8 Hz, 1H), 3.02 (dd, J = 13.6, 3.6 Hz, 1H), 2.41 (t, J = 12.5 Hz, 1H), 2.32-2.12 (m, 2H), 1.99 (s, 1H), 1.83 (dq, J = 12.2, 6.1 Hz, 2H), 1.48 (s, 18H), 1.46 (d, J = 6.4 Hz, 3H) | — |
| 70 | — | (Thin film) 1708, 1743, 2875, 2933, 2977 | ESIMS m/z 571 ([M + Na]$^+$) | (1:1 mixture of diastereomers); $^1$H NMR (CDCl$_3$) δ 7.32-7.23 (m, 4H), 7.22-7.13 (m, 6H), 5.03 (t, J = 7.7 Hz, 2H), 4.88 (q, J = 8.0 Hz, 2H), 4.00 (dd, J = 11.7, 7.8 Hz, 2H), 3.90 (ddd, J = 11.7, 7.7, 1.6 Hz, 2H), 3.57 (dq, J = 13.4, 6.1 Hz, 2H), 3.50-3.40 (m, 4H), 3.36 (td, J = 7.6, 5.5 Hz, 2H), 3.14 (dt, J = 13.5, 4.4 Hz, 2H), 2.89 (t, J = 7.6 Hz, 1H), 2.71 (t, J = 7.6 Hz, 1H), 2.47-2.31 (m, 2H), 1.91 (s, 2H), 1.50-1.45 (m, 42H), 1.44-1.26 (m, 8H), 1.15 (t, J = 6.0 Hz, 4H), 0.91 (q, J = 7.1 Hz, 6H) | — |
| 71 | 127-129 | (Thin film) 1707, 1743, 2934, 2978 | ESIMS m/z 571 ([M + Na]$^+$) | $^1$H NMR (CDCl$_3$) δ 7.28 (dd, J = 15.9, 8.3 Hz, 2H), 7.23-7.15 (m, 3H), 5.83-5.72 (m, 1H), 5.64-5.51 (m, 1H), 5.12 (dd, J = 8.5, 6.5 Hz, 1H), 4.95-4.83 (m, 1H), 4.07 (tdd, J = 19.4, 10.3, 6.7 Hz, 3H), 3.84 (dd, J = 11.8, 8.6 Hz, 1H), 3.51 (d, J = 11.4 Hz, 1H), 3.37 (dd, J = 10.8, 6.0 Hz, 1H), 3.21 (t, J = 9.0 Hz, 1H), 3.14 (dd, J = 13.6, 3.5 Hz, 1H), 2.36 (t, J = 12.4 Hz, 1H), 2.13-2.03 (m, 2H), 2.01-1.94 (m, 1H), 1.50-1.46 (m, 21H), 1.00 (t, J = 7.4 Hz, 3H) | — |
| 72 | 94-97 | (Thin film) 1707, 1743, 2873, 2932, 2978 | ESIMS m/z 573 ([M + Na]$^+$) | $^1$H NMR (CDCl$_3$) δ 7.30-7.23 (m, 2H), 7.23-7.12 (m, 3H), 5.12 (dd, J = 8.5, 6.4 Hz, 1H), 4.87 (dq, J = 9.1, 6.4 Hz, 1H), 4.07 (dd, J = 11.8, 6.3 Hz, | — |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | | | 1H), 3.84 (dd, J = 11.8, 8.6 Hz, 1H), 3.68-3.60 (m, 1H), 3.55-3.48 (m, 2H), 3.36 (dd, J = 10.8, 6.1 Hz, 1H), 3.17-3.08 (m, 2H), 2.89 (t, J = 7.6 Hz, 1H), 2.71 (t, J = 7.6 Hz, 1H), 2.35 (t, J = 12.6 Hz, 1H), 2.03-1.90 (m, 1H), 1.64-1.56 (m, 2H), 1.48 (s, 21H), 1.35 (td, J = 7.4, 3.5 Hz, 4H), 0.93-0.87 (m, 3H) | |
| 73 | — | — | ESIMS m/z 478.6 ([M + Na]⁺) | ¹H NMR (CDCl₃) δ 7.34-7.20 (m, 5H), 7.20-7.04 (m, 4H), 7.02-6.88 (d, J = 8.7 Hz, 4H), 5.20-5.02 (dq, J = 9.1, 6.4 Hz, 2H), 4.71-4.57 (m, 1H), 4.37-4.21 (t, J = 8.9 Hz, 1H), 4.00-3.88 (dd, J = 11.6, 7.3 Hz, 1H), 3.60-3.44 (s, 2H), 3.38-3.21 (m, 1H), 3.07-2.93 (dd, J = 13.6, 3.1 Hz, 1H), 2.37-2.21 (t, J = 12.5 Hz, 1H), 2.22-2.09 (m, 1H), 1.46-1.40 (s, 9H), 1.40-1.34 (d, J = 6.4 Hz, 3H) | ¹³C NMR (CDCl₃) δ 172.29, 159.20, 154.98, 139.50, 129.75, 129.11, 128.42, 126.19, 121.34, 115.48, 81.96, 80.19, 75.39, 72.88, 72.08, 52.98, 47.56, 35.29, 28.29, 18.98 |
| 74 | — | (ATR) 2979, 2935, 2831, 1742, 1706, 1455, 1293, 1254, 1170, 1144, 1121, 1098, 1057, 913, 853, 732 | HRMS-ESI (m/z) [M + Na]⁺ calc'd for C₂₆H₃₉NO₈Na; 516.2568, found, 516.2572 | ¹H NMR (CDCl₃) δ 7.32-7.24 (m, 2H), 7.22-7.15 (dd, J = 5.1, 2.6 Hz, 3H), 5.18-5.06 (dd, J = 8.6, 6.3 Hz, 1H), 4.94-4.79 (dq, J = 9.1, 6.3 Hz, 1H), 4.16-4.01 (dd, J = 11.8, 6.3 Hz, 1H), 3.94-3.76 (dd, J = 11.8, 8.7 Hz, 1H), 3.59-3.50 (d, J = 10.5 Hz, 1H), 3.50-3.45 (s, 3H), 1.50-1.45 (m, 21H), 3.42-3.32 (dd, J = 10.8, 6.2 Hz, 1H), 3.14-3.01 (m, 2H), 2.47-2.31 (t, J = 12.4 Hz, 1H), 2.08-1.89 (s, 1H), 1.53-1.43 (s, 18H) | ¹³C NMR (CDCl₃) δ 169.94, 152.62, 139.87, 129.25, 128.33, 126.03, 86.42, 83.03, 75.09, 70.91, 59.58, 57.42, 46.62, 35.15, 27.92, 18.92 |
| 75 | — | (ATR) 2978, 2933, 1751, 1712, 1519, 1390, 1367, 1203, 1165, 1082 | HRMS-ESI (m/z) [M + Na]⁺ calc'd for C₂₄H₃₅NO₇Na; 472.2306, found, 472.2316 | ¹H NMR (CDCl₃) δ 7.34-7.27 (m, 2H), 7.22-7.13 (m, 3H), 5.12 (d, J = 8.2 Hz, 1H), 4.92 (dq, J = 9.1, 6.4 Hz, 1H), 4.59 (q, J = 7.3 Hz, 1H), 3.98-3.83 (m, 2H), 3.78 (dt, J = 9.0, 6.1 Hz, 1H), 3.49-3.41 (m, 1H), 3.37 (dd, J = 10.5, 6.3 Hz, 1H), 3.26 (dd, J = 11.4, 7.2 Hz, 1H), 3.19-3.03 (m, 2H), 2.70 (td, J = 6.1, 3.6 Hz, 2H), 2.32 (t, J = 13.0 Hz, 1H), 1.89 (s, 0H), 1.49 (d, J = 6.4 Hz, 2H), 1.42 (s, 7H) | ¹³C NMR (CDCl₃) δ 206.50, 172.18, 154.96, 139.78, 129.12, 128.43, 126.13, 85.39, 80.11, 77.33, 77.02, 76.70, 75.29, 72.94, 72.46, 67.16, 52.97, 47.14, 43.69, 35.16, 30.77, 28.27, 18.76 |
| 76 | — | (ATR) 2975, 2932, 2876, 1748, 1699, 1496, 1454, 1368, 1327, 1295, 1250, 1203, 1163, 1081, 731, 701 | HRMS-ESI (m/z) [M + Na]⁺ calc'd for C₂₄H₃₇NO₇Na; 474.2462; found, 474.2474 | (1:1 mixture of diastereomers); ¹H NMR (CDCl₃) δ 7.36-7.27 (m, 2H), 7.24-7.13 (m, 3H), 5.19 (dd, J = 25.1, 8.2 Hz, 1H), 5.07-4.91 (m, 1H), 4.60 (d, J = 6.8 Hz, 1H), 4.02 (dd, J = 6.3, 3.1 Hz, 1H), 3.97-3.81 (m, 2H), | ¹³C NMR (CDCl₃) δ 172.24, 155.00, 139.66, 139.56, 129.16, 129.10, 128.49, 126.22, 85.52, 85.28, 75.04, 66.93, 52.95, 47.29, 38.75, 35.20, 28.27, 23.67, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | | | 3.79-3.64 (m, 1H), 3.52-3.34 (m, 2H), 3.27 (dd, J = 18.9, 11.9 Hz, 1H), 2.01-1.86 (m, 1H), 3.16 (dd, J = 14.3, 8.5 Hz, 1H), 3.08 (dt, J = 13.5, 3.2 Hz, 1H), 2.56 (s, 1H), 2.48-2.31 (m, 1H), 1.81-1.66 (m, 2H), 1.51 (dd, J = 6.5, 1.9 Hz, 3H), 1.42 (s, 9H), 1.22 (d, J = 6.2 Hz, 3H) | 18.79 |
| 77 | — | (ATR) 2977, 2933, 2875, 1750, 1712, 1497, 1454, 1367, 1326, 1250, 1202, 1163, 1080, 1042, 1023 | HRMS-ESI (m/z) [M + Na]$^+$ calc'd for C$_{25}$H$_{37}$NO$_6$Na; 470.2513, found, 470.2522 | $^1$H NMR (CDCl$_3$) δ 7.38-7.23 (m, 2H), 7.23-7.10 (m, 3H), 5.16 (d, J = 8.2 Hz, 1H), 4.95 (dq, J = 9.2, 6.4 Hz, 1H), 4.80 (s, 1H), 4.77-4.69 (m, 1H), 4.59 (q, J = 7.4 Hz, 1H), 3.88 (dd, J = 11.5, 7.3 Hz, 1H), 3.83-3.71 (m, 1H), 1.57-1.46 (m, 3H), 3.65 (dt, J = 8.7, 7.0 Hz, 1H), 3.50-3.31 (m, 2H), 3.25 (dd, J = 11.4, 7.3 Hz, 1H), 3.20-3.02 (m, 2H), 2.32 (t, J = 6.9 Hz, 3H), 1.91 (s, 1H), 1.49 (d, J = 6.4 Hz, 3H), 1.41 (s, 9H) | $^{13}$C NMR (CDCl$_3$) δ 172.27, 154.98, 142.31, 139.91, 129.15, 128.43, 126.12, 111.99, 85.31, 80.06, 75.48, 72.79, 72.30, 71.29, 52.93, 47.28, 38.33, 35.19, 28.28, 22.88, 18.80 |
| 78 | — | — | — | — | — |
| 79 | — | — | ESIMS m/z 472.7 ([M + Na]$^+$) | $^1$H NMR (CDCl$_3$) δ 7.38-7.23 (m, 2H), 7.23-7.11 (m, 3H), 5.13 (d, J = 7.7 Hz, 1H), 4.94 (dq, J = 9.2, 6.4 Hz, 1H), 4.59 (q, J = 7.3 Hz, 1H), 3.88 (dd, J = 11.5, 7.3 Hz, 1H), 3.77-3.63 (m, 1H), 3.56 (dt, J = 8.7, 6.9 Hz, 1H), 3.49-3.41 (m, 1H), 3.37 (dd, J = 10.5, 6.4 Hz, 1H), 3.26 (dd, J = 11.3, 7.3 Hz, 1H), 3.20-3.04 (m, 2H), 2.30 (t, J = 12.6 Hz, 1H), 1.90 (s, 1H), 1.73 (dp, J = 13.3, 6.7 Hz, 1H), 1.55-1.46 (m, 5H), 1.42 (s, 9H), 0.91 (dd, J = 6.6, 0.8 Hz, 6H) | $^{13}$C NMR (CDCl$_3$) δ 172.25, 154.97, 139.96, 129.15, 128.43, 126.11, 85.13, 80.07, 75.58, 72.90, 72.45, 71.19, 52.97, 47.31, 39.17, 35.16, 28.27, 24.90, 22.70, 22.68, 18.77 |
| 80 | — | (ATR) 2980, 2934, 1742, 1706, 1455, 1393, 1367, 1313, 1254, 1145, 1120, 1060 | HRMS-ESI (m/z) [M + Na]$^+$ calc'd for C$_{27}$H$_{39}$F$_2$NO$_8$Na; 566.2536, found, 566.2556 | $^1$NMR (CDCl$_3$) δ 7.32-7.23 (m, 2H), 7.23-7.13 (m, 3H), 6.05-5.59 (m, 1H), 5.11 (dd, J = 8.5, 6.7 Hz, 1H), 4.91 (dq, J = 8.8, 6.4 Hz, 1H), 4.09 (dd, J = 11.8, 6.7 Hz, 1H), 3.97-3.79 (m, 2H), 3.79-3.64 (m, 1H), 3.51 (d, J = 10.7 Hz, 1H), 3.46-3.37 (m, 1H), 3.28 (t, J = 8.8 Hz, 1H), 3.06 (dd, J = 13.6, 3.8 Hz, 1H), 2.45 (t, J = 12.3 Hz, 1H), 2.13-1.88 (m, 1H), 1.57-1.39 (m, 21H) | $^{13}$C NMR (CDCl$_3$) δ 169.91, 152.61, 139.47, 129.20, 128.41, 126.20, 113.89, 85.92, 83.09, 74.55, 70.83, 57.30, 46.62, 35.08, 27.92, 18.88 |
| 81 | — | — | — | (1:1 mixture of diastereomers); $^1$H NMR (CDCl$_3$) δ 7.32-7.23 (m, 2H), 7.23-7.13 (m, 3H), 5.18 (d, J = 6.9 Hz, 1H), 5.02-4.86 (m, 1H), 4.60 (q, J = 7.2 Hz, 1H), 3.94-3.75 (m, 2H), 3.75-3.62 (m, 1H), 3.62-3.41 (m, 3H), 3.36 (dd, J = 10.5, | $^{13}$C NMR (CDCl$_3$) δ 172.21, 154.98, 139.93, 139.88, 129.13, 128.42, 126.10, 85.02, 80.03, 75.51, 75.45, 73.41, 73.39, 72.91, 72.58, 69.09, 68.84, 55.94, |

TABLE 3-continued

Analytical Data

| Cmpd No.* | MP (° C.) | IR (cm$^{-1}$) | MASS | $^1$H NMR* | $^{13}$C NMR* |
|---|---|---|---|---|---|
| | | | | 6.5 Hz, 1H), 3.33-3.22 (m, 4H), 3.21-3.04 (m, 2H), 2.29 (t, J = 12.5 Hz, 1H), 2.00-1.81 (m, 1H), 1.81-1.68 (m, 2H), 1.48 (s, 3H), 1.41 (s, 9H), 1.15 (d, J = 6.1 Hz, 3H) | 55.89, 53.01, 47.27, 47.14, 37.41, 37.35, 35.14, 35.03, 28.27, 19.09, 18.73 |
| 82 | 109-110 | — | ESIMS (m/z) 556.8 ([M + Na]$^+$) | $^1$H NMR (CDCl$_3$) δ 7.32-7.22 (m, 2H), 7.22-7.12 (m, 3H), 5.12 (dd, J = 8.5, 6.6 Hz, 1H), 5.07-4.98 (m, 1H), 4.98-4.83 (m, 2H), 4.15-4.02 (m, 2H), 3.95 (d, J = 11.8 Hz, 1H), 3.86 (dd, J = 11.8, 8.5 Hz, 1H), 3.52 (d, J = 10.7 Hz, 1H), 3.40 (dd, J = 10.9, 6.0 Hz, 1H), 3.23 (t, J = 8.8 Hz, 1H), 3.11 (dd, J = 13.6, 3.3 Hz, 1H), 2.40 (t, J = 12.5 Hz, 1H), 2.01 (d, J = 5.6 Hz, 1H), 1.77 (s, 3H), 1.54-1.39 (m, 21H) | $^{13}$C NMR (CDCl$_3$) δ 169.97, 152.62, 141.78, 140.01, 129.25, 128.33, 126.02, 112.13, 84.93, 83.01, 75.89, 75.20, 70.96, 57.44, 47.00, 35.02, 27.92, 19.79, 18.97 |
| 83 | 105-107 | (ATR) 2987, 2933, 2914, 2876, 1749, 1723, 1413, 1391, 1367, 1317, 1271, 1257, 1238, 1229, 1196, 1147, 1097, 1084, 1065, 1058, 854, 744 | HRMS-ESI (m/z) [M − H]$^-$ calc'd for C$_{29}$H$_{44}$NO$_8$; 534.3072, found, 534.3069 | $^1$H NMR (CDCl$_3$) δ 3.33-3.27 (m, 1H), 3.40-3.33 (m, 1H), 1.92-1.79 (m, 1H), 7.35-7.22 (m, 2H), 7.22-7.11 (m, 3H), 5.11 (dd, J = 8.5, 6.4 Hz, 1H), 4.88 (dq, J = 9.0, 6.3 Hz, 1H), 3.46-3.40 (m, 1H), 4.07 (dd, J = 11.8, 6.4 Hz, 1H), 3.84 (dd, J = 11.8, 8.6 Hz, 1H), 3.52 (d, J = 10.6 Hz, 1H), 3.18-3.08 (m, 2H), 2.35 (s, 1H), 1.98 (s, 1H), 1.48 (s, 21H), 0.94 (d, J = 6.7 Hz, 6H) | $^{13}$C NMR (CDCl$_3$) δ 169.98, 152.62, 140.12, 129.25, 128.32, 125.99, 84.52, 82.99, 78.82, 75.39, 70.96, 57.47, 47.05, 34.98, 29.16, 27.92, 19.49, 18.95 |
| 84 | — | — | ESIMS (m/z) 350.3 ([M + H]$^+$) | — | — |
| 89 | — | — | ESIMS (m/z) 322.7 ([M + H]$^+$) | — | — |
| 92 | — | — | ESIMS (m/z) 388.5 ([M + H]$^+$) | — | — |
| 93 | — | — | ESIMS (m/z) 350.6 ([M + H]$^+$) | — | — |
| 95 | — | — | ESIMS (m/z) 419.77 ([M + H]$^+$) | — | — |
| 96 | — | — | ESIMS (m/z) 384.67 ([M + Na]$^+$) | — | — |
| 97 | — | — | ESIMS (m/z) 384.5 ([M + Na]$^+$) | — | — |
| 99 | — | — | ESIMS (m/z) 294.5 ([M + H]$^+$) | — | — |
| 104 | — | — | ESIMS (m/z) 471.9 ([M + Na]$^+$) | — | — |
| 105 | — | (Neat) 3364, 2942, 1744, 1650, 1529, 1481, 1264 | HRMS-ESI (m/z) [M]$^+$ calc'd for C$_{27}$H$_{34}$N$_2$O$_7$, 498.2366; found, 498.2393 | $^1$NMR (CDCl$_3$) δ 11.97 (s, 1H), 8.54 (d, J = 8.3 Hz, 1H), 7.95 (d, J = 5.2 Hz, 1H), 7.33-7.24 (m, 2H), 7.22-7.14 (m, 3H), 6.84 (d, J = 5.2 Hz, 1H), 5.07-4.96 (m, | $^{13}$C NMR (CDCl$_3$) δ 171.19, 168.86, 155.25, 148.64, 140.58, 140.23, 130.10, 129.07, 128.41, 126.04, |

TABLE 3-continued

Analytical Data

| Cmpd No.* | MP (° C.) | IR (cm⁻¹) | MASS | ¹H NMR* | ¹³C NMR* |
|---|---|---|---|---|---|
| | | | | 1H), 4.94 (q, J = 7.4 Hz, 1H), 4.14-4.00 (m, 2H), 3.90 (s, 3H), 3.52-3.42 (m, 2H), 3.40-3.29 (m, 2H), 3.19 (dd, J = 13.6, 3.5 Hz, 1H), 2.39-2.26 (m, 1H), 1.97-1.83 (m, 1H), 1.84-1.64 (m, 6H), 1.62-1.49 (m, 2H), 1.52 (d, J = 6.5 Hz, 3H) | 109.55, 83.53, 83.29, 76.29, 73.36, 72.31, 56.02, 51.75, 47.50, 35.07, 32.67, 32.58, 23.00, 22.97, 18.88 |
| 106 | — | (Neat) 3379, 2949, 1752, 1677, 1505, 1201 | HRMS-ESI (m/z) [M]⁺ calc'd for $C_{30}H_{38}N_2O_9$, 570.2577; found, 570.2601 | ¹H NMR (600 MHz, $CDCl_3$) δ 8.61-8.46 (m, 1H), 8.31 (d, J = 5.4 Hz, 1H), 7.31-7.25 (m, 2H), 7.21-7.16 (m, 3H), 6.98 (d, J = 5.5 Hz, 1H), 5.02-4.96 (m, 1H), 4.96-4.90 (m, 1H), 4.11-4.06 (m, 1H), 4.02 (dd, J = 11.6, 7.0 Hz, 1H), 3.88 (s, 3H), 3.49-3.41 (m, 2H), 3.34-3.30 (m, 1H), 3.28 (dd, J = 11.6, 7.7 Hz, 1H), 3.19 (dd, J = 13.7, 3.6 Hz, 1H), 2.38 (s, 3H), 2.36-2.28 (m, 1H), 1.93-1.84 (m, 1H), 1.84-1.64 (m, 6H), 1.61-1.49 (m, 2H), 1.50 (d, J = 6.5 Hz, 3H) | ¹³C NMR (151 MHz, $CDCl_3$) δ 171.89, 170.28, 163.15, 160.20, 145.76, 143.94, 142.19, 140.35, 129.15, 128.44, 126.05, 109.69, 89.42, 83.57, 83.39, 76.16, 73.12, 72.56, 56.20, 52.07, 47.53, 35.16, 32.74, 32.63, 23.03, 23.01, 20.87, 18.93 |
| 107 | 72-74 | (Neat) | HRMS-ESI (m/z) [M]⁺ calc'd for $C_{29}H_{36}N_2O_8$, 540.2472; found, 540.2479 | ¹H NMR (600 MHz, $CDCl_3$) δ 8.61-8.46 (m, 1H), 8.31 (d, J = 5.4 Hz, 1H), 7.31-7.25 (m, 2H), 7.21-7.16 (m, 3H), 6.98 (d, J = 5.5 Hz, 1H), 5.02-4.96 (m, 1H), 4.96-4.90 (m, 1H), 4.11-4.06 (m, 1H), 4.02 (dd, J = 11.6, 7.0 Hz, 1H), 3.88 (s, 3H), 3.49-3.41 (m, 2H), 3.34-3.30 (m, 1H), 3.28 (dd, J = 11.6, 7.7 Hz, 1H), 3.19 (dd, J = 13.7, 3.6 Hz, 1H), 2.38 (s, 3H), 2.36-2.28 (m, 1H), 1.93-1.84 (m, 1H), 1.84-1.64 (m, 6H), 1.61-1.49 (m, 2H), 1.50 (d, J = 6.5 Hz, 3H) | ¹³C NMR (151 MHz, $CDCl_3$) δ 171.78, 168.85, 162.65, 159.41, 146.75, 141.19, 140.34, 137.50, 129.14, 128.44, 126.06, 109.90, 83.53, 83.39, 76.14, 73.09, 72.55, 56.30, 51.84, 47.50, 35.16, 32.74, 32.64, 23.03, 23.01, 20.73, 18.94 |
| 108 | — | (Neat) 3377, 2941, 1746, 1678, 1504, 1204 | HRMS-ESI (m/z) [M]⁺ calc'd for $C_{32}H_{42}N_2O_9$, 598.2890; found, 598.2905 | ¹H NMR (600 MHz, $CDCl_3$) δ 8.42 (d, J = 8.1 Hz, 1H), 8.25 (d, J = 5.4 Hz, 1H), 7.31-7.26 (m, 2H), 7.21-7.17 (m, 3H), 6.93 (d, J = 5.4 Hz, 1H), 5.77-5.71 (m, 2H), 5.03-4.93 (m, 2H), 4.12-4.08 (m, 1H), 4.05 (dd, J = 11.6, 7.0 Hz, 1H), 3.88 (s, 3H), 3.50-3.41 (m, 2H), 3.36-3.31 (m, 1H), 3.29 (dd, J = 11.6, 7.7 Hz, 1H), 3.19 (dd, J = 13.6, 3.6 Hz, 1H), 2.53 (hept, J = 7.0 Hz, 1H), 2.38-2.30 (m, 1H), 1.93-1.85 (m, 1H), 1.84-1.65 (m, 6H), 1.60-1.51 (m, 2H), 1.51 (d, J = 6.5 Hz, 3H), 1.13 (d, J = 7.1 Hz, 6H) | ¹³C NMR (151 MHz, $CDCl_3$) δ 176.23, 171.91, 163.12, 160.20, 145.62, 144.16, 141.84, 140.36, 129.14, 128.44, 126.04, 109.64, 89.76, 83.57, 83.36, 76.15, 73.02, 72.50, 56.15, 52.02, 47.50, 35.14, 33.85, 32.74, 32.63, 23.03, 23.01, 18.93, 18.68 |
| 109 | — | (ATR) 2977, 1741, 1705, 1355, 1119 | HRMS-ESI (m/z) [M]⁺ calc'd for $C_{30}H_{45}NO_8$, | ¹H NMR ($CDCl_3$) δ 7.26 (m, 2H), 7.19 (m, 3H), 5.03 (t, J = 7.7 Hz, 1H), 4.93-4.80 (m, 1H), | — |

TABLE 3-continued

Analytical Data

| Cmpd No. | MP (° C.) | IR (cm⁻¹) | MASS | ¹H NMR | ¹³C NMR |
|---|---|---|---|---|---|
| | | | 547.3145; found, 547.3164 | 4.10-4.03 (m, 1H), 4.00 (dd, J = 11.7, 7.6 Hz, 1H), 3.88 (dd, J = 11.7, 7.8 Hz, 1H), 3.45 (d, J = 5.2 Hz, 1H), 3.32 (t, J = 8.1 Hz, 1H), 3.15 (dd, J = 13.5, 3.4 Hz, 1H), 2.89 (t, J = 7.6 Hz, 1H), 2.71 (t, J = 7.6 Hz, 1H), 2.38 (t, J = 12.8 Hz, 1H), 1.90-1.61 (m, 8H), 1.60-1.37 (m, 21H) | |
| 110 | 198-200 | — | ESIMS m/z 336.2 [M]⁺ | — | — |
| 111 | — | — | ESIMS m/z 348.2 ([M + H]⁺) | ¹H NMR (CDCl₃) δ 8.55 (bs, 3H), 7.31-7.21 (m, 2H), 7.19-7.11 (m, 3H), 4.95-4.81 (m, 1H), 4.44-4.31 (m, 1H), 4.18-3.99 (m, 2H), 3.81-3.55 (m, 2H), 3.41-3.28 (m, 2H), 3.24 (t, J = 8.5 Hz, 1H), 3.12 (dd, J = 13.7, 3.6 Hz, 1H), 2.40-2.24 (m, 1H), 1.89-1.63 (m, 6H), 1.62-1.46 (m, 2H), 1.45 (d, J = 6.4 Hz, 3H) | ¹³C NMR (CDCl₃) δ 169.53, 140.03, 129.17, 128.48, 126.08, 83.53, 83.22, 72.75, 69.54, 67.10, 52.46, 47.42, 35.27, 32.82, 32.63, 23.06, 23.03, 18.85 |

*Cmpd. No.—Compound Number
*¹H NMR were run at 400 MHz unless noted otherwise
*¹³C NMR were run at 101 MHz unless noted otherwise

TABLE 4

Biological Testing Rating Scale
Rating Table for Fungal Pathogens

| % Control | Rating |
|---|---|
| 80-100 | A |
| More than 0-Less than 80 | B |
| Not Tested | C |
| No activity noticed in this bioassay | D |

TABLE 5

Biological Activity - Disease Control at 100 ppm

| Compound No. | PUCCRT* 1 DP* | PUCCRT* 3 DC* | SEPTTR* 1 DP | SEPTTR* 3 DC |
|---|---|---|---|---|
| 1 | A | A | A | A |
| 2 | A | A | A | A |
| 3 | A | A | A | A |
| 4 | A | A | A | A |
| 5 | C | C | C | C |
| 6 | A | A | A | B |
| 7 | A | A | A | A |
| 8 | A | A | A | A |
| 9 | A | A | A | A |
| 10 | A | A | A | A |
| 11 | B | B | B | B |
| 12 | A | B | B | B |
| 13 | D | B | B | B |
| 14 | A | A | A | B |
| 15 | B | B | B | B |
| 16 | A | A | A | A |
| 17 | A | A | A | A |
| 18 | A | A | A | A |
| 19 | A | A | A | A |
| 20 | B | B | B | B |
| 21 | A | B | B | B |
| 22 | A | A | A | A |
| 23 | A | A | A | A |
| 24 | A | A | A | A |
| 25 | A | A | A | A |
| 26 | A | A | A | A |
| 27 | A | B | B | B |
| 28 | A | A | B | B |
| 29 | A | A | B | A |
| 30 | A | B | B | B |
| 31 | A | A | A | A |
| 32 | A | B | B | A |
| 33 | A | A | A | A |
| 34 | A | A | A | A |
| 35 | A | A | A | A |
| 36 | A | A | A | A |
| 37 | A | A | A | A |
| 38 | A | A | A | A |
| 39 | A | A | A | A |
| 40 | A | A | A | A |
| 41 | A | B | B | B |
| 42 | A | A | A | A |
| 43 | A | A | A | A |
| 44 | A | A | A | A |
| 45 | A | A | A | A |
| 46 | A | A | A | A |
| 105 | A | A | A | A |
| 106 | A | A | A | A |

TABLE 5-continued

Biological Activity - Disease Control at 100 ppm

| Compound No. | PUCCRT* 1 DP* | PUCCRT* 3 DC* | SEPTTR* 1 DP | SEPTTR* 3 DC |
|---|---|---|---|---|
| 107 | A | A | A | A |
| 108 | A | A | A | B |

*PUCCRT—Wheat Brown Rust (*Puccinia triticina*)
*SEPTTR—Wheat Leaf Blotch (*Septoria tritici*)
*1 DP—1 Day Protectant
*3 DC—3 Day Curative

TABLE 6

Dropline Mobility Test at 1 ug/leaf

| Compound No. | PUCCRT* 1 DPM* | PUCCRT* 3 DCM* |
|---|---|---|
| 1 | B | B |
| 2 | B | B |
| 3 | B | B |
| 4 | C | C |
| 5 | C | C |
| 6 | C | C |
| 7 | B | B |
| 8 | B | B |
| 9 | B | B |
| 10 | B | B |
| 11 | C | C |
| 12 | C | C |
| 13 | C | C |
| 14 | C | C |
| 15 | C | C |
| 16 | C | C |
| 17 | B | B |
| 18 | B | B |
| 19 | B | D |
| 20 | B | D |
| 21 | B | D |
| 22 | B | B |
| 23 | B | B |
| 24 | B | B |
| 25 | B | D |
| 26 | B | B |
| 27 | B | B |
| 28 | B | D |
| 29 | B | B |
| 30 | B | D |
| 31 | B | B |
| 32 | B | B |
| 33 | B | D |
| 34 | B | D |
| 35 | B | D |
| 36 | B | B |
| 37 | B | D |
| 38 | B | B |
| 39 | A | A |
| 40 | B | B |
| 41 | B | B |
| 42 | B | B |
| 43 | A | B |
| 44 | B | B |
| 45 | A | A |
| 46 | A | A |
| 105 | C | C |
| 106 | C | C |
| 107 | C | C |
| 108 | C | C |

*PUCCRT—Wheat Brown Rust (*Puccinia triticina*)
*1 DPM—1 Day Protectant Mobility
*3 DCM—3 Day Curative Mobility

TABLE 7

Biological Activity - Disease Control at 100 ppm

| Cmpd. No.* | ALTESO* | CERCBE* | COCHSA* | COLLLA* 1DP* | ERYSCI* | ERYSGH* |
|---|---|---|---|---|---|---|
| 1 | C | C | C | C | C | C |
| 2 | C | C | C | C | C | C |
| 3 | A | A | A | A | A | A |
| 4 | C | C | C | C | C | C |
| 6 | C | C | C | C | C | C |
| 7 | A | A | B | C | A | A |
| 8 | A | A | B | A | A | A |
| 9 | A | A | B | C | A | A |
| 10 | B | A | B | C | A | A |
| 11 | C | C | C | C | C | C |
| 12 | C | C | C | C | C | C |
| 13 | C | C | C | C | C | C |
| 14 | C | C | C | C | C | C |
| 15 | B | B | C | B | D | D |
| 16 | A | A | C | A | A | A |
| 17 | C | C | C | C | C | C |
| 18 | C | C | C | C | C | C |
| 19 | C | C | C | C | C | C |
| 20 | C | C | C | C | C | C |
| 21 | C | C | C | C | C | C |
| 22 | A | A | C | A | A | A |
| 23 | A | A | C | A | A | A |
| 24 | C | C | C | C | C | C |
| 25 | C | C | C | C | C | C |
| 26 | A | A | C | A | A | A |
| 27 | C | C | C | C | C | C |
| 28 | C | C | C | C | C | C |
| 29 | C | C | C | C | C | C |

TABLE 7-continued

Biological Activity - Disease Control at 100 ppm

| Cmpd. No.* | ALTESO* | CERCBE* | COCHSA* | COLLLA* 1DP* | ERYSCI* | ERYSGH* |
|---|---|---|---|---|---|---|
| 30 | C | C | C | C | C | C |
| 31 | C | C | C | C | C | C |
| 32 | C | C | C | C | C | C |
| 33 | C | C | C | C | C | C |
| 34 | A | A | C | A | B | A |
| 35 | C | C | C | C | C | C |
| 36 | B | B | C | A | B | A |
| 37 | A | A | C | A | D | B |
| 38 | A | A | C | A | B | A |
| 39 | B | B | C | A | B | B |
| 40 | A | A | C | A | D | C |
| 41 | C | C | C | C | C | C |
| 42 | C | C | C | C | C | C |
| 43 | C | C | C | C | C | C |
| 44 | B | B | C | C | B | C |
| 45 | C | C | C | C | C | C |
| 46 | B | A | C | C | A | C |
| 105 | C | C | C | C | C | C |
| 106 | B | A | C | A | A | A |
| 107 | B | A | C | A | B | A |
| 108 | A | A | C | A | B | A |

*Cmpd. No.—Compound Number
*ALTESO—Tomato Early Blight (*Alternaria solani*)
*CERCBE—Leaf Spot Of Sugar Beets (*Cercospora beticola*)
*COCHSA—Spot Blotch Of Barley (*Cochliobolus sativus*)
*COLLLA—Cucumber Anthracnose (*Glomerella lagenarium*; Anamorph: *Colletotricum lagenarium*)
*ERYSCI—Powdery Mildew Of Cucumber (*Erysiphe cichoracearum*)
*ERYSGH—Barley Powdery Mildew (*Blumeria graminis* f.sp. *hordei*; Synonym: *Erysiphe graminis* f.sp. *hordei*)
*1DP—1 Day Protectant

TABLE 8

Biological Activity - Disease Control at 100 ppm

| Cmpd. No.* | ERYSGT* | LEPTNO* | PYRIOR* | RHYNSE* 1DP* | UNCINE* | VENTIN* |
|---|---|---|---|---|---|---|
| 1 | C | C | C | C | C | C |
| 2 | C | C | A | C | B | A |
| 3 | A | A | C | C | A | B |
| 4 | C | C | C | C | C | C |
| 6 | C | C | C | C | C | C |
| 7 | B | A | C | C | A | B |
| 8 | A | A | A | A | A | A |
| 9 | A | A | C | C | A | A |
| 10 | B | A | C | C | B | A |
| 11 | C | C | C | C | C | C |
| 12 | C | C | C | C | C | C |
| 13 | C | C | C | C | C | C |
| 14 | C | C | C | C | C | C |
| 15 | B | B | B | C | B | B |
| 16 | A | A | A | C | B | B |
| 17 | C | C | C | C | C | C |
| 18 | C | C | C | C | C | C |
| 19 | C | C | C | C | C | C |
| 20 | C | C | C | C | C | C |
| 21 | C | C | C | C | C | C |
| 22 | A | A | A | C | A | A |
| 23 | A | A | A | C | B | B |
| 24 | C | C | C | C | C | C |
| 25 | C | C | C | C | C | C |
| 26 | B | A | A | C | A | A |
| 27 | C | C | C | C | C | C |
| 28 | C | C | C | C | C | C |
| 29 | C | C | C | C | C | C |
| 30 | C | C | C | C | C | C |
| 31 | C | C | C | C | C | C |
| 32 | C | C | C | C | C | C |
| 33 | C | C | C | C | C | C |
| 34 | B | A | A | C | B | A |
| 35 | C | C | C | C | C | C |
| 36 | B | A | A | C | B | B |

TABLE 8-continued

Biological Activity - Disease Control at 100 ppm

| Cmpd. No.* | ERYSGT* | LEPTNO* | PYRIOR* | RHYNSE* 1DP* | UNCINE* | VENTIN* |
|---|---|---|---|---|---|---|
| 37 | B | A | A | C | B | B |
| 38 | B | A | A | C | B | B |
| 39 | B | A | A | C | B | B |
| 40 | B | A | A | C | B | A |
| 41 | C | C | C | C | C | C |
| 42 | C | C | C | C | C | C |
| 43 | C | C | C | C | C | C |
| 44 | C | A | A | C | B | B |
| 45 | C | C | C | C | C | C |
| 46 | C | A | A | C | B | A |
| 105 | C | C | C | C | C | C |
| 106 | C | A | C | C | C | C |
| 107 | C | A | A | A | B | B |
| 108 | C | A | A | A | A | A |

*Cmpd. No.—Compound Number
*ERYSGT—Wheat Powdery Mildew (*Blumeria graminis* f.sp. *tritici*; Synonym: *Erysiphe graminis* f.sp. *tritici*)
*LEPTNO—Wheat Glume Blotch (*Leptosphaeria nodorum*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*VENTIN—Apple Scab (*Venturia inaequalis*)
*1DP—1 Day Protectant

TABLE 9

Biological Activity - Disease Control at 25 ppm

| Compound Number | PHAKPA* | |
|---|---|---|
|  | 1 DP* | 2 DC* |
| 2 | A | A |
| 3 | A | A |
| 7 | A | A |
| 8 | A | A |
| 9 | A | A |
| 10 | A | A |
| 108 | A | A |

*PHAKPA—Asian Soybean Rust (*Phakopsora pachyrhizi*)
*1 DP—1 Day Protectant
*2 DC—2 Day Curative

What is claimed:

1. A compound of Formula I:

X is H or C(O)R$_6$;
Y is H, C(O)R$_6$, or Q;

Q is

R$_1$ is O;
R$_2$ is H, alkyl, alkenyl, aryl, heterocyclyl, silyl, each substituted with 0, 1 or multiple R$_5$, —C(O)R$_5$;
R$_3$ is phenyl or cyclohexyl;
R$_4$ is alkyl or alkoxy, substituted with 0, 1, or multiple R$_5$;
R$_5$ is hydroxy, alkyl, alkenyl, halo, haloalkyl, alkoxy, haloalkoxy, C(O)R$_8$, arylalkoxy, or aryl, where each R$_5$ is substituted with 0, 1, or multiple R$_9$;
R$_6$ is alkoxy, benzyloxy, substituted with 0, 1, or multiple R$_9$;
R$_7$ is H, —C(O)R$_4$, or —CH$_2$OC(O)R$_4$;
R$_8$ is hydroxy, alkyl, alkoxy, N(R$_9$)$_2$, arylalkoxy; and
R$_9$ is H or alkyl.

2. The compound according to claim 1, wherein X and Y are independently chosen from H or C(O)R$_6$.

3. The compound according to claim 2, wherein R$_2$ is independently chosen from H, alkyl, alkenyl, aryl, heterocyclyl, silyl, —C(O)R$_5$, each substituted with 0, 1 or multiple R$_5$.

4. The compound according to claim 3, wherein R$_3$ is independently phenyl or cyclohexyl.

5. The compound according to claim 4, wherein R$_5$ is alkyl or aryl substituted with 0, 1, or multiple R$_9$.

6. The compound according to claim 5, wherein R$_6$ is alkoxy or benzyloxy substituted with 0, 1, or multiple R$_9$.

7. The compound according to claim 6, wherein R$_9$ is hydrogen or alkyl.

8. The compound according to claim 1, wherein X is H and Y is Q.

9. The compound according to claim 8, wherein Q is

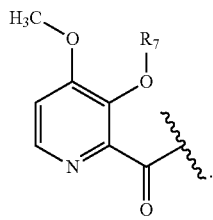

10. The compound according to claim 9, wherein $R_2$ is independently chosen from alkyl, aryl, or —C(O)$R_5$, each substituted with 0, 1 or multiple $R_5$.

11. The compound according to claim 10, wherein $R_3$ is phenyl.

12. The compound according to claim 11, wherein $R_4$ is alkyl substituted with 0, 1, or multiple $R_5$.

13. The compound according to claim 12, wherein $R_5$ is alkyl, aryl, alkoxy, or halo.

14. A composition for the control of a fungal pathogen including at least one of the compounds according to claim 1 and a phytologically acceptable carrier material.

15. A composition for the control of a fungal pathogen, comprising:
a compound of Formula I:

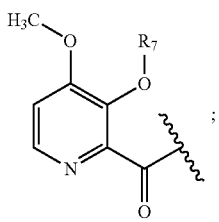

X is H or C(O)$R_6$;
Y is H, C(O)$R_6$, or Q;
Q is

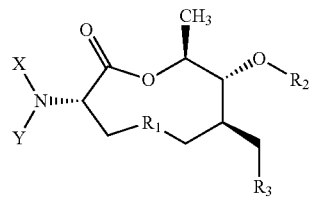

$R_1$ is O;
$R_2$ is H, alkyl, alkenyl, aryl, heterocyclyl, silyl, each substituted with 0, 1 or multiple $R_5$, —C(O)$R_5$;
$R_3$ is phenyl or cyclohexyl;
$R_4$ is alkyl or alkoxy, substituted with 0, 1, or multiple $R_5$;
$R_5$ is hydroxy, alkyl, alkenyl, halo, haloalkyl, alkoxy, haloalkoxy, C(O)$R_8$, arylalkoxy, or aryl, where each $R_5$ is substituted with 0, 1, or multiple $R_9$;
$R_6$ is alkoxy, benzyloxy, substituted with 0, 1, or multiple $R_9$;
$R_7$ is H, —C(O)$R_4$, or —CH$_2$OC(O)$R_4$;
$R_8$ is hydroxy, alkyl, alkoxy, N($R_9$)$_2$, arylalkoxy; and $R_9$ is H or alkyl, and
at least one additional agriculturally active compound selected from the group consisting of: pesticides, fungicides, insecticides, nematocides, miticides, arthropodicides, and bactericides, wherein the composition is effective for the control or at least one plant pathogen.

16. The composition according to claim, 14 wherein the plant pathogen is at least one pathogen selected from the group consisting of:
*Mycosphaerella graminicola, Septoria tritici, Puccinia triticina, Puccinia striiformis, Venturia inaequalis, Ustilago maydis,* Powdery Mildew of Grapevine *Uncinula necator, Rhynchosporium secalis, Magnaporthe grisea, Pseudoperonospora cubensis, Phakopsora pachyrhizi, Leptosphaeria nodorum, Blumeria graminis* forma specialis *tritici, Blumeria graminis* forma specialis *hordei, Erysiphe cichoracearum, Glomerella lagenarium, Cercospora beticola, Alternaria solani,* and *Pyrenophora teres.*

17. The composition according to claim 16, wherein the plant pathogen is at least one pathogen selected from the group consisting of *Septoria tritici, Puccinia triticina,* and *Phakopsora Pachyrhizi.*

18. A method for treating a plant, the method including the steps of:
applying an agriculturally effective amount of at least one compound of Formula I:

I wherein, X is H or C(O)$R_6$;
Y is H, C(O)$R_6$, or Q;
Q is

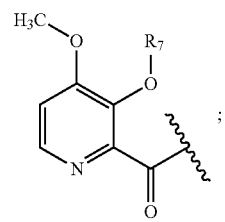

$R_1$ is O;
$R_2$ is H, alkyl, alkenyl, aryl, heterocyclyl, silyl, each substituted with 0, 1 or multiple $R_5$, —C(O)$R_5$;
$R_3$ is phenyl or cyclohexyl;
$R_4$ is alkyl or alkoxy, substituted with 0, 1, or multiple $R_5$;
$R_5$ is hydroxy, alkyl, alkenyl, halo, haloalkyl, alkoxy, haloalkoxy, C(O)$R_8$, arylalkoxy, or aryl, where each $R_5$ is substituted with 0, 1, or multiple $R_9$;
$R_6$ is alkoxy, benzyloxy, substituted with 0, 1, or multiple $R_9$;
$R_7$ is H, —C(O)$R_4$, or —CH$_2$OC(O)$R_4$;
$R_8$ is hydroxy, alkyl, alkoxy, N($R_9$)$_2$, arylalkoxy; and R₉ is H or alkyl, to at least one protion of a plant or to an area adjacent to a plant or to soil conditioned for growing a plant.

19. The composition according to claim, 14, wherein the plant pathogen is a causing agent of a disease selected from the group consisting of: Leaf Blotch of Wheat, Wheat Brown Rust, Stripe Rust, Scab of Apple, Blister Smut of Maize, Powdery Mildew of Grapevine, Barley scald, Blast of Rice, Downy Mildew of Cucurbits, Rust of Soybean, Glume Blotch of Wheat, Powdery Mildew of Wheat, Powdery Mildew of Barley, Powdery Mildew of Cucurbits, Anthracnose of Cucurbits, Leaf Spot of Beet, Early Blight of Tomato, and Net Blotch of Barley.

20. The compound of claim 1, wherein the compound is:

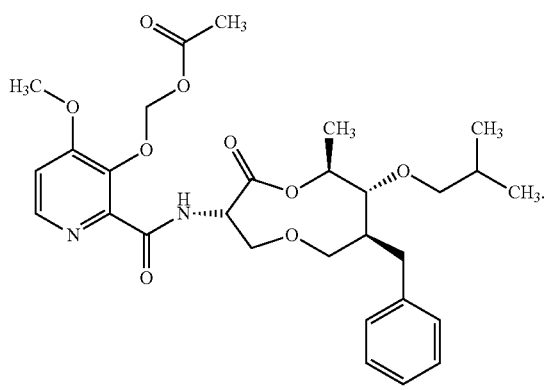

\* \* \* \* \*